US012691077B2

(12) United States Patent
Kaleko et al.

(10) Patent No.: US 12,691,077 B2
(45) Date of Patent: Jul. 28, 2026

(54) ALKALINE PHOSPHATASE FORMULATIONS AND USES THEREOF

(71) Applicant: Theriva Biologics, Inc., Rockville, MD (US)

(72) Inventors: Michael Kaleko, Rockville, MD (US); Ray Stapleton, Rockville, MD (US); Andrew Bristol, Rockville, MD (US); Steven Hubert, Rockville, MD (US); Cristina Freire, Oxford (GB)

(73) Assignee: Theriva Biologics, Inc., Rockville, MD (US)

( * ) Notice: Subject to any disclaimer, the term of this patent is extended or adjusted under 35 U.S.C. 154(b) by 931 days.

(21) Appl. No.: 17/615,942

(22) PCT Filed: Jun. 3, 2020

(86) PCT No.: PCT/US2020/035814
§ 371 (c)(1),
(2) Date: Dec. 2, 2021

(87) PCT Pub. No.: WO2020/247421
PCT Pub. Date: Dec. 10, 2020

(65) Prior Publication Data
US 2022/0323367 A1 Oct. 13, 2022

Related U.S. Application Data

(60) Provisional application No. 62/856,309, filed on Jun. 3, 2019.

(51) Int. Cl.
| | |
|---|---|
| *A61K 9/50* | (2006.01) |
| *A61K 9/16* | (2006.01) |
| *A61K 9/48* | (2006.01) |
| *A61K 38/46* | (2006.01) |

(52) U.S. Cl.
CPC .......... *A61K 9/5084* (2013.01); *A61K 9/1623* (2013.01); *A61K 9/1652* (2013.01); *A61K 9/4866* (2013.01); *A61K 9/5047* (2013.01); *A61K 38/465* (2013.01); *C12Y 301/03001* (2013.01)

(58) Field of Classification Search
CPC .......... C12Y 301/03001; A61K 9/5084; A61K 9/1623; A61K 9/4652; A61K 9/4866; A61K 9/5047; A61K 38/465
See application file for complete search history.

(56) References Cited

U.S. PATENT DOCUMENTS

| | | | |
|---|---|---|---|
| 5,773,226 A | 6/1998 | Millan |
| 5,821,095 A | 10/1998 | Hattori et al. |
| 5,891,699 A | 4/1999 | Boulain et al. |
| 5,948,410 A | 9/1999 | Van Scharrenburg et al. |
| 6,290,952 B1 | 9/2001 | Poelstra et al. |
| 6,406,899 B1 | 6/2002 | Hoelke et al. |
| 6,638,531 B1 | 10/2003 | Amerongen et al. |
| 6,649,390 B1 | 11/2003 | Sheng et al. |
| 6,686,392 B1 | 2/2004 | Avram et al. |
| 6,756,063 B2 | 6/2004 | Kiss |
| 6,793,928 B1 | 9/2004 | Van Scharrenburg et al. |
| 6,884,602 B2 | 4/2005 | Mueller et al. |
| 6,905,689 B2 | 6/2005 | Schneidinger et al. |
| 7,011,965 B2 | 3/2006 | Kiss |
| 7,014,852 B2 | 3/2006 | Kiss |
| 7,048,914 B2 | 5/2006 | Kiss |
| 7,060,677 B1 | 6/2006 | Van Berkel et al. |
| 7,312,198 B2 | 12/2007 | Kiss |
| 7,374,754 B2 | 5/2008 | Kiss |
| 7,423,029 B1 | 9/2008 | Kiss |
| 7,501,116 B2 | 3/2009 | Kiss |
| 7,557,081 B2 | 7/2009 | Kiss |
| 7,589,083 B2 | 9/2009 | Kiss |
| 7,655,620 B2 | 2/2010 | Kiss |
| 7,695,714 B2 | 4/2010 | Kiss |
| 7,718,170 B2 | 5/2010 | Kiss |
| 7,763,712 B2 | 7/2010 | Crine et al. |
| 7,781,423 B2 | 8/2010 | Kiss |
| 7,786,082 B2 | 8/2010 | Kiss |
| 7,790,685 B2 | 9/2010 | Kiss |
| 7,858,085 B2 | 12/2010 | Kiss |
| 7,943,126 B2 | 5/2011 | Tomatsu et al. |
| 7,943,606 B2 | 5/2011 | Kiss |

(Continued)

FOREIGN PATENT DOCUMENTS

| | | |
|---|---|---|
| CN | 106890326 A | 6/2017 |
| EP | 1952823 A1 | 8/2008 |

(Continued)

OTHER PUBLICATIONS

Rita Rochdi Haj-Ahmad, et al, Influences of Copolymers (Copovidone, Eudragit RL PO and Kollicoat MAE 30 DP) on Stability and Bioactivity of Spray-Dried and Freeze-Dried Lysozyme, 42 Drug Dev. Indust. Pharm. 2086 (Year: 2016).*

Bowen Jiang, et al, A Multiparticulate Delivery System for Potential Colonic Targeting Using Bovine Serum Albumin as a Model Protein, 34 Pharm. Res. 2663 (Year: 2017).*

(Continued)

*Primary Examiner* — Sean M Basquill

(74) *Attorney, Agent, or Firm* — Morgan, Lewis & Bockius LLP

(57) ABSTRACT

The present invention provides, in part, formulations comprising an alkaline phosphatase. Particularly, modified-release formulations comprising an alkaline phosphatase are provided, which release a substantial amount of the alkaline phosphatase in the intestines. Therapeutic uses of the alkaline phosphatase formulations are also provided.

19 Claims, 18 Drawing Sheets

Specification includes a Sequence Listing.

(56) References Cited

U.S. PATENT DOCUMENTS

| | | | |
|---|---|---|---|
| 7,960,529 | B2 | 6/2011 | Crine et al. |
| 7,964,188 | B2 | 6/2011 | Kiss |
| 8,372,638 | B2 | 2/2013 | Kiss |
| 8,460,654 | B2 | 6/2013 | Kiss |
| 8,557,545 | B2 | 10/2013 | Velders et al. |
| 8,574,863 | B2 | 11/2013 | Brands et al. |
| 8,586,032 | B2 | 11/2013 | Pickkers et al. |
| 8,603,464 | B2 | 12/2013 | Kiss |
| 8,647,854 | B2 | 2/2014 | Lee et al. |
| 8,691,208 | B2 | 4/2014 | Tomatsu et al. |
| 8,735,087 | B2 | 5/2014 | Brands et al. |
| 8,778,674 | B2 | 7/2014 | Kiss |
| 8,784,805 | B2 | 7/2014 | Brands |
| 8,784,833 | B2 | 7/2014 | Sly et al. |
| 8,932,587 | B2 | 1/2015 | Hodin et al. |
| 9,133,446 | B2 | 9/2015 | Aiba et al. |
| 9,631,185 | B2 | 4/2017 | Schyns et al. |
| 9,926,544 | B2 | 3/2018 | Raaben et al. |
| 9,976,129 | B2 | 5/2018 | Kamiya et al. |
| 9,988,620 | B2 | 6/2018 | Crine et al. |
| 10,000,532 | B2 | 6/2018 | Crine et al. |
| 10,052,366 | B2 | 8/2018 | Crine et al. |
| 10,449,236 | B2 | 10/2019 | Marozsan et al. |
| 10,570,380 | B2 | 2/2020 | Jonk et al. |
| 10,603,361 | B2 | 3/2020 | Odrijin |
| 2004/0091530 | A1 | 5/2004 | Ende et al. |
| 2005/0153338 | A1* | 7/2005 | Kratzsch ............ C12N 15/1027 |
| | | | 435/6.16 |
| 2007/0280922 | A1 | 12/2007 | Kiss |
| 2010/0158888 | A1 | 6/2010 | Kiss |
| 2010/0221234 | A1 | 9/2010 | Crine et al. |
| 2010/0297119 | A1 | 11/2010 | Crine et al. |
| 2011/0052560 | A1 | 3/2011 | Brands |
| 2011/0206654 | A1 | 8/2011 | Hodin et al. |
| 2012/0308526 | A1 | 12/2012 | Ohtake et al. |
| 2013/0045192 | A1 | 2/2013 | Movalia et al. |
| 2013/0071481 | A1 | 3/2013 | Ichikawa et al. |
| 2013/0108635 | A1 | 5/2013 | Crine et al. |
| 2013/0216624 | A1 | 8/2013 | Lee |
| 2013/0251701 | A1 | 9/2013 | Kiss |
| 2013/0280232 | A1 | 10/2013 | Brands et al. |
| 2013/0323244 | A1 | 12/2013 | Crine et al. |
| 2015/0216813 | A1 | 8/2015 | Everett et al. |
| 2017/0252327 | A1 | 9/2017 | Hodin et al. |
| 2018/0326018 | A1 | 11/2018 | Wacher et al. |

FOREIGN PATENT DOCUMENTS

| | | | |
|---|---|---|---|
| EP | 1759001 B1 | 4/2011 | |
| EP | 2158319 B1 | 7/2011 | |
| EP | 2368999 B1 | 3/2014 | |
| EP | 2662448 B1 | 12/2016 | |
| JP | 2017192381 | 10/2017 | |
| WO | WO 1999/026654 A1 | 6/1999 | |
| WO | WO 1999/033955 A1 | 7/1999 | |
| WO | WO 1999/037678 A2 | 7/1999 | |
| WO | WO 2000/032629 A2 | 6/2000 | |
| WO | WO 2001/034641 A2 | 5/2001 | |
| WO | WO 2001/056627 A1 | 8/2001 | |
| WO | WO 2002/060503 A1 | 8/2002 | |
| WO | WO 2004/054609 A1 | 7/2004 | |
| WO | WO 2004/112494 A2 | 12/2004 | |
| WO | WO 2005/055956 A2 | 6/2005 | |
| WO | WO 2005/074978 A1 | 8/2005 | |
| WO | WO 2005/103263 A1 | 11/2005 | |
| WO | WO 2007/055760 A2 | 5/2007 | |
| WO | WO 2007/081654 A2 | 7/2007 | |
| WO | WO-2008001341 A1 * | 1/2008 | .......... A61K 9/0004 |
| WO | WO 2008/024103 A1 | 2/2008 | |
| WO | WO 2008/094037 A1 | 8/2008 | |
| WO | WO 2008/104199 A1 | 9/2008 | |
| WO | WO 2008/104200 A1 | 9/2008 | |
| WO | WO 2008/133511 A2 | 11/2008 | |
| WO | WO 2008/138131 A1 | 11/2008 | |

| | | | |
|---|---|---|---|
| WO | WO 2009/028943 A1 | 3/2009 | |
| WO | WO 2009/106368 A1 | 9/2009 | |
| WO | WO 2010/025267 A2 | 3/2010 | |
| WO | WO 2010/151526 A1 | 12/2010 | |
| WO | WO 2011/057250 A1 | 5/2011 | |
| WO | WO 2011/134084 A1 | 11/2011 | |
| WO | WO 2012/054057 A1 | 4/2012 | |
| WO | WO 2012/169892 A2 | 12/2012 | |
| WO | WO 2012/177100 A2 | 12/2012 | |
| WO | WO 2013/058833 A1 | 4/2013 | |
| WO | WO 2013/059491 A1 | 4/2013 | |
| WO | WO 2015/112015 A1 | 7/2015 | |
| WO | WO 2015/112017 A1 | 7/2015 | |
| WO | WO 2015/166045 A2 | 11/2015 | |
| WO | WO 2016/090251 A1 | 6/2016 | |
| WO | WO 2016/123342 A2 | 8/2016 | |
| WO | WO 2017/031114 A1 | 2/2017 | |
| WO | WO 2017/058822 A1 | 4/2017 | |
| WO | WO 2017/074466 A1 | 5/2017 | |
| WO | WO 2017/155569 A1 | 9/2017 | |
| WO | WO 2017/173395 A1 | 10/2017 | |
| WO | WO 2017/173413 A1 | 10/2017 | |
| WO | WO 2017/214130 A1 | 12/2017 | |
| WO | WO 2018/009555 A1 | 1/2018 | |
| WO | WO 2018/011181 A1 | 1/2018 | |
| WO | WO 2018/035420 A1 | 2/2018 | |
| WO | WO 2018/127363 A1 | 7/2018 | |
| WO | WO 2018/164995 A1 | 9/2018 | |
| WO | WO 2018/175413 A1 | 9/2018 | |
| WO | WO 2018/183720 A1 | 10/2018 | |
| WO | WO 2017/203426 A1 | 2/2019 | |
| WO | WO 2018/183720 A9 | 7/2019 | |
| WO | WO 2019/139891 A1 | 7/2019 | |
| WO | WO 2019/172766 A1 | 9/2019 | |
| WO | WO 2019/183209 A1 | 9/2019 | |
| WO | WO 2019183208 A1 | 9/2019 | |
| WO | WO 2019/190752 A1 | 10/2019 | |
| WO | WO 2019/245938 A1 | 12/2019 | |
| WO | WO 2020/033867 A2 | 2/2020 | |
| WO | WO 2020/227263 A1 | 11/2020 | |
| WO | WO 2020/247421 A1 | 12/2020 | |
| WO | WO 2021/011754 A1 | 1/2021 | |

OTHER PUBLICATIONS

Hussein O. Ammar, et al, Effect of Antiadherents on the Physical and Drug Release Properties of Acrylic Polymer Films, 17 AAPS Pharmscitech 682 (Year: 2015).*

International Search Report & Written Opinion PCT Application No. PCT/US2020/035814, dated Sep. 22, 2020, 12 pages.

Alshahrani, et al., "Stability-enhanced Hot-melt Extruded Amorphous Solid Dispersions via Combinations of Soluplus® and HPMCAS-HF," American Association of Pharmaceutical Scientists, vol. 16, No. 4, pp. 824-834, Aug. 2015.

Beumer, et al., "Calf Intestinal Alkaline Phosphatase, A Novel Therapeutic Drug for Lipopolysaccharide (LPS)-Mediated Diseases, Attenuates LPS Toxicity in Mice and Piglets," The Journal of Pharmacology and Experimental Therapeutics, vol. 307, No. 2, pp. 737-744 (Jul. 2003).

Chen, et al., "A Role for Intestinal Alkaline Phosphatase in the Maintenance of Local Gut Community," Dig Dis Sci. Apr. 2011;56(4): 1020-1027 (doi:10.1007/s10620-010-1396-x).

Chen, et al. "Identification of specific targets for the gut mucosal defense factor intestinal alkaline phosphatase," American Journal of Physiology, Aug. 2010, Epub May 2012, vol. 299, No. 2 pp. G467-G475.

Cui, et al., "Faecal microbiota transplantation protects against radiation-induced toxicity", EMBO Molecular Medicine vol. 9 | No. 4 | 2017, 14 pages.

Curatolo, et al., "Utility of Hydroxypropylmethylcellulose Acetate Succinate (HPMCAS) for Initiation and Maintenance of Drug Supersaturation in the GI Milieu," Pharmaceutical Research, vol. 26, No. 6, pp. 1419-1431 (Jun. 2009).

Economopoulos, et al., "Prevention of antibiotic-associated metabolic syndrome in mice by intestinal alkaline phosphatase," Diabetes, Obesity and Metabolism, vol. 18, No. 5., pp. 519-527 (May 2016).

(56)        References Cited

OTHER PUBLICATIONS

Estaki, et al., "Interplay between intestinal alkaline phosphatase, diet, gut microbes and immunity," World Journal of Gastroenterology, 20(42), pp. 15650-15656 (Nov. 2014).

Friesen, et al., "Hydroxypropyl Methylcellulose Acetate Succinate-Based Spray-Dried Dispersions: An Overview," Molecular Pharmaceuticals, vol. 5, No. 6, pp. 1003-1019 (Dec. 2008).

Goldberg, et al., "Intestinal alkaline phosphatase is a gut mucosal defense factor maintained by enteral nutrition," PNAS, vol. 105, No. 9, pp. 3551-3556 (Mar. 2008).

Hauer-Jensen, et al., "Radiation Enteropathy—Pathogenesis, Treatment, and Prevention", Nat Rev Gastroenterol Hepatol. Aug. 2014 ; 11(8): 470-479. doi:10.1038/nrgastro.2014.46, 27 pages.

International Search Report & Written Opinion, PCT/US2018/023327, May 25, 2018, 12 pages.

Kaliannan, et al., "Intestinal alkaline phosphatase prevents metabolic syndrome in mice," PNAS, vol. 110, No. 17, pp. 7003-7008 (Apr. 2013).

Kühn, et al., "Intestinal alkaline phosphatase targets the gut barrier to prevent aging," JCI Insight. 2020;5(6):e134049. https://doi.org/10.1172/jci.insight.134049, 16 pages.

Lallès, "Intestinal alkaline phosphatase: novel functions and protective effects," Nutrition Reviews, vol. 72(2), pp. 82-94 (2014).

Liu, et al., "Intestinal Alkaline Phosphatase Regulates Tight Junction Protein Levels", J Am Coll Surg. Jun. 2016: 222(6): 1009-1017. doi:10.1016/j.jamcollsurg.2015.12.006.

Malo, et al., "Intestinal alkaline phosphatase preserves the normal homeostasis of gut microbiota," Gut 2010;59:1476-1484 (doi: 10.1136/gut.2010.211706).

Parlato, et al., "Human ALPI deficiency causes inflammatory bowel disease and highlights a key mechanism of gut homeostasis," EMBO Molecular Medicine, e8483, pp. 1-12 (Mar. 2018).

Peters, et al., "The Potential of Alkaline Phosphatase as a Treatment for Sepsis-Associated Acute Kidney Injury," Nephron Clin Pract 2014; 127: pp. 144-148 (Sep. 2014).

Ramasamy, et al., "Intestinal Alkaline Phosphatase Has Beneficial Effects in Mouse Models of Chronic Colitis", Inflamm Bowel Dis. Feb. 2011; 17(2): 532-542. doi:10.1002/ibd.21377.

Rentea, et al., "Radiation-induced changes in intestinal and tissue-nonspecific alkaline phosphatase: implications for recovery after radiation therapy", The American Journal of Surgery (2016) 212, 602-608, 7 pages.

Rieder, et al., "Animal models of intestinal fibrosis: new tools for the understanding of pathogenesis and therapy of human disease", Am J Physiol Gastrointest Liver Physiol 303: G786-G801, 2012, 16 pages.

Shah, et al., "Improved Human Bioavailability of Vemurafenib, a Practically Insoluble Drug, Using an Amorphous Polymer-Stabilized Solid Dispersion Prepared by a Solvent-Controlled Coprecipitation Process," Journal of Pharmaceutical Sciences, vol. 102, No. 3, pp. 967-981 (Mar. 2013).

* cited by examiner

FIGURE 1

HIAP – SEQ ID NO: 1

```
  1 mqgpwvllll glrlqlslgv ipaeeenpaf wnrqaaeald aakklqpiqk vaknlilflg
 61 dglgvptvta trilkgqkng klgpetplam drfpylalsk tynvdrqvpd saatataylc
121 gvkanfqtig lsaaarfnqc nttrgnevis vmnrakqagk svgvvtttrv qhaspagtya
181 htvnrnwysd admpasarqe gcqdiatqli snmdidvilg ggrkymfpmg tpdpeypada
241 sqngirldgk nlvqewlakh qgawyvwnrt elmqasldqs vthlmglfep gdtkyeihrd
301 ptldpslmem teaalrllsr nprgfylfve ggridhghhe gvayqaltea vmfddaiera
361 gqltseedtl tlvtadhshv fsfggytlrg ssifglapsk aqdskaytsi lygngpgyvf
421 nsgvrpdvne sesgspdyqq qaavplsset hggedvavfa rgpqahlvhg vqeqsfvahv
481 mafaaclepy tacdlappac ttdaahpvaa slpllagtll llgasaap
```

BIAP II with 248D – SEQ ID NO: 2. The signal peptide and sequence past 480 are derived from bIAP I.

```
  1 mqgacvllll glhlqlslgl ipaeeenpaf wnrqaaqald vakklqpiqt aaknvilflg
 61 dgmgvptvta trilkgqmng klgpetplam dqfpyvalsk tynvdrqvpd sagtataylc
121 gvkgnyrtig vsaaarynqc nttrgnevts vinrakkagk avgvvtttrv qhaspagaya
181 htvnrnwysd adlpadaqkn gcqdiaaqlv ynmdidvilg ggrmymfpeg tpdpeypdda
241 svngvrkdkq nlvqewqakh qgaqyvwnrt allqaaddss vthlmglfep admkynvqqd
301 htkdptlaem teaalqvlsr nprgfylfve ggridhghhd gkaymaltea imfdnaiaka
361 neltseldtl ilvtadhshv fsfggytlrg tsifglapgk aldsksytsi lygngpgyal
421 gggsrpdvng stseepsyrq qaavplaset hggedvavfa rgpqahlvhg vqeetfvahi
481 mafagcvepy tdcnlpapat atsipdaahl aasppplall agamlllap tly
```

BIAP IV – SEQ ID NO: 3

```
  1 mqwacvllll glwlqlsltf ipaeeedpaf wnrqaaqald vakklqpiqt aaknvilflg
 61 dgmgvptvta trilkgqmng klgpetplam dqfpyvalsk tynvdrqvpd sagtataylc
121 gvkgnyktig vsaaarynqc nttsgnevts vmnrakkagk svgvvttsrv qhaspagaya
181 htvnrnwysd adlpadaqty gcqdiatqlv nnmdidvilg ggrmymfpeg tpdpeypydv
241 nqtgvrkdkr nlvqewqakh qgaqyvwnrt ellqaandps vthlmglfep admkynvqqd
301 ptkdptleem teaalqvlsr npqgfylfve ggridhghhe gkaymaltdt vmfdnaiaka
361 neltseldtl ilatadhshv fsfggytlrg tsifglapsk asdnksytsi lygngpgyvl
421 ggglrpdvnd sisedpsyrq qaavplsses hggedvavfa rgpqahlvhg vqeetfvahv
481 mafagcvepy tdcnlpapsg lsdaahlaas ppslallaga mllllapaly
```

FIGURE 1 (continued)

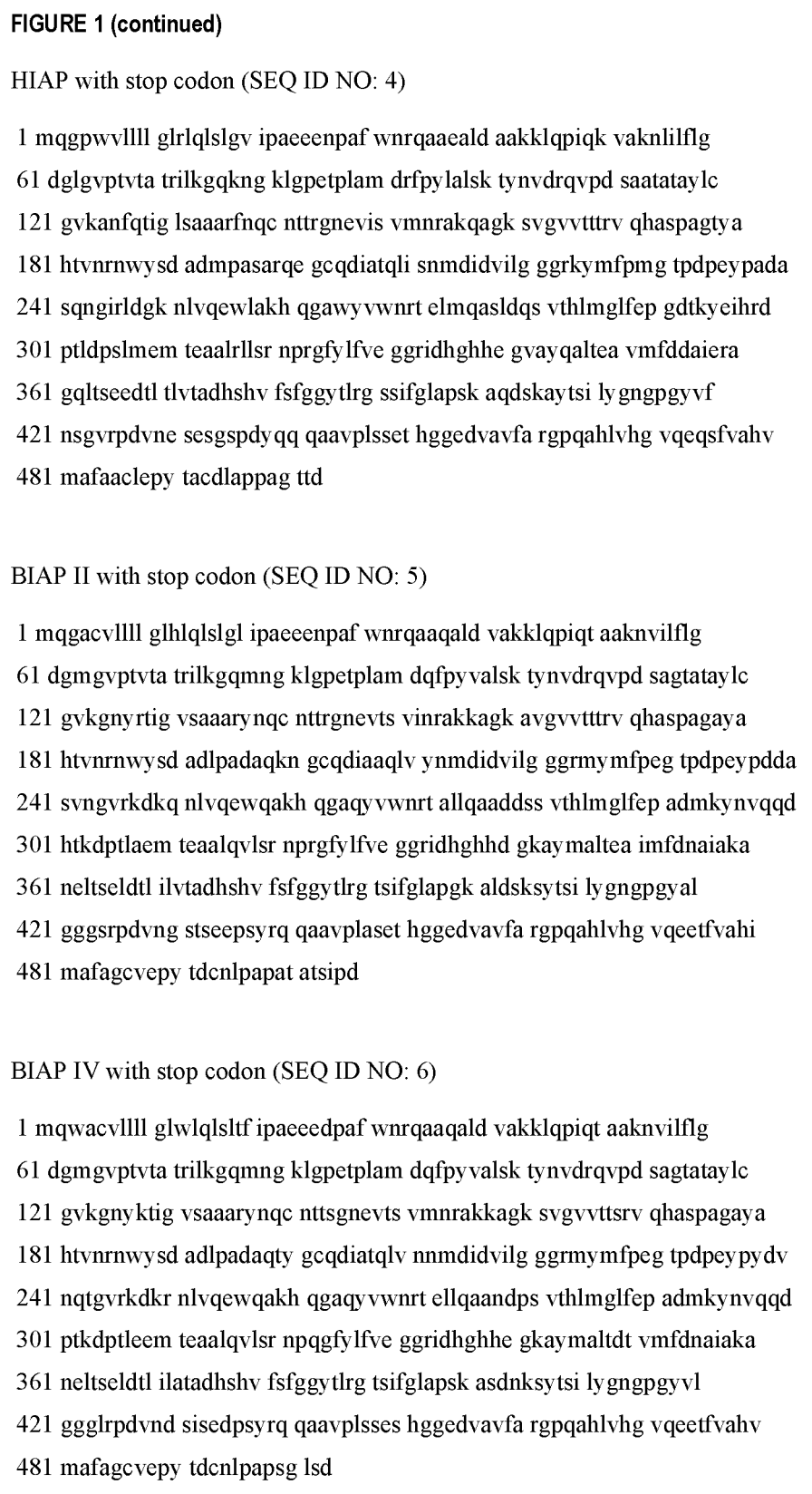

HIAP with stop codon (SEQ ID NO: 4)

1 mqgpwvllll glrlqlslgv ipaeeenpaf wnrqaaeald aakklqpiqk vaknlilflg 61 dglgvptvta trilkgqkng klgpetplam drfpylalsk tynvdrqvpd saatataylc 121 gvkanfqtig lsaaarfnqc nttrgnevis vmnrakqagk svgvvtttrv qhaspagtya 181 htvnrnwysd admpasarqe gcqdiatqli snmdidvilg ggrkymfpmg tpdpeypada 241 sqngirldgk nlvqewlakh qgawyvwnrt elmqasldqs vthlmglfep gdtkyeihrd 301 ptldpslmem teaalrllsr nprgfylfve ggridhghhe gvayqaltea vmfddaiera 361 gqltseedtl tlvtadhshv fsfggytlrg ssifglapsk aqdskaytsi lygngpgyvf 421 nsgvrpdvne sesgspdyqq qaavplsset hggedvavfa rgpqahlvhg vqeqsfvahv 481 mafaaclepy tacdlappag ttd BIAP II with stop codon (SEQ ID NO: 5)

1 mqgacvllll glhlqlslgl ipaeeenpaf wnrqaaqald vakklqpiqt aaknvilflg 61 dgmgvptvta trilkgqmng klgpetplam dqfpyvalsk tynvdrqvpd sagtataylc 121 gvkgnyrtig vsaaarynqc nttrgnevts vinrakkagk avgvvtttrv qhaspagaya 181 htvnrnwysd adlpadaqkn gcqdiaaqlv ynmdidvilg ggrmymfpeg tpdpeypdda 241 svngvrkdkq nlvqewqakh qgaqyvwnrt allqaaddss vthlmglfep admkynvqqd 301 htkdptlaem teaalqvlsr nprgfylfve ggridhghhd gkaymaltea imfdnaiaka 361 neltseldtl ilvtadhshv fsfggytlrg tsifglapgk aldsksytsi lygngpgyal 421 gggsrpdvng stseepsyrq qaavplaset hggedvavfa rgpqahlvhg vqeetfvahi 481 mafagcvepy tdcnlpapat atsipd BIAP IV with stop codon (SEQ ID NO: 6)

1 mqwacvllll glwlqlsltf ipaeeedpaf wnrqaaqald vakklqpiqt aaknvilflg 61 dgmgvptvta trilkgqmng klgpetplam dqfpyvalsk tynvdrqvpd sagtataylc 121 gvkgnyktig vsaaarynqc nttsgnevts vmnrakkagk svgvvttsrv qhaspagaya 181 htvnrnwysd adlpadaqty gcqdiatqlv nnmdidvilg ggrmymfpeg tpdpeypydv 241 nqtgvrkdkr nlvqewqakh qgaqyvwnrt ellqaandps vthlmglfep admkynvqqd 301 ptkdptleem teaalqvlsr npqgfylfve ggridhghhe gkaymaltdt vmfdnaiaka 361 neltseldtl ilatadhshv fsfggytlrg tsifglapsk asdnksytsi lygngpgyvl 421 ggglrpdvnd sisedpsyrq qaavplsses hggedvavfa rgpqahlvhg vqeetfvahv 481 mafagcvepy tdcnlpapsg lsd

FIGURE 1 (continued)

BIAP IV with stop codon after amino acid 508 (SEQ ID NO: 7)

1 mqwacvllll glwlqlsltf ipaeeedpaf wnrqaaqald vakklqpiqt aaknvilflg 61 dgmgvptvta trilkgqmng klgpetplam dqfpyvalsk tynvdrqvpd sagtataylc 121 gvkgnyktig vsaaarynqc nttsgnevts vmnrakkagk svgvvttsrv qhaspagaya 181 htvnrnwysd adlpadaqty gcqdiatqlv nnmdidvilg ggrmymfpeg tpdpeypydv 241 nqtgvrkdkr nlvqewqakh qgaqyvwnrt ellqaandps vthlmglfep admkynvqqd 301 ptkdptleem teaalqvlsr npqgfylfve ggridhghhe gkaymaltdt vmfdnaiaka 361 neltseldtl ilatadhshv fsfggytlrg tsifglapsk asdnksytsi lygngpgyvl 421 ggglrpdvnd sisedpsyrq qaavplsses hggedvavfa rgpqahlvhg vqeetfvahv 481 mafagcvepy tdcnlpapsg lsdaahla BIAP II with Fc Fusion (SEQ ID NO: 8) – Fc domain is underlined 1 mqgacvllll glhlqlslgl ipaeeenpaf wnrqaaqald vakklqpiqt aaknvilflg 61 dgmgvptvta trilkgqmng klgpetplam dqfpyvalsk tynvdrqvpd sagtataylc 121 gvkgnyrtig vsaaarynqc nttrgnevts vinrakkagk avgvvtttrv qhaspagaya 181 htvnrnwysd adlpadaqkn gcqdiaaqlv ynmdidvilg ggrmymfpeg tpdpeypdda 241 svngvrkdkq nlvqewqakh qgaqyvwnrt allqaaddss vthlmglfep admkynvqqd 301 htkdptlaem teaalqvlsr nprgfylfve ggridhghhd gkaymaltea imfdnaiaka 361 neltseldtl ilvtadhshv fsfggytlrg tsifglapgk aldsksytsi lygngpgyal 421 gggsrpdvng stseepsyrq qaavplaset hggedvavfa rgpqahlvhg vqeetfvahi 481 mafagcvepy tdcnlpapat atsipd<u>GGSGGSGGGGSGGGGSEPKSCDKTHTCPPCPAPE
LLGGPSVFLFPPKPKDTLMI SRTPEVTCVVVDVSHEDPQV KFNWYVDGVQVHNAKTKPRE
QQYNSTYRVVSVLTVLHQNW LDGKEYKCKVSNKALPAPIE KTISKAKGQPREPQVYTLPP
SREEMTKNQVSLTCLVKGFY PSDIAVEWESNGQPENNYKT TPPVLDSDGSFFLYSKLTVD
KSRWQQGNVFSCSVMHEALH NHYTQKSLSLSPGK</u>

BIAP IV with Fc Fusion (SEQ ID NO: 9) – Fc domain is underlined 1 mqwacvllll glwlqlsltf ipaeeedpaf wnrqaaqald vakklqpiqt aaknvilflg 61 dgmgvptvta trilkgqmng klgpetplam dqfpyvalsk tynvdrqvpd sagtataylc 121 gvkgnyktig vsaaarynqc nttsgnevts vmnrakkagk svgvvttsrv qhaspagaya 181 htvnrnwysd adlpadaqty gcqdiatqlv nnmdidvilg ggrmymfpeg tpdpeypydv 241 nqtgvrkdkr nlvqewqakh qgaqyvwnrt ellqaandps vthlmglfep admkynvqqd 301 ptkdptleem teaalqvlsr npqgfylfve ggridhghhe gkaymaltdt vmfdnaiaka

FIGURE 1 (continued)

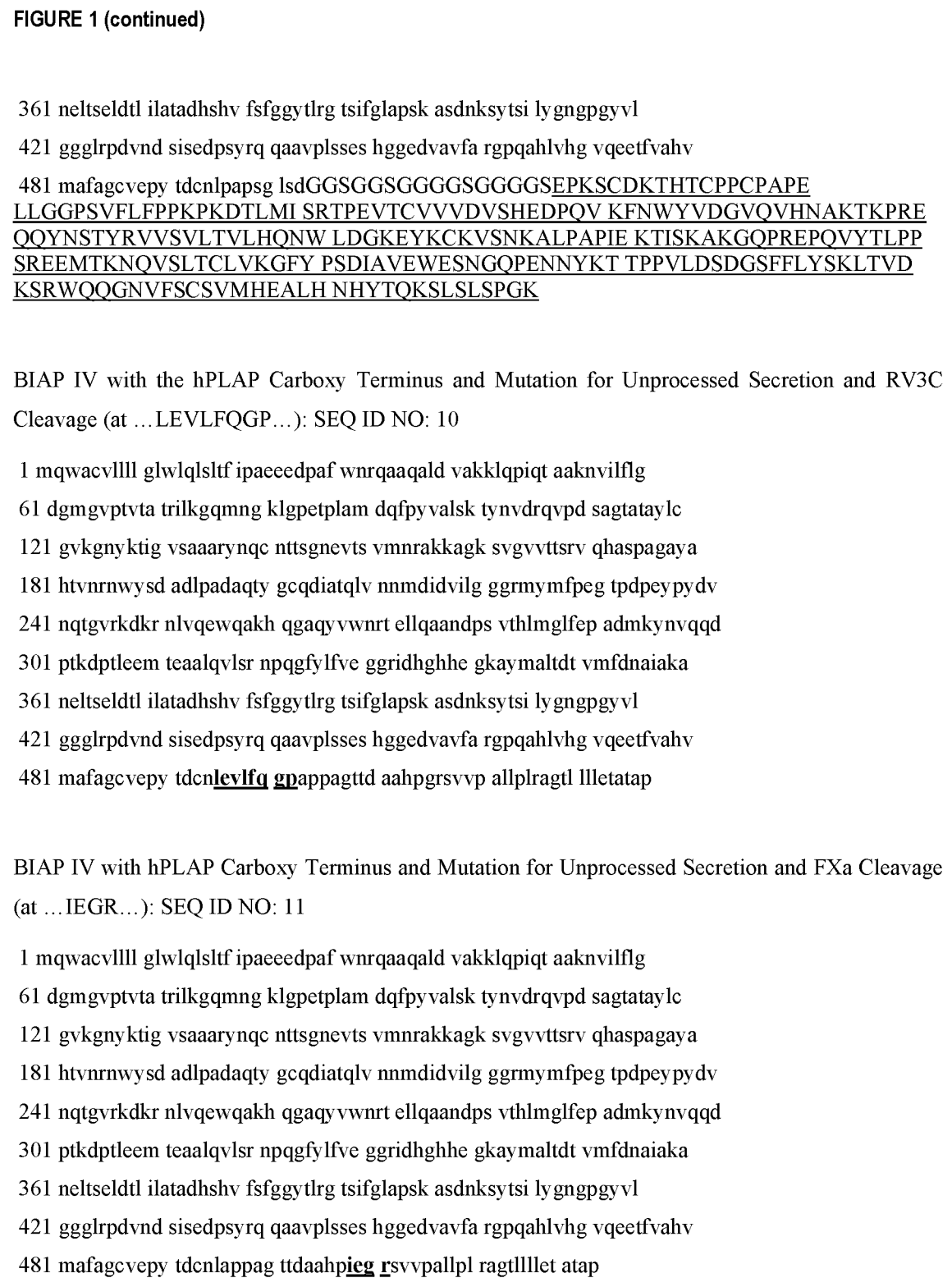

361 neltseldtl ilatadhshv fsfggytlrg tsifglapsk asdnksytsi lygngpgyvl 421 ggglrpdvnd sisedpsyrq qaavplsses hggedvavfa rgpqahlvhg vqeetfvahv 481 mafagcvepy tdcnlpapsg lsdGGSGGSGGGGSGGGGSEPKSCDKTHTCPPCPAPE
LLGGPSVFLFPPKPKDTLMI SRTPEVTCVVVDVSHEDPQV KFNWYVDGVQVHNAKTKPRE
QQYNSTYRVVSVLTVLHQNW LDGKEYKCKVSNKALPAPIE KTISKAKGQPREPQVYTLPP
SREEMTKNQVSLTCLVKGFY PSDIAVEWESNGQPENNYKT TPPVLDSDGSFFLYSKLTVD
KSRWQQGNVFSCSVMHEALH NHYTQKSLSLSPGK BIAP IV with the hPLAP Carboxy Terminus and Mutation for Unprocessed Secretion and RV3C Cleavage (at ...LEVLFQGP...): SEQ ID NO: 10

1 mqwacvllll glwlqlsltf ipaeeedpaf wnrqaaqald vakklqpiqt aaknvilflg 61 dgmgvptvta trilkgqmng klgpetplam dqfpyvalsk tynvdrqvpd sagtataylc 121 gvkgnyktig vsaaarynqc nttsgnevts vmnrakkagk svgvvttsrv qhaspagaya 181 htvnrnwysd adlpadaqty gcqdiatqlv nnmdidvilg ggrmymfpeg tpdpeypydv 241 nqtgvrkdkr nlvqewqakh qgaqyvwnrt ellqaandps vthlmglfep admkynvqqd 301 ptkdptleem teaalqvlsr npqgfylfve ggridhghhe gkaymaltdt vmfdnaiaka 361 neltseldtl ilatadhshv fsfggytlrg tsifglapsk asdnksytsi lygngpgyvl 421 ggglrpdvnd sisedpsyrq qaavplsses hggedvavfa rgpqahlvhg vqeetfvahv 481 mafagcvepy tdcnlevlfq gpappagttd aahpgrsvvp allplragtl llletatap BIAP IV with hPLAP Carboxy Terminus and Mutation for Unprocessed Secretion and FXa Cleavage (at ...IEGR...): SEQ ID NO: 11

1 mqwacvllll glwlqlsltf ipaeeedpaf wnrqaaqald vakklqpiqt aaknvilflg 61 dgmgvptvta trilkgqmng klgpetplam dqfpyvalsk tynvdrqvpd sagtataylc 121 gvkgnyktig vsaaarynqc nttsgnevts vmnrakkagk svgvvttsrv qhaspagaya 181 htvnrnwysd adlpadaqty gcqdiatqlv nnmdidvilg ggrmymfpeg tpdpeypydv 241 nqtgvrkdkr nlvqewqakh qgaqyvwnrt ellqaandps vthlmglfep admkynvqqd 301 ptkdptleem teaalqvlsr npqgfylfve ggridhghhe gkaymaltdt vmfdnaiaka 361 neltseldtl ilatadhshv fsfggytlrg tsifglapsk asdnksytsi lygngpgyvl 421 ggglrpdvnd sisedpsyrq qaavplsses hggedvavfa rgpqahlvhg vqeetfvahv 481 mafagcvepy tdcnlappag ttdaahpieg rsvvpallpl ragtllllet atap

FIGURE 1 (continued)

hIAP with native first intron (shown as bolded and underlined)- SEQ ID NO: 12

ATGCAGGGGCCCTGGGTGCTGCTGCTGCTGGGCCTGAGGCTACAGCTCTCCCTGGGCGTC
ATCCCAGGTAATGAGGCTCCCCAAGCTGTTCCACACACAGGGCACCCCCTCAGCCA
GGCTGACCTGATCTCTACTCTCCCCCTGGCCAGCTGAGGAGGAGAACCCGGCCTTCTG
GAACCGCCAGGCAGCTGAGGCCCTGGATGCTGCCAAGAAGCTGCAGCCCATCCAGAAGG
TCGCCAAGAACCTCATCCTCTTCCTGGGCGATGGGTTGGGGGTGCCCACGGTGACAGCCA
CCAGGATCCTAAAGGGGCAGAAGAATGGCAAACTGGGGCCTGAGACGCCCCTGGCCATG
GACCGCTTCCCATACCTGGCTCTGTCCAAGACATACAATGTGGACAGACAGGTGCCAGA
CAGCGCAGCCACAGCCACGGCCTACCTGTGCGGGGTCAAGGCCAACTTCCAGACCATCG
GCTTGAGTGCAGCCGCCCGCTTTAACCAGTGCAACACGACACGCGGCAATGAGGTCATC
TCCGTGATGAACCGGGCCAAGCAAGCAGGAAAGTCAGTAGGAGTGGTGACCACCACACG
GGTGCAGCACGCCTCGCCAGCCGGCACCTACGCACACACAGTGAACCGCAACTGGTACT
CAGATGCTGACATGCCTGCCTCAGCCCGCCAGGAGGGGTGCCAGGACATCGCCACTCAG
CTCATCTCCAACATGGACATTGACGTGATCCTTGGCGGAGGCCGCAAGTACATGTTTCCC
ATGGGGACCCCAGACCCTGAGTACCCAGCTGATGCCAGCCAGAATGGAATCAGGCTGGA
CGGGAAGAACCTGGTGCAGGAATGGCTGGCAAAGCACCAGGGTGCCTGGTATGTGTGGA
ACCGCACTGAGCTCATGCAGGCGTCCCTGGACCAGTCTGTGACCCATCTCATGGGCCTCT
TTGAGCCCGGAGACACGAAATATGAGATCCACCGAGACCCCACACTGGACCCCTCCCTG
ATGGAGATGACAGAGGCTGCCCTGCGCCTGCTGAGCAGGAACCCCCGCGGCTTCTACCT
CTTTGTGGAGGGCGGCCGCATCGACCATGGTCATCATGAGGGTGTGGCTTACCAGGCACT
CACTGAGGCGGTCATGTTCGACGACGCCATTGAGAGGGCGGGCCAGCTCACCAGCGAGG
AGGACACGCTGACCCTCGTCACCGCTGACCACTCCCATGTCTTCTCCTTTGGTGGCTACA
CCTTGCGAGGGAGCTCCATCTTCGGGTTGGCCCCCAGCAAGGCTCAGGACAGCAAAGCC
TACACGTCCATCCTGTACGGCAATGGCCCGGGCTACGTGTTCAACTCAGGCGTGCGACCA
GACGTGAATGAGAGCGAGAGCGGGAGCCCCGATTACCAGCAGCAGGCGGCGGTGCCCCT
GTCGTCCGAGACCCACGGAGGCGAAGACGTGGCGGTGTTTGCGCGCGGCCCGCAGGCGC
ACCTGGTGCATGGTGTGCAGGAGCAGAGCTTCGTAGCGCATGTCATGGCCTTCGCTGCCT
GTCTGGAGCCCTACACGGCCTGCGACCTGGCGCCTCCCGCCTGCACCACCGACGCCGCGC
ACCCAGTTGCCGCGTCGCTGCCACTGCTGGCCGGGACCCTGCTGCTGCTGGGGGCGTCCG
CTGCTCCCTGA hIAP with native 3' UTR (shown as bolded and underlined) – SEQ ID NO: 13

ATGCAGGGGCCCTGGGTGCTGCTGCTGCTGGGCCTGAGGCTACAGCTCTCCCTGGGCGTC
ATCCCAGCTGAGGAGGAGAACCCGGCCTTCTGGAACCGCCAGGCAGCTGAGGCCCTGGA
TGCTGCCAAGAAGCTGCAGCCCATCCAGAAGGTCGCCAAGAACCTCATCCTCTTCCTGGG
CGATGGGTTGGGGGTGCCCACGGTGACAGCCACCAGGATCCTAAAGGGGCAGAAGAATG
GCAAACTGGGGCCTGAGACGCCCCTGGCCATGGACCGCTTCCCATACCTGGCTCTGTCCA
AGACATACAATGTGGACAGACAGGTGCCAGACAGCGCAGCCACAGCCACGGCCTACCTG
TGCGGGGTCAAGGCCAACTTCCAGACCATCGGCTTGAGTGCAGCCGCCCGCTTTAACCAG
TGCAACACGACACGCGGCAATGAGGTCATCTCCGTGATGAACCGGGCCAAGCAAGCAGG
AAAGTCAGTAGGAGTGGTGACCACCACACGGGTGCAGCACGCCTCGCCAGCCGGCACCT
ACGCACACACAGTGAACCGCAACTGGTACTCAGATGCTGACATGCCTGCCTCAGCCCGC
CAGGAGGGGTGCCAGGACATCGCCACTCAGCTCATCTCCAACATGGACATTGACGTGAT
CCTTGGCGGAGGCCGCAAGTACATGTTTCCCATGGGGACCCCAGACCCTGAGTACCCAG
CTGATGCCAGCCAGAATGGAATCAGGCTGGACGGGAAGAACCTGGTGCAGGAATGGCTG
GCAAAGCACCAGGGTGCCTGGTATGTGTGGAACCGCACTGAGCTCATGCAGGCGTCCCT
GGACCAGTCTGTGACCCATCTCATGGGCCTC

FIGURE 1 (continued)

TTTGAGCCCGGAGACACGAAATATGAGATCCACCGAGACCCCACACTGGACCCCTCCCT
GATGGAGATGACAGAGGCTGCCCTGCGCCTGCTGAGCAGGAACCCCCGCGGCTTCTACC
TCTTTGTGGAGGGCGGCCGCATCGACCATGGTCATCATGAGGGTGTGGCTTACCAGGCAC
TCACTGAGGCGGTCATGTTCGACGACGCCATTGAGAGGGCGGGCCAGCTCACCAGCGAG
GAGGACACGCTGACCCTCGTCACCGCTGACCACTCCCATGTCTTCTCCTTTGGTGGCTAC
ACCTTGCGAGGGAGCTCCATCTTCGGGTTGGCCCCCAGCAAGGCTCAGGACAGCAAAGC
CTACACGTCCATCCTGTACGGCAATGGCCCGGGCTACGTGTTCAACTCAGGCGTGCGACC
AGACGTGAATGAGAGCGAGAGCGGGAGCCCCGATTACCAGCAGCAGGCGGCGGTGCCC
CTGTCGTCCGAGACCCACGGAGGCGAAGACGTGGCGGTGTTTGCGCGCGGCCCGCAGGC
GCACCTGGTGCATGGTGTGCAGGAGCAGAGCTTCGTAGCGCATGTCATGGCCTTCGCTGC
CTGTCTGGAGCCCTACACGGCCTGCGACCTGGCGCCTCCCGCCTGCACCACCGACGCCGC
GCACCCAGTTGCCGCGTCGCTGCCACTGCTGGCCGGGACCCTGCTGCTGCTGGGGGCGTC
CGCTGCTCCCTGATTTACTAAAACCTTGAAATAAAATTGTAAAACATCAGTTTGAAGG
CCTGACTCTCAGGGTAGTTCTTTTTTAATTCTGGGTTTT bIAP IV with the first intron from bIAP I (shown as bolded and underlined) – SEQ ID NO: 14

ATGCAGTGGGCCTGTGTGCTGCTGCTGCTGGGCCTGTGGCTACAGCTCTCCCTCACCTTC
ATCCCAGGTAATCAGGCGGCTCCCAGCAGCCCCTACTCACAGGGGCGGCTCTAGGC
TGACCTGACCAACACTCTCCCCTTGGGCAGCTGAGGAGGAAGACCCCGCCTTCTGGAA
CCGCCAGGCAGCCCAGGCCCTTGATGTAGCCAAGAAGTTGCAGCCGATCCAGACAGCTG
CCAAGAATGTCATCCTCTTCTTGGGGGATGGGATGGGGGTGCCTACGGTGACAGCCACTC
GGATCCTAAAGGGGCAGATGAATGGTAAGCTGGGACCTGAGACACCCCTGGCCATGGAC
CAGTTCCCATACGTGGCTCTGTCCAAGACATACAACGTGGACAGACAGGTGCCAGACAG
CGCAGGCACTGCCACTGCCTACCTGTGTGGGGTCAAGGGCAACTACAAAACCATTGGTG
TAAGTGCAGCCGCCCGCTACAACCAGTGCAACACAACAAGTGGCAATGAGGTCACGTCT
GTGATGAACCGGGCCAAGAAAGCAGGAAAGTCAGTGGGAGTGGTGACCACCTCCAGGG
TGCAGCATGCCTCCCCAGCCGGTGCTTATGCACACACGGTGAACCGAAACTGGTACTCAG
ATGCCGACCTGCCTGCCGATGCACAGACGTATGGCTGCCAGGACATCGCCACACAACTG
GTCAACAACATGGATATTGACGTGATCCTGGGTGGAGGCCGAATGTACATGTTTCCTGAG
GGGACCCCGGATCCTGAATACCCATACGATGTCAATCAGACTGGAGTCCGGAAGGACAA
GCGGAATCTGGTGCAGGAGTGGCAGGCCAAGCACCAGGGAGCCCAGTATGTGTGGAACC
GCACGGAGCTCCTTCAGGCAGCCAATGACCCCAGTGTAACACACCTCATGGGCCTCTTTG
AGCCGGCAGACATGAAGTATAATGTTCAGCAAGACCCCACCAAGGACCCGACCCTGGAG
GAGATGACGGAGGCGGCCCTGCAAGTGCTGAGCAGGAACCCCCAGGGCTTCTACCTCTT
CGTGGAGGGAGGCCGCATTGACCACGGTCACCATGAAGGCAAAGCTTATATGGCACTGA
CTGATACAGTCATGTTTGACAATGCCATCGCCAAGGCTAACGAGCTCACTAGCGAACTGG
ACACGCTGATCCTTGCCACTGCAGACCACTCCCATGTCTTCTCTTTTGGTGGCTACACACT
GCGTGGGACCTCCATTTTCGGTCTGGCCCCCAGCAAGGCCTCAGACAACAAGTCCTACAC
CTCCATCCTCTATGGCAATGGCCCTGGCTACGTGCTTGGTGGGGGCTTAAGGCCCGATGT
TAATGACAGCATAAGCGAGGACCCCTCGTACCGGCAGCAGGCGGCCGTGCCCCTGTCTA
GTGAGTCCCACGGGGGCGAGGACGTGGCGGTGTTCGCGCGAGGCCCGCAGGCGCACCTG
GTGCACGGCGTGCAGGAGGAGACCTTCGTGGCGCACGTCATGGCCTTTGCGGGCTGCGT
GGAGCCCTACACCGACTGCAATCTGCCGGCCCCTCTGGCCTCTCCGACGCCGCGCACCT
GGCGGCCAGCCCGCCTTCGCTGGCGCTGCTGGCCGGGGCGATGCTGCTGCTGCTGGCGCC
TGCCTTGTACTGA

FIGURE 1 (continued)

bIAP IV with the 3' UTR from bIAP I (shown as bolded and underlined) – SEQ ID NO: 15

ATGCAGTGGGCCTGTGTGCTGCTGCTGCTGGGCCTGTGGCTACAGCTCTCCCTCACCTTC
ATCCCAGCTGAGGAGGAAGACCCCGCCTTCTGGAACCGCCAGGCAGCCCAGGCCCTTGA
TGTAGCCAAGAAGTTGCAGCCGATCCAGACAGCTGCCAAGAATGTCATCCTCTTCTTGGG
GGATGGGATGGGGGTGCCTACGGTGACAGCCACTCGGATCCTAAAGGGGCAGATGAATG
GTAAGCTGGGACCTGAGACACCCCTGGCCATGGACCAGTTCCCATACGTGGCTCTGTCCA
AGACATACAACGTGGACAGACAGGTGCCAGACAGCGCAGGCACTGCCACTGCCTACCTG
TGTGGGGTCAAGGGCAACTACAAAACCATTGGTGTAAGTGCAGCCGCCCGCTACAACCA
GTGCAACACAACAAGTGGCAATGAGGTCACGTCTGTGATGAACCGGGCCAAGAAAGCAG
GAAAGTCAGTGGGAGTGGTGACCACCTCCAGGGTGCAGCATGCCTCCCCAGCCGGTGCT
TATGCACACACGGTGAACCGAAACTGGTACTCAGATGCCGACCTGCCTGCCGATGCACA
GACGTATGGCTGCCAGGACATCGCCACACAACTGGTCAACAACATGGATATTGACGTGA
TCCTGGGTGGAGGCCGAATGTACATGTTTCCTGAGGGGACCCCGGATCCTGAATACCCAT
ACGATGTCAATCAGACTGGAGTCCGGAAGGACAAGCGGAATCTGGTGCAGGAGTGGCAG
GCCAAGCACCAGGGAGCCCAGTATGTGTGGAACCGCACGGAGCTCCTTCAGGCAGCCAA
TGACCCCAGTGTAACACACCTCATGGGCCTCTTTGAGCCGGCAGACATGAAGTATAATGT
TCAGCAAGACCCCACCAAGGACCCGACCCTGGAGGAGATGACGGAGGCGGCCCTGCAA
GTGCTGAGCAGGAACCCCCAGGGCTTCTACCTCTTCGTGGAGGGAGGCCGCATTGACCA
CGGTCACCATGAAGGCAAAGCTTATATGGCACTGACTGATACAGTCATGTTTGACAATGC
CATCGCCAAGGCTAACGAGCTCACTAGCGAACTGGACACGCTGATCCTTGCCACTGCAG
ACCACTCCCATGTCTTCTCTTTTGGTGGCTACACACTGCGTGGGACCTCCATTTTCGGTCT
GGCCCCCAGCAAGGCCTCAGACAACAAGTCCTACACCTCCATCCTCTATGGCAATGGCCC
TGGCTACGTGCTTGGTGGGGGCTTAAGGCCCGATGTTAATGACAGCATAAGCGAGGACC
CCTCGTACCGGCAGCAGGCGGCCGTGCCCCTGTCTAGTGAGTCCCACGGGGGCGAGGAC
GTGGCGGTGTTCGCGCGAGGCCCGCAGGCGCACCTGGTGCACGGCGTGCAGGAGGAGAC
CTTCGTGGCGCACGTCATGGCCTTTGCGGGCTGCGTGGAGCCCTACACCGACTGCAATCT
GCCGGCCCCCTCTGGCCTCTCCGACGCCGCGCACCTGGCGGCCAGCCCGCCTTCGCTGGC
GCTGCTGGCCGGGGCGATGCTGCTGCTGCTGGCGCCTGCCTTGTACTGAGGGGACCCGG
GGGTGGGGACACAGGCCCCGCCCTCCCTGGGAGGCAGGAAGCAGCTCTCAAATAA
ACTGTTCTAAGTATGATACAGGAGTGATACATGTGTGAAGAGAAGCCCTTAGGTGG
GGGCACAGAGTGTCTGGGTGAGGGGGGTCAGGGTCACATCAGGAGGTTAGGGAGG
GGTTGATGAAGGGCTGACGTTGAGCAAAGACCAAAGGCAACTCAGAAGGACAGTG
GTGCAGGACTGGGTGTGGTCAGCAGGGGGACTGGTTGGGGGATCC

Bacillus subtilis JH642 alkaline phosphatase IV, mature protein nucleotide sequence – SEQ ID NO:
16

AAAAAACAAGACAAAGCTGAGATCAGAAATGTCATTGTGATGATAGGCGACGGCATGG
GGACGCCTTACATAAGAGCCTACCGTTCCATGAAAAATAACGGTGACACACCGAATAAC
CCGAAGTTAACAGAATTTGACCGGAACCTGACAGGCATGATGATGACGCATCCGGATGA
CCCTGACTATAATATTACAGATTCAGCAGCAGCCGGAACAGCATTAGCGACAGGCGTTA
AGACATATAACAATGCAATTGGCGTCGATAAAAACGGAAAAAAAGTGAAATCTGTACTT
GAAGAGGCCAAACAGCAAGGCAAGTCAACAGGGCTTGTCGCCACGTCTGAAATTAACCA
CGCCACTCCAGCCGCATATGGCGCCCACAATGAATCACGGAAAAACATGGACCAAATCG
CCAACAGCTATATGGATGACAAGATAAAAGGCAAACATAAAATAGACGTGCTGCTCGGC
GGCGGAAAATCTTATTTTAACCGCAAGAACAGAAACTTGACAAAGGAATTCAAACAAGC
CGGCTACAGCTATGTGACAACTAAACAAGCATTGAAAAAAAATAAAGATCAGCAGGTGC
TCGGGCTTTTCGCAGATGGAGGGCTTGCTAAAGCGCTCGACCGTGACAGTAAAACACCG
TCTCTCAAAGACATGACGGTTTCAG

FIGURE 1 (continued)

CAATTGATCGCCTGAACCAAAATAAAAAAGGATTTTTCTTGATGGTCGAAGGGAGCCAG
ATTGACTGGGCGGCCCATGACAATGATACAGTAGGAGCCATGAGCGAGGTTAAAGATTT
TGAACAGGCCTATAAAGCCGCGATTGAATTTGCGAAAAAAGACAAACATACACTTGTGA
TTGCAACTGCTGACCATACAACCGGCGGCTTTACCATTGGCGCAAACGGGGAAAGAAT
TGGCACGCAGAACCGATTCTCTCCGCTAAGAAAACACCTGAATTCATGGCCAAAAAAAT
CAGGAAGGCAAGCCGGTTAAAGATGTGCTCGCCCGCTATGCCAATCTGAAAGTCACATC
TGAAGAAATCAAAAGCGTTGAAGCAGCTGCACAGGCTGACAAAAGCAAAGGGGCCTCC
AAAGCCATCATCAAGATTTTTAATACCCGCTCCAACAGCGGATGGACGAGTACCGATCAT
ACCGGCGAAGAAGTACCGGTATACGCGTACGGCCCCGGAAAAGAAAAATTCCGCGGATT
GATTAACAATACGGACCAGGCAAACATCATATTTAAGATTTTAAAAACTGGAAAA

Bacillus subtilis JH642 alkaline phosphatase IV, mature protein amino acid sequence - SEQ ID NO:
17

KKQDKAEIRNVIVMIGDGMGTPYIRAYRSMKNNGDTPNNPKLTEFDRNLTGMMMTHPDDP
DYNITDSAAAGTALATGVKTYNNAIGVDKNGKKVKSVLEEAKQQGKSTGLVATSEINHATP
AAYGAHNESRKNMDQIANSYMDDKIKGKHKIDVLLGGGKSYFNRKNRNLTKEFKQAGYSY
VTTKQALKKNKDQQVLGLFADGGLAKALDRDSKTPSLKDMTVSAIDRLNQNKKGFFLMVE
GSQIDWAAHDNDTVGAMSEVKDFEQAYKAAIEFAKKDKHTLVIATADHTTGGFTIGANGEK
NWHAEPILSAKKTPEFMAKKISEGKPVKDVLARYANLKVTSEEIKSVEAAAQADKSKGASK
AIIKIFNTRSNSGWTSTDHTGEEVPVYAYGPGKEKFRGLINNTDQANIIFKILKTGK

BIAP II with stop codon and no leader sequence (SYN-020) - SEQ ID NO: 39:

LIPAEEENPAFWNRQAAQALDVAKKLQPIQTAAKNVILFLGDGMGVPTVTATRILKGQMNG
KLGPETPLAMDQFPYVALSKTYNVDRQVPDSAGTATAYLCGVKGNYRTIGVSAAARYNQC
NTTRGNEVTSVINRAKKAGKAVGVVTTTRVQHASPAGAYAHTVNRNWYSDADLPADAQK
NGCQDIAAQLVYNMDIDVILGGGRMYMFPEGTPDPEYPDDASVNGVRKDKQNLVQEWQAK
HQGAQYVWNRTALLQAADDSSVTHLMGLFEPADMKYNVQQDHTKDPTLAEMTEAALQVL
SRNPRGFYLFVEGGRIDHGHHDGKAYMALTEAIMFDNAIAKANELTSELDTLILVTADHSHV
FSFGGYTLRGTSIFGLAPGKALDSKSYTSILYGNGPGYALGGGSRPDVNGSTSEEPSYRQQAA
VPLASETHGGEDVAVFARGPQAHLVHGVQEETFVAHIMAFAGCVEPYTDCNLPAPATATSIP
D

Dissolution profiles (%Activity) of coated pellets in FaSSGF/FaSSIF or FaSSIF alone Calibration curve of SYN-020

$R^2 = 0.9998$ $y = 1.1643x - 0.019$

FIGURE 11
A)
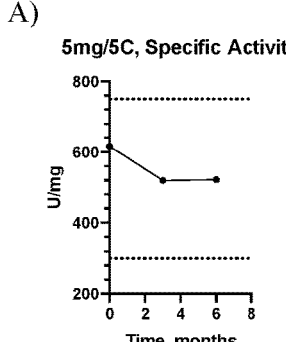
B)
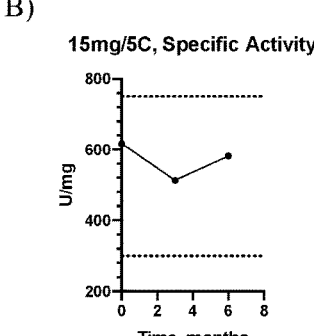
C)
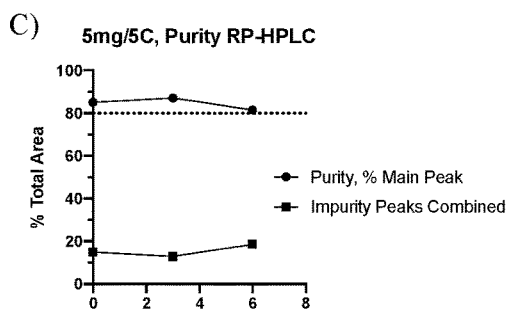
D)
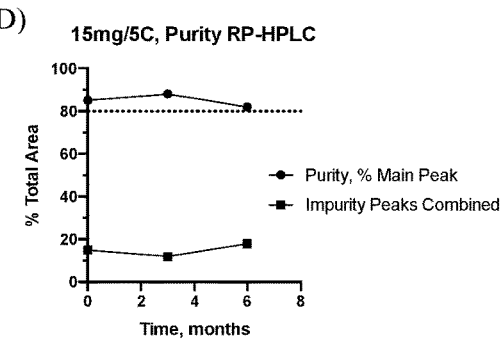
E)
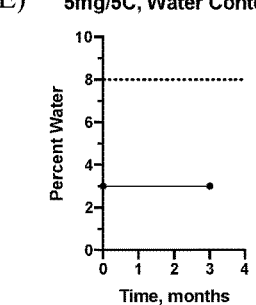
F)
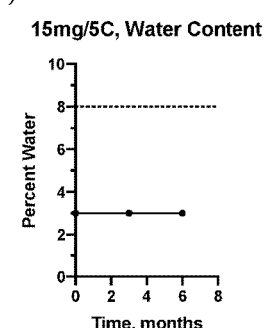
G)
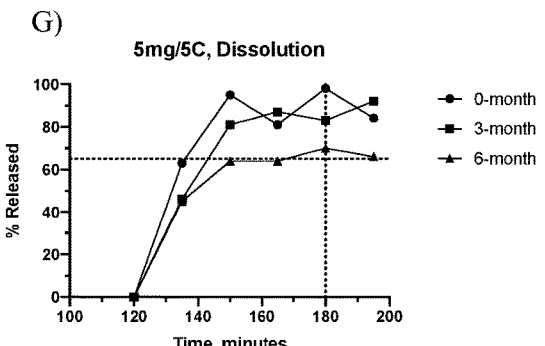
H)
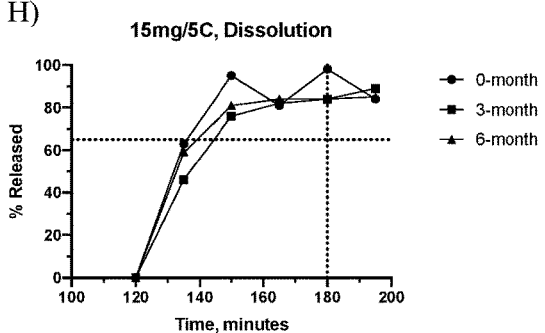

SEQUENCE LISTING

```
<160> NUMBER OF SEQ ID NOS: 39

<210> SEQ ID NO 1
<211> LENGTH: 528
<212> TYPE: PRT
<213> ORGANISM: Artificial Sequence
<220> FEATURE:
<223> OTHER INFORMATION: Synthetic polymer.

<400> SEQUENCE: 1

Met Gln Gly Pro Trp Val Leu Leu Leu Gly Leu Arg Leu Gln Leu
1               5                   10                  15

Ser Leu Gly Val Ile Pro Ala Glu Glu Glu Asn Pro Ala Phe Trp Asn
            20                  25                  30

Arg Gln Ala Ala Glu Ala Leu Asp Ala Ala Lys Lys Leu Gln Pro Ile
        35                  40                  45

Gln Lys Val Ala Lys Asn Leu Ile Leu Phe Leu Gly Asp Gly Leu Gly
    50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
            100                 105                 110

Ala Thr Ala Thr Ala Tyr Leu Cys Gly Val Lys Ala Asn Phe Gln Thr
        115                 120                 125

Ile Gly Leu Ser Ala Ala Ala Arg Phe Asn Gln Cys Asn Thr Thr Arg
    130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
            180                 185                 190

Met Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
    210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
                245                 250                 255

Leu Ala Lys His Gln Gly Ala Trp Tyr Val Trp Asn Arg Thr Glu Leu
            260                 265                 270

Met Gln Ala Ser Leu Asp Gln Ser Val Thr His Leu Met Gly Leu Phe
```

-continued

```
            275                 280                 285
Glu Pro Gly Asp Thr Lys Tyr Glu Ile His Arg Asp Pro Thr Leu Asp
    290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
                325                 330                 335

Gly His His Glu Gly Val Ala Tyr Gln Ala Leu Thr Glu Ala Val Met
            340                 345                 350

Phe Asp Asp Ala Ile Glu Arg Ala Gly Gln Leu Thr Ser Glu Glu Asp
            355                 360                 365

Thr Leu Thr Leu Val Thr Ala Asp His Ser His Val Phe Ser Phe Gly
    370                 375                 380

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                405                 410                 415

Gly Tyr Val Phe Asn Ser Gly Val Arg Pro Asp Val Asn Glu Ser Glu
            420                 425                 430

Ser Gly Ser Pro Asp Tyr Gln Gln Gln Ala Ala Val Pro Leu Ser Ser
            435                 440                 445

Glu Thr His Gly Gly Glu Asp Val Ala Val Phe Ala Arg Gly Pro Gln
    450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Cys Thr Thr Asp Ala Ala His Pro Val Ala Ala Ser Leu
            500                 505                 510

Pro Leu Leu Ala Gly Thr Leu Leu Leu Leu Gly Ala Ser Ala Ala Pro
            515                 520                 525
```

```
<210> SEQ ID NO 2
<211> LENGTH: 533
<212> TYPE: PRT
<213> ORGANISM: Artificial Sequence
<220> FEATURE:
<223> OTHER INFORMATION: Synthetic polymer.

<400> SEQUENCE: 2
```

```
Met Gln Gly Ala Cys Val Leu Leu Leu Leu Gly Leu His Leu Gln Leu
1               5                   10                  15

Ser Leu Gly Leu Ile Pro Ala Glu Glu Glu Asn Pro Ala Phe Trp Asn
                20                  25                  30

Arg Gln Ala Ala Gln Ala Leu Asp Val Ala Lys Lys Leu Gln Pro Ile
            35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
                100                 105                 110

Gly Thr Ala Thr Ala Tyr Leu Cys Gly Val Lys Gly Asn Tyr Arg Thr
```

```
            115                 120                 125

Ile Gly Val Ser Ala Ala Ala Arg Tyr Asn Gln Cys Asn Thr Thr Arg
    130                 135                 140

Gly Asn Glu Val Thr Ser Val Ile Asn Arg Ala Lys Lys Ala Gly Lys
145                 150                 155                 160

Ala Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
                180                 185                 190

Leu Pro Ala Asp Ala Gln Lys Asn Gly Cys Gln Asp Ile Ala Ala Gln
                195                 200                 205

Leu Val Tyr Asn Met Asp Ile Asp Val Ile Leu Gly Gly Gly Arg Met
    210                 215                 220

Tyr Met Phe Pro Glu Gly Thr Pro Asp Pro Glu Tyr Pro Asp Asp Ala
225                 230                 235                 240

Ser Val Asn Gly Val Arg Lys Asp Lys Gln Asn Leu Val Gln Glu Trp
                245                 250                 255

Gln Ala Lys His Gln Gly Ala Gln Tyr Val Trp Asn Arg Thr Ala Leu
                260                 265                 270

Leu Gln Ala Ala Asp Asp Ser Ser Val Thr His Leu Met Gly Leu Phe
                275                 280                 285

Glu Pro Ala Asp Met Lys Tyr Asn Val Gln Gln Asp His Thr Lys Asp
    290                 295                 300

Pro Thr Leu Ala Glu Met Thr Glu Ala Ala Leu Gln Val Leu Ser Arg
305                 310                 315                 320

Asn Pro Arg Gly Phe Tyr Leu Phe Val Glu Gly Gly Arg Ile Asp His
                325                 330                 335

Gly His His Asp Gly Lys Ala Tyr Met Ala Leu Thr Glu Ala Ile Met
                340                 345                 350

Phe Asp Asn Ala Ile Ala Lys Ala Asn Glu Leu Thr Ser Glu Leu Asp
                355                 360                 365

Thr Leu Ile Leu Val Thr Ala Asp His Ser His Val Phe Ser Phe Gly
    370                 375                 380

Gly Tyr Thr Leu Arg Gly Thr Ser Ile Phe Gly Leu Ala Pro Gly Lys
385                 390                 395                 400

Ala Leu Asp Ser Lys Ser Tyr Thr Ser Ile Leu Tyr Gly Asn Gly Pro
                405                 410                 415

Gly Tyr Ala Leu Gly Gly Gly Ser Arg Pro Asp Val Asn Gly Ser Thr
                420                 425                 430

Ser Glu Glu Pro Ser Tyr Arg Gln Gln Ala Ala Val Pro Leu Ala Ser
                435                 440                 445

Glu Thr His Gly Gly Glu Asp Val Ala Val Phe Ala Arg Gly Pro Gln
    450                 455                 460

Ala His Leu Val His Gly Val Gln Glu Glu Thr Phe Val Ala His Ile
465                 470                 475                 480

Met Ala Phe Ala Gly Cys Val Glu Pro Tyr Thr Asp Cys Asn Leu Pro
                485                 490                 495

Ala Pro Ala Thr Ala Thr Ser Ile Pro Asp Ala Ala His Leu Ala Ala
                500                 505                 510

Ser Pro Pro Pro Leu Ala Leu Leu Ala Gly Ala Met Leu Leu Leu Leu
                515                 520                 525

Ala Pro Thr Leu Tyr
    530
```

```
<210> SEQ ID NO 3
<211> LENGTH: 530
<212> TYPE: PRT
<213> ORGANISM: Artificial Sequence
<220> FEATURE:
<223> OTHER INFORMATION: Synthetic polymer.

<400> SEQUENCE: 3

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
            115                 120                 125

Ile Gly Val Ser Ala Ala Ala Arg Tyr Asn Gln Cys Asn Thr Thr Ser
    130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
            165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
            195                 200                 205

Leu Val Asn Asn Met Asp Ile Asp Val Ile Leu Gly Gly Gly Arg Met
    210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
            245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
    290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
            325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
        355                 360                 365
```

-continued

```
Thr Leu Ile Leu Ala Thr Ala Asp His Ser His Val Phe Ser Phe Gly
    370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Gly Leu Arg Pro Asp Val Asn Asp Ser Ile
                420                 425                 430

Ser Glu Asp Pro Ser Tyr Arg Gln Gln Ala Ala Val Pro Leu Ser Ser
                435                 440                 445

Glu Ser His Gly Gly Glu Asp Val Ala Val Phe Ala Arg Gly Pro Gln
    450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
                485                 490                 495

Ala Pro Ser Gly Leu Ser Asp Ala Ala His Leu Ala Ala Ser Pro Pro
                500                 505                 510

Ser Leu Ala Leu Leu Ala Gly Ala Met Leu Leu Leu Leu Ala Pro Ala
                515                 520                 525

Leu Tyr
    530

<210> SEQ ID NO 4
<211> LENGTH: 503
<212> TYPE: PRT
<213> ORGANISM: Artificial Sequence
<220> FEATURE:
<223> OTHER INFORMATION: Synthetic polymer.

<400> SEQUENCE: 4

Met Gln Gly Pro Trp Val Leu Leu Leu Gly Leu Arg Leu Gln Leu
1               5                   10                  15

Ser Leu Gly Val Ile Pro Ala Glu Glu Glu Asn Pro Ala Phe Trp Asn
                20                  25                  30

Arg Gln Ala Ala Glu Ala Leu Asp Ala Ala Lys Lys Leu Gln Pro Ile
            35                  40                  45

Gln Lys Val Ala Lys Asn Leu Ile Leu Phe Leu Gly Asp Gly Leu Gly
    50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
            100                 105                 110

Ala Thr Ala Thr Ala Tyr Leu Cys Gly Val Lys Ala Asn Phe Gln Thr
    115                 120                 125

Ile Gly Leu Ser Ala Ala Ala Arg Phe Asn Gln Cys Asn Thr Thr Arg
    130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
                180                 185                 190
```

-continued

```
Met Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
        210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
                245                 250                 255

Leu Ala Lys His Gln Gly Ala Trp Tyr Val Trp Asn Arg Thr Glu Leu
        260                 265                 270

Met Gln Ala Ser Leu Asp Gln Ser Val Thr His Leu Met Gly Leu Phe
        275                 280                 285

Glu Pro Gly Asp Thr Lys Tyr Glu Ile His Arg Asp Pro Thr Leu Asp
        290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
                325                 330                 335

Gly His His Glu Gly Val Ala Tyr Gln Ala Leu Thr Glu Ala Val Met
        340                 345                 350

Phe Asp Asp Ala Ile Glu Arg Ala Gly Gln Leu Thr Ser Glu Glu Asp
        355                 360                 365

Thr Leu Thr Leu Val Thr Ala Asp His Ser His Val Phe Ser Phe Gly
        370                 375                 380

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                405                 410                 415

Gly Tyr Val Phe Asn Ser Gly Val Arg Pro Asp Val Asn Glu Ser Glu
                420                 425                 430

Ser Gly Ser Pro Asp Tyr Gln Gln Gln Ala Ala Val Pro Leu Ser Ser
        435                 440                 445

Glu Thr His Gly Gly Glu Asp Val Ala Val Phe Ala Arg Gly Pro Gln
        450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Gly Thr Thr Asp
            500
```

```
<210> SEQ ID NO 5
<211> LENGTH: 506
<212> TYPE: PRT
<213> ORGANISM: Artificial Sequence
<220> FEATURE:
<223> OTHER INFORMATION: Synthetic polymer.

<400> SEQUENCE: 5

Met Gln Gly Ala Cys Val Leu Leu Leu Leu Gly Leu His Leu Gln Leu
1               5                   10                  15

Ser Leu Gly Leu Ile Pro Ala Glu Glu Glu Asn Pro Ala Phe Trp Asn
        20                  25                  30

Arg Gln Ala Ala Gln Ala Leu Asp Val Ala Lys Lys Leu Gln Pro Ile
        35                  40                  45
```

```
Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Arg Thr
            115                 120                 125

Ile Gly Val Ser Ala Ala Ala Arg Tyr Asn Gln Cys Asn Thr Thr Arg
    130                 135                 140

Gly Asn Glu Val Thr Ser Val Ile Asn Arg Ala Lys Lys Ala Gly Lys
145                 150                 155                 160

Ala Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Lys Asn Gly Cys Gln Asp Ile Ala Ala Gln
            195                 200                 205

Leu Val Tyr Asn Met Asp Ile Asp Val Ile Leu Gly Gly Gly Arg Met
    210                 215                 220

Tyr Met Phe Pro Glu Gly Thr Pro Asp Pro Glu Tyr Pro Asp Asp Ala
225                 230                 235                 240

Ser Val Asn Gly Val Arg Lys Asp Lys Gln Asn Leu Val Gln Glu Trp
                245                 250                 255

Gln Ala Lys His Gln Gly Ala Gln Tyr Val Trp Asn Arg Thr Ala Leu
            260                 265                 270

Leu Gln Ala Ala Asp Asp Ser Ser Val Thr His Leu Met Gly Leu Phe
            275                 280                 285

Glu Pro Ala Asp Met Lys Tyr Asn Val Gln Gln Asp His Thr Lys Asp
    290                 295                 300

Pro Thr Leu Ala Glu Met Thr Glu Ala Ala Leu Gln Val Leu Ser Arg
305                 310                 315                 320

Asn Pro Arg Gly Phe Tyr Leu Phe Val Glu Gly Gly Arg Ile Asp His
                325                 330                 335

Gly His His Asp Gly Lys Ala Tyr Met Ala Leu Thr Glu Ala Ile Met
            340                 345                 350

Phe Asp Asn Ala Ile Ala Lys Ala Asn Glu Leu Thr Ser Glu Leu Asp
    355                 360                 365

Thr Leu Ile Leu Val Thr Ala Asp His Ser His Val Phe Ser Phe Gly
    370                 375                 380

Gly Tyr Thr Leu Arg Gly Thr Ser Ile Phe Gly Leu Ala Pro Gly Lys
385                 390                 395                 400

Ala Leu Asp Ser Lys Ser Tyr Thr Ser Ile Leu Tyr Gly Asn Gly Pro
                405                 410                 415

Gly Tyr Ala Leu Gly Gly Gly Ser Arg Pro Asp Val Asn Gly Ser Thr
            420                 425                 430

Ser Glu Glu Pro Ser Tyr Arg Gln Gln Ala Ala Val Pro Leu Ala Ser
            435                 440                 445

Glu Thr His Gly Gly Glu Asp Val Ala Val Phe Ala Arg Gly Pro Gln
    450                 455                 460
```

-continued

```
Ala His Leu Val His Gly Val Gln Glu Glu Thr Phe Val Ala His Ile
465             470             475             480

Met Ala Phe Ala Gly Cys Val Glu Pro Tyr Thr Asp Cys Asn Leu Pro
            485             490             495

Ala Pro Ala Thr Ala Thr Ser Ile Pro Asp
        500             505

<210> SEQ ID NO 6
<211> LENGTH: 503
<212> TYPE: PRT
<213> ORGANISM: Artificial Sequence
<220> FEATURE:
<223> OTHER INFORMATION: Synthetic polymer.

<400> SEQUENCE: 6

Met Gln Trp Ala Cys Val Leu Leu Leu Leu Gly Leu Trp Leu Gln Leu
1               5               10              15

Ser Leu Thr Phe Ile Pro Ala Glu Glu Glu Asp Pro Ala Phe Trp Asn
            20              25              30

Arg Gln Ala Ala Gln Ala Leu Asp Val Ala Lys Lys Leu Gln Pro Ile
        35              40              45

Gln Thr Ala Ala Lys Asn Val Ile Leu Phe Leu Gly Asp Gly Met Gly
    50              55              60

Val Pro Thr Val Thr Ala Thr Arg Ile Leu Lys Gly Gln Met Asn Gly
65              70              75              80

Lys Leu Gly Pro Glu Thr Pro Leu Ala Met Asp Gln Phe Pro Tyr Val
            85              90              95

Ala Leu Ser Lys Thr Tyr Asn Val Asp Arg Gln Val Pro Asp Ser Ala
            100             105             110

Gly Thr Ala Thr Ala Tyr Leu Cys Gly Val Lys Gly Asn Tyr Lys Thr
            115             120             125

Ile Gly Val Ser Ala Ala Ala Arg Tyr Asn Gln Cys Asn Thr Thr Ser
    130             135             140

Gly Asn Glu Val Thr Ser Val Met Asn Arg Ala Lys Lys Ala Gly Lys
145             150             155             160

Ser Val Gly Val Val Thr Thr Ser Arg Val Gln His Ala Ser Pro Ala
            165             170             175

Gly Ala Tyr Ala His Thr Val Asn Arg Asn Trp Tyr Ser Asp Ala Asp
            180             185             190

Leu Pro Ala Asp Ala Gln Thr Tyr Gly Cys Gln Asp Ile Ala Thr Gln
            195             200             205

Leu Val Asn Asn Met Asp Ile Asp Val Ile Leu Gly Gly Gly Arg Met
    210             215             220

Tyr Met Phe Pro Glu Gly Thr Pro Asp Pro Glu Tyr Pro Tyr Asp Val
225             230             235             240

Asn Gln Thr Gly Val Arg Lys Asp Lys Arg Asn Leu Val Gln Glu Trp
            245             250             255

Gln Ala Lys His Gln Gly Ala Gln Tyr Val Trp Asn Arg Thr Glu Leu
            260             265             270

Leu Gln Ala Ala Asn Asp Pro Ser Val Thr His Leu Met Gly Leu Phe
        275             280             285

Glu Pro Ala Asp Met Lys Tyr Asn Val Gln Gln Asp Pro Thr Lys Asp
    290             295             300

Pro Thr Leu Glu Glu Met Thr Glu Ala Ala Leu Gln Val Leu Ser Arg
305             310             315             320
```

-continued

Asn Pro Gln Gly Phe Tyr Leu Phe Val Glu Gly Gly Arg Ile Asp His
            325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
            355                 360                 365

Thr Leu Ile Leu Ala Thr Ala Asp His Ser His Val Phe Ser Phe Gly
        370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Gly Leu Arg Pro Asp Val Asn Asp Ser Ile
            420                 425                 430

Ser Glu Asp Pro Ser Tyr Arg Gln Gln Ala Ala Val Pro Leu Ser Ser
            435                 440                 445

Glu Ser His Gly Gly Glu Asp Val Ala Val Phe Ala Arg Gly Pro Gln
        450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
                485                 490                 495

Ala Pro Ser Gly Leu Ser Asp
            500

<210> SEQ ID NO 7
<211> LENGTH: 508
<212> TYPE: PRT
<213> ORGANISM: Artificial Sequence
<220> FEATURE:
<223> OTHER INFORMATION: Synthetic polymer.

<400> SEQUENCE: 7

Met Gln Trp Ala Cys Val Leu Leu Leu Leu Gly Leu Trp Leu Gln Leu
1               5                   10                  15

Ser Leu Thr Phe Ile Pro Ala Glu Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
        50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
                100                 105                 110

Gly Thr Ala Thr Ala Tyr Leu Cys Gly Val Lys Gly Asn Tyr Lys Thr
            115                 120                 125

Ile Gly Val Ser Ala Ala Ala Arg Tyr Asn Gln Cys Asn Thr Thr Ser
        130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
            195                 200                 205

Leu Val Asn Asn Met Asp Ile Asp Val Ile Leu Gly Gly Gly Arg Met
            210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
            275                 280                 285

Glu Pro Ala Asp Met Lys Tyr Asn Val Gln Gln Asp Pro Thr Lys Asp
            290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
            355                 360                 365

Thr Leu Ile Leu Ala Thr Ala Asp His Ser His Val Phe Ser Phe Gly
            370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Gly Leu Arg Pro Asp Val Asn Asp Ser Ile
            420                 425                 430

Ser Glu Asp Pro Ser Tyr Arg Gln Gln Ala Ala Val Pro Leu Ser Ser
            435                 440                 445

Glu Ser His Gly Gly Glu Asp Val Ala Val Phe Ala Arg Gly Pro Gln
            450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
                485                 490                 495

Ala Pro Ser Gly Leu Ser Asp Ala Ala His Leu Ala
            500                 505

<210> SEQ ID NO 8
<211> LENGTH: 754
<212> TYPE: PRT
<213> ORGANISM: Artificial Sequence
<220> FEATURE:
<223> OTHER INFORMATION: Synthetic polymer.

<400> SEQUENCE: 8

Met Gln Gly Ala Cys Val Leu Leu Leu Leu Gly Leu His Leu Gln Leu
1               5                   10                  15

Ser Leu Gly Leu Ile Pro Ala Glu Glu Glu Asn Pro Ala Phe Trp Asn
            20                  25                  30

-continued

```
Arg Gln Ala Ala Gln Ala Leu Asp Val Ala Lys Lys Leu Gln Pro Ile
        35              40              45
Gln Thr Ala Ala Lys Asn Val Ile Leu Phe Leu Gly Asp Gly Met Gly
    50              55              60
Val Pro Thr Val Thr Ala Thr Arg Ile Leu Lys Gly Gln Met Asn Gly
65              70              75              80
Lys Leu Gly Pro Glu Thr Pro Leu Ala Met Asp Gln Phe Pro Tyr Val
                85              90              95
Ala Leu Ser Lys Thr Tyr Asn Val Asp Arg Gln Val Pro Asp Ser Ala
            100             105             110
Gly Thr Ala Thr Ala Tyr Leu Cys Gly Val Lys Gly Asn Tyr Arg Thr
            115             120             125
Ile Gly Val Ser Ala Ala Ala Arg Tyr Asn Gln Cys Asn Thr Thr Arg
    130             135             140
Gly Asn Glu Val Thr Ser Val Ile Asn Arg Ala Lys Lys Ala Gly Lys
145             150             155             160
Ala Val Gly Val Val Thr Thr Thr Arg Val Gln His Ala Ser Pro Ala
                165             170             175
Gly Ala Tyr Ala His Thr Val Asn Arg Asn Trp Tyr Ser Asp Ala Asp
            180             185             190
Leu Pro Ala Asp Ala Gln Lys Asn Gly Cys Gln Asp Ile Ala Ala Gln
            195             200             205
Leu Val Tyr Asn Met Asp Ile Asp Val Ile Leu Gly Gly Gly Arg Met
    210             215             220
Tyr Met Phe Pro Glu Gly Thr Pro Asp Pro Glu Tyr Pro Asp Asp Ala
225             230             235             240
Ser Val Asn Gly Val Arg Lys Asp Lys Gln Asn Leu Val Gln Glu Trp
                245             250             255
Gln Ala Lys His Gln Gly Ala Gln Tyr Val Trp Asn Arg Thr Ala Leu
            260             265             270
Leu Gln Ala Ala Asp Asp Ser Ser Val Thr His Leu Met Gly Leu Phe
            275             280             285
Glu Pro Ala Asp Met Lys Tyr Asn Val Gln Gln Asp His Thr Lys Asp
    290             295             300
Pro Thr Leu Ala Glu Met Thr Glu Ala Ala Leu Gln Val Leu Ser Arg
305             310             315             320
Asn Pro Arg Gly Phe Tyr Leu Phe Val Glu Gly Gly Arg Ile Asp His
                325             330             335
Gly His His Asp Gly Lys Ala Tyr Met Ala Leu Thr Glu Ala Ile Met
            340             345             350
Phe Asp Asn Ala Ile Ala Lys Ala Asn Glu Leu Thr Ser Glu Leu Asp
            355             360             365
Thr Leu Ile Leu Val Thr Ala Asp His Ser His Val Phe Ser Phe Gly
    370             375             380
Gly Tyr Thr Leu Arg Gly Thr Ser Ile Phe Gly Leu Ala Pro Gly Lys
385             390             395             400
Ala Leu Asp Ser Lys Ser Tyr Thr Ser Ile Leu Tyr Gly Asn Gly Pro
                405             410             415
Gly Tyr Ala Leu Gly Gly Gly Ser Arg Pro Asp Val Asn Gly Ser Thr
            420             425             430
Ser Glu Glu Pro Ser Tyr Arg Gln Gln Ala Ala Val Pro Leu Ala Ser
            435             440             445
Glu Thr His Gly Gly Glu Asp Val Ala Val Phe Ala Arg Gly Pro Gln
```

-continued

```
           450             455             460

Ala His Leu Val His Gly Val Gln Glu Glu Thr Phe Val Ala His Ile
465             470             475             480

Met Ala Phe Ala Gly Cys Val Glu Pro Tyr Thr Asp Cys Asn Leu Pro
            485             490             495

Ala Pro Ala Thr Ala Thr Ser Ile Pro Asp Gly Gly Ser Gly Gly Ser
            500             505             510

Gly Gly Gly Gly Ser Gly Gly Gly Ser Glu Pro Lys Ser Cys Asp
            515             520             525

Lys Thr His Thr Cys Pro Pro Cys Pro Ala Pro Glu Leu Leu Gly Gly
            530             535             540

Pro Ser Val Phe Leu Phe Pro Pro Lys Pro Lys Asp Thr Leu Met Ile
545             550             555             560

Ser Arg Thr Pro Glu Val Thr Cys Val Val Val Asp Val Ser His Glu
            565             570             575

Asp Pro Gln Val Lys Phe Asn Trp Tyr Val Asp Gly Val Gln Val His
            580             585             590

Asn Ala Lys Thr Lys Pro Arg Glu Gln Gln Tyr Asn Ser Thr Tyr Arg
            595             600             605

Val Val Ser Val Leu Thr Val Leu His Gln Asn Trp Leu Asp Gly Lys
            610             615             620

Glu Tyr Lys Cys Lys Val Ser Asn Lys Ala Leu Pro Ala Pro Ile Glu
625             630             635             640

Lys Thr Ile Ser Lys Ala Lys Gly Gln Pro Arg Glu Pro Gln Val Tyr
            645             650             655

Thr Leu Pro Pro Ser Arg Glu Glu Met Thr Lys Asn Gln Val Ser Leu
            660             665             670

Thr Cys Leu Val Lys Gly Phe Tyr Pro Ser Asp Ile Ala Val Glu Trp
            675             680             685

Glu Ser Asn Gly Gln Pro Glu Asn Asn Tyr Lys Thr Thr Pro Pro Val
            690             695             700

Leu Asp Ser Asp Gly Ser Phe Phe Leu Tyr Ser Lys Leu Thr Val Asp
705             710             715             720

Lys Ser Arg Trp Gln Gln Gly Asn Val Phe Ser Cys Ser Val Met His
            725             730             735

Glu Ala Leu His Asn His Tyr Thr Gln Lys Ser Leu Ser Leu Ser Pro
            740             745             750

Gly Lys

<210> SEQ ID NO 9
<211> LENGTH: 751
<212> TYPE: PRT
<213> ORGANISM: Artificial Sequence
<220> FEATURE:
<223> OTHER INFORMATION: Synthetic polymer.

<400> SEQUENCE: 9

Met Gln Trp Ala Cys Val Leu Leu Leu Leu Gly Leu Trp Leu Gln Leu
1               5               10              15

Ser Leu Thr Phe Ile Pro Ala Glu Glu Glu Asp Pro Ala Phe Trp Asn
            20              25              30

Arg Gln Ala Ala Gln Ala Leu Asp Val Ala Lys Lys Leu Gln Pro Ile
        35              40              45

Gln Thr Ala Ala Lys Asn Val Ile Leu Phe Leu Gly Asp Gly Met Gly
        50              55              60
```

```
Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
            115                 120                 125

Ile Gly Val Ser Ala Ala Arg Tyr Asn Gln Cys Asn Thr Thr Ser
        130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Gly Arg Met
        210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
        290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
            325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
        355                 360                 365

Thr Leu Ile Leu Ala Thr Ala Asp His Ser His Val Phe Ser Phe Gly
        370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
            405                 410                 415

Gly Tyr Val Leu Gly Gly Gly Leu Arg Pro Asp Val Asn Asp Ser Ile
            420                 425                 430

Ser Glu Asp Pro Ser Tyr Arg Gln Gln Ala Ala Val Pro Leu Ser Ser
        435                 440                 445

Glu Ser His Gly Gly Glu Asp Val Ala Val Phe Ala Arg Gly Pro Gln
        450                 455                 460

Ala His Leu Val His Gly Val Gln Glu Glu Thr Phe Val Ala His Val
465                 470                 475                 480
```

-continued

```
Met Ala Phe Ala Gly Cys Val Glu Pro Tyr Thr Asp Cys Asn Leu Pro
             485                 490                 495

Ala Pro Ser Gly Leu Ser Asp Gly Gly Ser Gly Gly Ser Gly Gly Gly
             500                 505                 510

Gly Ser Gly Gly Gly Gly Ser Glu Pro Lys Ser Cys Asp Lys Thr His
             515                 520                 525

Thr Cys Pro Pro Cys Pro Ala Pro Glu Leu Leu Gly Gly Pro Ser Val
             530                 535                 540

Phe Leu Phe Pro Pro Lys Pro Lys Asp Thr Leu Met Ile Ser Arg Thr
545                 550                 555                 560

Pro Glu Val Thr Cys Val Val Val Asp Val Ser His Glu Asp Pro Gln
             565                 570                 575

Val Lys Phe Asn Trp Tyr Val Asp Gly Val Gln Val His Asn Ala Lys
             580                 585                 590

Thr Lys Pro Arg Glu Gln Gln Tyr Asn Ser Thr Tyr Arg Val Val Ser
             595                 600                 605

Val Leu Thr Val Leu His Gln Asn Trp Leu Asp Gly Lys Glu Tyr Lys
             610                 615                 620

Cys Lys Val Ser Asn Lys Ala Leu Pro Ala Pro Ile Glu Lys Thr Ile
625                 630                 635                 640

Ser Lys Ala Lys Gly Gln Pro Arg Glu Pro Gln Val Tyr Thr Leu Pro
             645                 650                 655

Pro Ser Arg Glu Glu Met Thr Lys Asn Gln Val Ser Leu Thr Cys Leu
             660                 665                 670

Val Lys Gly Phe Tyr Pro Ser Asp Ile Ala Val Glu Trp Glu Ser Asn
             675                 680                 685

Gly Gln Pro Glu Asn Asn Tyr Lys Thr Thr Pro Pro Val Leu Asp Ser
             690                 695                 700

Asp Gly Ser Phe Phe Leu Tyr Ser Lys Leu Thr Val Asp Lys Ser Arg
705                 710                 715                 720

Trp Gln Gln Gly Asn Val Phe Ser Cys Ser Val Met His Glu Ala Leu
             725                 730                 735

His Asn His Tyr Thr Gln Lys Ser Leu Ser Leu Ser Pro Gly Lys
             740                 745                 750

<210> SEQ ID NO 10
<211> LENGTH: 539
<212> TYPE: PRT
<213> ORGANISM: Artificial Sequence
<220> FEATURE:
<223> OTHER INFORMATION: Synthetic polymer.

<400> SEQUENCE: 10

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
             20                  25                  30

Arg Gln Ala Ala Gln Ala Leu Asp Val Ala Lys Lys Leu Gln Pro Ile
             35                  40                  45

Gln Thr Ala Ala Lys Asn Val Ile Leu Phe Leu Gly Asp Gly Met Gly
             50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
             85                  90                  95
```

-continued

```
Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
            115                 120                 125

Ile Gly Val Ser Ala Ala Ala Arg Tyr Asn Gln Cys Asn Thr Thr Ser
    130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
            195                 200                 205

Leu Val Asn Asn Met Asp Ile Asp Val Ile Leu Gly Gly Gly Arg Met
    210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
            275                 280                 285

Glu Pro Ala Asp Met Lys Tyr Asn Val Gln Gln Asp Pro Thr Lys Asp
    290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
            355                 360                 365

Thr Leu Ile Leu Ala Thr Ala Asp His Ser His Val Phe Ser Phe Gly
    370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Gly Leu Arg Pro Asp Val Asn Asp Ser Ile
            420                 425                 430

Ser Glu Asp Pro Ser Tyr Arg Gln Gln Ala Ala Val Pro Leu Ser Ser
            435                 440                 445

Glu Ser His Gly Gly Glu Asp Val Ala Val Phe Ala Arg Gly Pro Gln
    450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Glu
                485                 490                 495

Val Leu Phe Gln Gly Pro Ala Pro Pro Ala Gly Thr Thr Asp Ala Ala
                500                 505                 510

His Pro Gly Arg Ser Val Val Pro Ala Leu Leu Pro Leu Arg Ala Gly
```

-continued

```
              515                 520                 525

Thr Leu Leu Leu Leu Glu Thr Ala Thr Ala Pro
    530                 535

<210> SEQ ID NO 11
<211> LENGTH: 534
<212> TYPE: PRT
<213> ORGANISM: Artificial Sequence
<220> FEATURE:
<223> OTHER INFORMATION: Synthetic polymer.

<400> SEQUENCE: 11

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Ala Arg Tyr Asn Gln Cys Asn Thr Thr Ser
    130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Gly Arg Met
    210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
    290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                325                 330                 335

Gly His His Glu Gly Lys Ala Tyr Met Ala Leu Thr Asp Thr Val Met
```

-continued

```
                340                 345                 350

Phe Asp Asn Ala Ile Ala Lys Ala Asn Glu Leu Thr Ser Glu Leu Asp
        355                 360                 365

Thr Leu Ile Leu Ala Thr Ala Asp His Ser His Val Phe Ser Phe Gly
    370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Gly Leu Arg Pro Asp Val Asn Asp Ser Ile
                420                 425                 430

Ser Glu Asp Pro Ser Tyr Arg Gln Gln Ala Ala Val Pro Leu Ser Ser
        435                 440                 445

Glu Ser His Gly Gly Glu Asp Val Ala Val Phe Ala Arg Gly Pro Gln
        450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Ala
                485                 490                 495

Pro Pro Ala Gly Thr Thr Asp Ala Ala His Pro Ile Glu Gly Arg Ser
                500                 505                 510

Val Val Pro Ala Leu Leu Pro Leu Arg Ala Gly Thr Leu Leu Leu Leu
                515                 520                 525

Glu Thr Ala Thr Ala Pro
        530
```

```
<210> SEQ ID NO 12
<211> LENGTH: 1669
<212> TYPE: DNA
<213> ORGANISM: Artificial Sequence
<220> FEATURE:
<223> OTHER INFORMATION: Synthetic polymer.

<400> SEQUENCE: 12
atgcaggggc cctgggtgct gctgctgctg ggcctgaggc tacagctctc cctgggcgtc      60
atcccaggta atgaggctcc ccaagctgtt ccacacacag ggcacccct  cagccaggct     120 gacctgatct ctactctccc cctggccagc tgaggaggag aaccccggcct tctggaaccg     180 ccaggcagct gaggccctgg atgctgccaa gaagctgcag cccatccaga aggtcgccaa     240
gaacctcatc ctcttcctgg cgatgggtt  ggggtgccc  acggtgacag ccaccaggat     300
cctaaagggg cagaagaatg gcaaactggg gcctgagacg ccctggcca  tggaccgctt     360 cccatacctg gctctgtcca agacatacaa tgtggacaga caggtgccag acagcgcagc     420
cacagccacg gcctacctgt gcgggtcaa  ggccaacttc cagaccatcg gcttgagtgc     480
agccgcccgc tttaaccagt gcaacacgac acgcggcaat gaggtcatct ccgtgatgaa     540
ccgggccaag caagcaggaa agtcagtagg agtggtgacc accacacggg tgcagcacgc     600
ctcgccagcc ggcacctacg cacacacagt gaaccgcaac tggtactcag atgctgacat     660
gcctgcctca gcccgccagg aggggtgcca ggacatcgcc actcagctca tctccaacat     720
ggacattgac gtgatccttg cgggaggccg caagtacatg tttcccatgg gaccccaga      780 ccctgagtac ccagctgatg ccagccagaa tggaatcagg ctggacggga agaacctggt     840
gcaggaatgg ctggcaaagc accagggtgc ctggtatgtg tggaaccgca ctgagctcat     900
gcaggcgtcc ctggaccagt ctgtgaccca tctcatgggc ctctttgagc ccggagacac     960
```

-continued

```
gaaatatgag atccaccgag accccacact ggacccctcc ctgatggaga tgacagaggc      1020
tgccctgcgc ctgctgagca ggaacccccg cggcttctac ctctttgtgg agggcggccg      1080
catcgaccat ggtcatcatg agggtgtggc ttaccaggca ctcactgagg cggtcatgtt      1140
cgacgacgcc attgagaggg cgggccagct caccagcgag gaggacacgc tgaccctcgt      1200
caccgctgac cactcccatg tcttctcctt tggtggctac accttgcgag ggagctccat      1260
cttcgggttg gcccccagca aggctcagga cagcaaagcc tacacgtcca tcctgtacgg      1320
caatggcccg ggctacgtgt tcaactcagg cgtgcgacca gacgtgaatg agagcgagag      1380
cgggagcccc gattaccagc agcaggcggc ggtgcccctg tcgtccgaga cccacggagg      1440
cgaagacgtg gcggtgtttg cgcgcggccc gcaggcgcac ctggtgcatg gtgtgcagga      1500
gcagagcttc gtagcgcatg tcatggcctt cgctgcctgt ctggagccct acacggcctg      1560
cgacctggcg cctcccgcct gcaccaccga cgccgcgcac ccagttgccg cgtcgctgcc      1620
actgctggcc gggaccctgc tgctgctggg ggcgtccgct gctccctga                  1669
```

<210> SEQ ID NO 13
<211> LENGTH: 1671
<212> TYPE: DNA
<213> ORGANISM: Artificial Sequence
<220> FEATURE:
<223> OTHER INFORMATION: Synthetic polymer.

<400> SEQUENCE: 13

```
atgcaggggc cctgggtgct gctgctgctg ggcctgaggc tacagctctc cctgggcgtc        60
atcccagctg aggaggagaa cccggccttc tggaaccgcc aggcagctga ggccctggat       120
gctgccaaga agctgcagcc catccagaag gtcgccaaga acctcatcct cttcctgggc       180
gatgggttgg gggtgcccac ggtgacagcc accaggatcc taaaggggca gaagaatggc       240
aaactggggc ctgagacgcc cctggccatg gaccgcttcc catacctggc tctgtccaag       300
acatacaatg tggacagaca ggtgccagac agcgcagcca cagccacggc ctacctgtgc       360
ggggtcaagg ccaacttcca gaccatcggc ttgagtgcag ccgcccgctt taaccagtgc       420
aacacgacac gcggcaatga ggtcatctcc gtgatgaacc gggccaagca agcaggaaag       480
tcagtaggag tggtgaccac cacacgggtg cagcacgcct cgccagccgg cacctacgca       540
cacacagtga accgcaactg gtactcagat gctgacatgc ctgcctcagc ccgccaggag       600
gggtgccagg acatcgccac tcagctcatc tccaacatgg acattgacgt gatccttggc       660
ggaggccgca agtacatgtt tcccatgggg accccagacc ctgagtaccc agctgatgcc       720
agccagaatg gaatcaggct ggacgggaag aacctggtgc aggaatggct ggcaaagcac       780
cagggtgcct ggtatgtgtg aaccgcact gagctcatgc aggcgtccct ggaccagtct       840
gtgacccatc tcatgggcct ctttgagccc ggagacacga aatatgagat ccaccgagac       900
cccacactgg accctccct gatggagatg acagaggctg ccctgcgcct gctgagcagg       960 aaccccgcg gcttctacct ctttgtggag ggcggccgca tcgaccatgg tcatcatgag      1020
ggtgtggctt accaggcact cactgaggcg gtcatgttcg acgacgccat tgagagggcg      1080
ggccagctca ccagcgagga ggacacgctg accctcgtca ccgctgacca ctcccatgtc      1140
ttctcctttg gtggctacac cttgcgaggg agctccatct tcgggttggc ccccagcaag      1200
gctcaggaca gcaaagccta cacgtccatc ctgtacggca atggcccggg ctacgtgttc      1260
aactcaggcg tgcgaccaga cgtgaatgag agcgagagcg ggagccccga ttaccagcag      1320
```

-continued

```
caggcggcgg tgcccctgtc gtccgagacc cacggaggcg aagacgtggc ggtgtttgcg      1380
cgcggcccgc aggcgcacct ggtgcatggt gtgcaggagc agagcttcgt agcgcatgtc      1440
atggccttcg ctgcctgtct ggagccctac acggcctgcg acctggcgcc tcccgcctgc      1500
accaccgacg ccgcgcaccc agttgccgcg tcgctgccac tgctggccgg gaccctgctg      1560
ctgctggggg cgtccgctgc tccctgattt actaaaacct tgaaataaaa ttgtaaaaca      1620
tcagtttgaa ggcctgactc tcagggtagt tctttttttaa ttctgggttt t             1671

<210> SEQ ID NO 14
<211> LENGTH: 1672
<212> TYPE: DNA
<213> ORGANISM: Artificial Sequence
<220> FEATURE:
<223> OTHER INFORMATION: Synthetic polymer.

<400> SEQUENCE: 14
atgcagtggg cctgtgtgct gctgctgctg ggcctgtggc tacagctctc cctcaccttc       60
atcccaggta atcaggcggc tcccagcagc ccctactcac aggggcggct ctaggctgac      120
ctgaccaaca ctctcccctt gggcagctga ggaggaagac cccgccttct ggaaccgcca      180
ggcagcccag gcccttgatg tagccaagaa gttgcagccg atccagacag ctgccaagaa      240
tgtcatcctc ttcttggggg atgggatggg ggtgcctacg gtgacagcca ctcggatcct      300
aaaggggcag atgaatggta agctgggacc tgagacaccc ctggccatgg accagttccc      360
atacgtggct ctgtccaaga catacaacgt ggacagacag gtgccagaca gcgcaggcac      420
tgccactgcc tacctgtgtg gggtcaaggg caactacaaa accattggtg taagtgcagc      480
cgcccgctac aaccagtgca acacaacaag tggcaatgag gtcacgtctg tgatgaaccg      540
ggccaagaaa gcaggaaagt cagtgggagt ggtgaccacc tccagggtgc agcatgcctc      600
cccagccggt gcttatgcac acacggtgaa ccgaaactgg tactcagatg ccgacctgcc      660
tgccgatgca cagacgtatg gctgccagga catcgccaca caactggtca acaacatgga      720
tattgacgtg atcctgggtg gaggccgaat gtacatgttt cctgagggga ccccggatcc      780
tgaataccca tacgatgtca atcagactgg agtccggaag gacaagcgga atctggtgca      840
ggagtggcag gccaagcacc agggagccca gtatgtgtgg aaccgcacgg agctccttca      900
ggcagccaat gaccccagtg taacacacct catgggcctc tttgagccgg cagacatgaa      960
gtataatgtt cagcaagacc ccaccaagga cccgaccctg gaggagatga cggaggcggc     1020
cctgcaagtg ctgagcagga accccaggg cttctacctc ttcgtggagg gaggccgcat     1080
tgaccacggt caccatgaag gcaaagctta tatggcactg actgatacag tcatgtttga     1140
caatgccatc gccaaggcta acgagctcac tagcgaactg gacacgctga tccttgccac     1200
tgcagaccac tcccatgtct tctcttttgg tggctacaca ctgcgtggga cctccatttt     1260
cggtctggcc cccagcaagg cctcagacaa caagtcctac acctccatcc tctatggcaa     1320
tggccctggc tacgtgcttg gtgggggctt aaggcccgat gttaatgaca gcataagcga     1380
ggacccctcg taccggcagc aggcggccgt gccctgtct agtgagtccc acgggggcga     1440
ggacgtggcg gtgttcgcgc gaggcccgca ggcgcacctg gtgcacggcg tgcaggagga     1500
gaccttcgtg gcgcacgtca tggcctttgc gggctgcgtg gagccctaca ccgactgcaa     1560
tctgccggcc ccctctggcc tctccgacgc cgcgcacctg gcggccagcc cgccttcgct     1620
ggcgctgctg gccggggcga tgctgctgct gctggcgcct gccttgtact ga             1672
```

-continued

<210> SEQ ID NO 15
<211> LENGTH: 1869
<212> TYPE: DNA
<213> ORGANISM: Artificial Sequence
<220> FEATURE:
<223> OTHER INFORMATION: Synthetic polymer.

<400> SEQUENCE: 15
atgcagtggg cctgtgtgct gctgctgctg ggcctgtggc tacagctctc cctcaccttc        60
atcccagctg aggaggaaga ccccgccttc tggaaccgcc aggcagccca ggcccttgat       120
gtagccaaga agttgcagcc gatccagaca gctgccaaga atgtcatcct cttcttgggg       180
gatgggatgg gggtgcctac ggtgacagcc actcggatcc taaagggggca gatgaatggt      240 aagctgggac ctgagacacc cctggccatg gaccagttcc catacgtggc tctgtccaag       300
acatacaacg tggacagaca ggtgccgac agcgcaggca ctgccactgc ctacctgtgt        360
ggggtcaagg gcaactacaa aaccattggt gtaagtgcag ccgcccgcta caaccagtgc       420
aacacaacaa gtggcaatga ggtcacgtct gtgatgaacc gggccaagaa agcaggaaag       480
tcagtgggag tggtgaccac ctccaggggtg cagcatgcct ccccagccgg tgcttatgca      540
cacacggtga accgaaactg gtactcagat gccgacctgc ctgccgatgc acagacgtat       600
ggctgccagg acatcgccac acaactggtc aacaacatgg atattgacgt gatcctgggt       660
ggaggccgaa tgtacatgtt tcctgagggg accccggatc ctgaataccc atacgatgtc       720
aatcagactg gagtccggaa ggacaagcgg aatctggtgc aggagtggca ggccaagcac       780
cagggagccc agtatgtgtg gaaccgcacg gagctccttc aggcagccaa tgaccccagt       840
gtaacacacc tcatgggcct ctttgagccg gcagacatga agtataatgt tcagcaagac      900
cccaccaagg acccgaccct ggaggagatg acggaggcgg ccctgcaagt gctgagcagg       960
aacccccagg gcttctacct cttcgtggag ggaggccgca ttgaccacgg tcaccatgaa      1020
ggcaaagctt atatggcact gactgataca gtcatgtttg acaatgccat cgccaaggct      1080
aacgagctca ctagcgaact ggacacgctg atccttgcca ctgcagacca ctcccatgtc      1140
ttctcttttg gtggctacac actgcgtggg acctccattt tcggtctggc ccccagcaag      1200
gcctcagaca acaagtccta cacctccatc tctatggcaa atggccctgg ctacgtgctt      1260
ggtgggggct taaggcccga tgttaatgac agcataagcg aggacccctc gtaccggcag      1320
caggcggccg tgcccctgtc tagtgagtcc cacgggggcg aggacgtggc ggtgttcgcg      1380
cgaggcccgc aggcgcacct ggtgcacggc gtgcaggagg agaccttcgt ggcgcacgtc      1440
atggcctttg cgggctgcgt ggagccctac accgactgca atctgccggc ccctctggc      1500 ctctccgacg ccgcgcacct ggcggccagc ccgccttcgc tggcgctgct ggccggggcg      1560
atgctgctgc tgctggcgcc tgccttgtac tgaggggacc cggggggtggg gacacaggcc     1620 ccgcctccc tgggaggcag gaagcagctc tcaaataaac tgttctaagt atgatacagg       1680
agtgatacat gtgtgaagag aagcccttag gtgggggcac agagtgtctg ggtgaggggg      1740
gtcagggtca catcaggagg ttagggaggg gttgatgaag ggctgacgtt gagcaaagac      1800
caaaggcaac tcagaaggac agtggtgcag gactgggtgt ggtcagcagg gggactggtt      1860
ggggggatcc                                                           1869

<210> SEQ ID NO 16
<211> LENGTH: 1259
<212> TYPE: DNA
<213> ORGANISM: Artificial Sequence
<220> FEATURE:

<223> OTHER INFORMATION: Synthetic polymer.

<400> SEQUENCE: 16

```
aaaaaacaag acaaagctga gatcagaaat gtcattgtga tgataggcga cggcatgggg       60
acgccttaca taagagccta ccgttccatg aaaaataacg gtgacacacc gaataacccg      120
aagttaacag aatttgaccg gaacctgaca ggcatgatga tgacgcatcc ggatgaccct      180
gactataata ttacagattc agcagcagcc ggaacagcat tagcgacagg cgttaagaca      240
tataacaatg caattggcgt cgataaaaac ggaaaaaaag tgaaatctgt acttgaagag      300
gccaaacagc aaggcaagtc aacagggctt gtcgccacgt ctgaaattaa ccacgccact      360
ccagccgcat atggcgccca caatgaatca cggaaaaaca tggaccaaat cgccaacagc      420
tatatggatg acaagataaa aggcaaacat aaaatagacg tgctgctcgg cggcggaaaa      480
tcttatttta accgcaagaa cagaaacttg acaaggaat tcaaacaagc cggctacagc      540
tatgtgacaa ctaaacaagc attgaaaaaa aataaagatc agcaggtgct cgggctttc      600 gcagatggag ggcttgctaa agcgctcgac cgtgacagta aaacaccgtc tctcaaagac      660
atgacggttt cagcaattga tcgcctgaac caaaataaaa aaggattttt cttgatggtc      720
gaagggagcc agattgactg ggcggccat gacaatgata cagtaggagc catgagcgag      780
gttaaagatt ttgaacaggc ctataaagcc gcgattgaat ttgcgaaaaa agacaaacat      840
acacttgtga ttgcaactgc tgaccataca accggcggct ttaccattgg cgcaaacggg      900
gaaaagaatt ggcacgcaga accgattctc tccgctaaga aaacacctga attcatggcc      960
aaaaaaatca ggaaggcaag ccggttaaag atgtgctcgc ccgctatgcc aatctgaaag     1020
tcacatctga agaaatcaaa agcgttgaag cagctgcaca ggctgacaaa agcaaagggg     1080
cctccaaagc catcatcaag attttaata cccgctccaa cagcggatgg acgagtaccg     1140
atcataccgg cgaagaagta ccggtatacg cgtacggccc cggaaaagaa aaattccgcg     1200
gattgattaa caatacggac caggcaaaca tcatatttaa gattttaaaa actggaaaa     1259
```

<210> SEQ ID NO 17
<211> LENGTH: 420
<212> TYPE: PRT
<213> ORGANISM: Artificial Sequence
<220> FEATURE:
<223> OTHER INFORMATION: Synthetic polymer.

<400> SEQUENCE: 17

```
Lys Lys Gln Asp Lys Ala Glu Ile Arg Asn Val Ile Val Met Ile Gly
1               5                   10                  15

Asp Gly Met Gly Thr Pro Tyr Ile Arg Ala Tyr Arg Ser Met Lys Asn
            20                  25                  30

Asn Gly Asp Thr Pro Asn Asn Pro Lys Leu Thr Glu Phe Asp Arg Asn
        35                  40                  45

Leu Thr Gly Met Met Met Thr His Pro Asp Asp Pro Asp Tyr Asn Ile
    50                  55                  60

Thr Asp Ser Ala Ala Ala Gly Thr Ala Leu Ala Thr Gly Val Lys Thr
65                  70                  75                  80

Tyr Asn Asn Ala Ile Gly Val Asp Lys Asn Gly Lys Lys Val Lys Ser
                85                  90                  95

Val Leu Glu Glu Ala Lys Gln Gln Gly Lys Ser Thr Gly Leu Val Ala
            100                 105                 110

Thr Ser Glu Ile Asn His Ala Thr Pro Ala Ala Tyr Gly Ala His Asn
            115                 120                 125
```

```
Glu Ser Arg Lys Asn Met Asp Gln Ile Ala Asn Ser Tyr Met Asp Asp
    130                 135                 140

Lys Ile Lys Gly Lys His Lys Ile Asp Val Leu Leu Gly Gly Gly Lys
145                 150                 155                 160

Ser Tyr Phe Asn Arg Lys Asn Arg Asn Leu Thr Lys Glu Phe Lys Gln
                165                 170                 175

Ala Gly Tyr Ser Tyr Val Thr Thr Lys Gln Ala Leu Lys Lys Asn Lys
                180                 185                 190

Asp Gln Gln Val Leu Gly Leu Phe Ala Asp Gly Gly Leu Ala Lys Ala
        195                 200                 205

Leu Asp Arg Asp Ser Lys Thr Pro Ser Leu Lys Asp Met Thr Val Ser
    210                 215                 220

Ala Ile Asp Arg Leu Asn Gln Asn Lys Lys Gly Phe Phe Leu Met Val
225                 230                 235                 240

Glu Gly Ser Gln Ile Asp Trp Ala Ala His Asp Asn Asp Thr Val Gly
                245                 250                 255

Ala Met Ser Glu Val Lys Asp Phe Glu Gln Ala Tyr Lys Ala Ala Ile
                260                 265                 270

Glu Phe Ala Lys Lys Asp Lys His Thr Leu Val Ile Ala Thr Ala Asp
        275                 280                 285

His Thr Thr Gly Gly Phe Thr Ile Gly Ala Asn Gly Glu Lys Asn Trp
    290                 295                 300

His Ala Glu Pro Ile Leu Ser Ala Lys Lys Thr Pro Glu Phe Met Ala
305                 310                 315                 320

Lys Lys Ile Ser Glu Gly Lys Pro Val Lys Asp Val Leu Ala Arg Tyr
                325                 330                 335

Ala Asn Leu Lys Val Thr Ser Glu Glu Ile Lys Ser Val Glu Ala Ala
                340                 345                 350

Ala Gln Ala Asp Lys Ser Lys Gly Ala Ser Lys Ala Ile Ile Lys Ile
        355                 360                 365

Phe Asn Thr Arg Ser Asn Ser Gly Trp Thr Ser Thr Asp His Thr Gly
    370                 375                 380

Glu Glu Val Pro Val Tyr Ala Tyr Gly Pro Gly Lys Glu Lys Phe Arg
385                 390                 395                 400

Gly Leu Ile Asn Asn Thr Asp Gln Ala Asn Ile Ile Phe Lys Ile Leu
                405                 410                 415

Lys Thr Gly Lys
            420
```

```
<210> SEQ ID NO 18
<211> LENGTH: 16
<212> TYPE: PRT
<213> ORGANISM: Artificial Sequence
<220> FEATURE:
<223> OTHER INFORMATION: Synthetic polymer.

<400> SEQUENCE: 18

Gly Gly Ser Gly Gly Ser Gly Gly Gly Gly Ser Gly Gly Gly Gly Ser
1               5                   10                  15

<210> SEQ ID NO 19
<211> LENGTH: 5
<212> TYPE: PRT
<213> ORGANISM: Artificial Sequence
<220> FEATURE:
<223> OTHER INFORMATION: Synthetic polymer.
```

<400> SEQUENCE: 19

Gly Gly Gly Gly Ser
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 20

Gly Gly Gly Gly Ser Gly Gly Gly Gly Ser
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Synthetic polymer.

<400> SEQUENCE: 21

Gly Gly Gly Gly Ser Gly Gly Gly Gly Ser Gly Gly Gly Gly Ser
1               5                   10                  15

<210> SEQ ID NO 22
<211> LENGTH: 20
<212> TYPE: PRT
<213> ORGANISM: Artificial Sequence
<220> FEATURE:
<223> OTHER INFORMATION: Synthetic polymer.

<400> SEQUENCE: 22

Gly Gly Gly Gly Ser Gly Gly Gly Gly Ser Gly Gly Gly Gly Ser Gly
1               5                   10                  15

Gly Gly Gly Ser
            20

<210> SEQ ID NO 23
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 23

Gly Gly Gly Gly Gly Gly Gly Gly
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic polymer.

<400> SEQUENCE: 24

Gly Gly Gly Gly Gly Gly
1               5

<210> SEQ ID NO 25
<211> LENGTH: 5
<212> TYPE: PRT
<213> ORGANISM: Artificial Sequence
<220> FEATURE:

-continued

<223> OTHER INFORMATION: Synthetic polymer.

<400> SEQUENCE: 25

Glu Ala Ala Ala Lys
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 26

Glu Ala Ala Ala Lys Glu Ala Ala Ala Lys
1               5                   10

<210> SEQ ID NO 27
<211> LENGTH: 15
<212> TYPE: PRT
<213> ORGANISM: Artificial Sequence
<220> FEATURE:
<223> OTHER INFORMATION: Synthetic polymer.

<400> SEQUENCE: 27

Glu Ala Ala Ala Lys Glu Ala Ala Ala Lys Glu Ala Ala Ala Lys
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: Synthetic polymer.

<400> SEQUENCE: 28

Ala Glu Ala Ala Ala Lys Glu Ala Ala Ala Lys Ala
1               5                   10

<210> SEQ ID NO 29
<211> LENGTH: 17
<212> TYPE: PRT
<213> ORGANISM: Artificial Sequence
<220> FEATURE:
<223> OTHER INFORMATION: Synthetic polymer.

<400> SEQUENCE: 29

Ala Glu Ala Ala Ala Lys Glu Ala Ala Ala Lys Glu Ala Ala Ala Lys
1               5                   10                  15

Ala

<210> SEQ ID NO 30
<211> LENGTH: 22
<212> TYPE: PRT
<213> ORGANISM: Artificial Sequence
<220> FEATURE:
<223> OTHER INFORMATION: Synthetic polymer.

<400> SEQUENCE: 30

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 31

-continued

```
<211> LENGTH: 27
<212> TYPE: PRT
<213> ORGANISM: Artificial Sequence
<220> FEATURE:
<223> OTHER INFORMATION: Synthetic polymer.

<400> SEQUENCE: 31

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 32
<211> LENGTH: 12
<212> TYPE: PRT
<213> ORGANISM: Artificial Sequence
<220> FEATURE:
<223> OTHER INFORMATION: Synthetic polymer.

<400> SEQUENCE: 32

Ala Glu Ala Ala Ala Lys Glu Ala Ala Ala Lys Ala
1               5                   10

<210> SEQ ID NO 33
<211> LENGTH: 46
<212> TYPE: PRT
<213> ORGANISM: Artificial Sequence
<220> FEATURE:
<223> OTHER INFORMATION: Synthetic polymer.

<400> SEQUENCE: 33

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
            20                  25                  30

Ala Ala Lys Glu Ala Ala Ala Lys Glu Ala Ala Ala Lys Ala
        35                  40                  45

<210> SEQ ID NO 34
<211> LENGTH: 5
<212> TYPE: PRT
<213> ORGANISM: Artificial Sequence
<220> FEATURE:
<223> OTHER INFORMATION: Synthetic polymer.

<400> SEQUENCE: 34

Pro Ala Pro Ala Pro
1               5

<210> SEQ ID NO 35
<211> LENGTH: 18
<212> TYPE: PRT
<213> ORGANISM: Artificial Sequence
<220> FEATURE:
<223> OTHER INFORMATION: Synthetic polymer.

<400> SEQUENCE: 35

Lys Glu Ser Gly Ser Val Ser Ser Glu Gln Leu Ala Gln Phe Arg Ser
1               5                   10                  15

Leu Asp

<210> SEQ ID NO 36
<211> LENGTH: 14
<212> TYPE: PRT
<213> ORGANISM: Artificial Sequence
```

-continued

```
<220> FEATURE:
<223> OTHER INFORMATION: Synthetic polymer.

<400> SEQUENCE: 36

Glu Gly Lys Ser Ser Gly Ser Gly Ser Glu Ser Lys Ser Thr
1               5               10

<210> SEQ ID NO 37
<211> LENGTH: 12
<212> TYPE: PRT
<213> ORGANISM: Artificial Sequence
<220> FEATURE:
<223> OTHER INFORMATION: Synthetic polymer.

<400> SEQUENCE: 37

Gly Ser Ala Gly Ser Ala Ala Gly Ser Gly Glu Phe
1               5               10

<210> SEQ ID NO 38
<211> LENGTH: 13
<212> TYPE: DNA
<213> ORGANISM: Artificial Sequence
<220> FEATURE:
<223> OTHER INFORMATION: Synthetic polymer.

<400> SEQUENCE: 38
gccgccacca tgg                                                              13

<210> SEQ ID NO 39
<211> LENGTH: 487
<212> TYPE: PRT
<213> ORGANISM: Artificial Sequence
<220> FEATURE:
<223> OTHER INFORMATION: Synthetic polymer.

<400> SEQUENCE: 39

Leu Ile Pro Ala Glu Glu Glu Asn Pro Ala Phe Trp Asn Arg Gln Ala
1               5               10              15

Ala Gln Ala Leu Asp Val Ala Lys Lys Leu Gln Pro Ile Gln Thr Ala
            20              25              30

Ala Lys Asn Val Ile Leu Phe Leu Gly Asp Gly Met Gly Val Pro Thr
        35              40              45

Val Thr Ala Thr Arg Ile Leu Lys Gly Gln Met Asn Gly Lys Leu Gly
    50              55              60

Pro Glu Thr Pro Leu Ala Met Asp Gln Phe Pro Tyr Val Ala Leu Ser
65              70              75              80

Lys Thr Tyr Asn Val Asp Arg Gln Val Pro Asp Ser Ala Gly Thr Ala
            85              90              95

Thr Ala Tyr Leu Cys Gly Val Lys Gly Asn Tyr Arg Thr Ile Gly Val
            100             105             110

Ser Ala Ala Ala Arg Tyr Asn Gln Cys Asn Thr Thr Arg Gly Asn Glu
        115             120             125

Val Thr Ser Val Ile Asn Arg Ala Lys Lys Ala Gly Lys Ala Val Gly
        130             135             140

Val Val Thr Thr Thr Arg Val Gln His Ala Ser Pro Ala Gly Ala Tyr
145             150             155             160

Ala His Thr Val Asn Arg Asn Trp Tyr Ser Asp Ala Asp Leu Pro Ala
            165             170             175

Asp Ala Gln Lys Asn Gly Cys Gln Asp Ile Ala Ala Gln Leu Val Tyr
            180             185             190
```

-continued

```
Asn Met Asp Ile Asp Val Ile Leu Gly Gly Gly Arg Met Tyr Met Phe
        195             200             205

Pro Glu Gly Thr Pro Asp Pro Glu Tyr Pro Asp Asp Ala Ser Val Asn
        210             215             220

Gly Val Arg Lys Asp Lys Gln Asn Leu Val Gln Glu Trp Gln Ala Lys
225             230             235             240

His Gln Gly Ala Gln Tyr Val Trp Asn Arg Thr Ala Leu Leu Gln Ala
            245             250             255

Ala Asp Asp Ser Ser Val Thr His Leu Met Gly Leu Phe Glu Pro Ala
            260             265             270

Asp Met Lys Tyr Asn Val Gln Gln Asp His Thr Lys Asp Pro Thr Leu
        275             280             285

Ala Glu Met Thr Glu Ala Ala Leu Gln Val Leu Ser Arg Asn Pro Arg
        290             295             300

Gly Phe Tyr Leu Phe Val Glu Gly Gly Arg Ile Asp His Gly His His
305             310             315             320

Asp Gly Lys Ala Tyr Met Ala Leu Thr Glu Ala Ile Met Phe Asp Asn
            325             330             335

Ala Ile Ala Lys Ala Asn Glu Leu Thr Ser Glu Leu Asp Thr Leu Ile
            340             345             350

Leu Val Thr Ala Asp His Ser His Val Phe Ser Phe Gly Gly Tyr Thr
            355             360             365

Leu Arg Gly Thr Ser Ile Phe Gly Leu Ala Pro Gly Lys Ala Leu Asp
        370             375             380

Ser Lys Ser Tyr Thr Ser Ile Leu Tyr Gly Asn Gly Pro Gly Tyr Ala
385             390             395             400

Leu Gly Gly Gly Ser Arg Pro Asp Val Asn Gly Ser Thr Ser Glu Glu
            405             410             415

Pro Ser Tyr Arg Gln Gln Ala Ala Val Pro Leu Ala Ser Glu Thr His
            420             425             430

Gly Gly Glu Asp Val Ala Val Phe Ala Arg Gly Pro Gln Ala His Leu
        435             440             445

Val His Gly Val Gln Glu Glu Thr Phe Val Ala His Ile Met Ala Phe
        450             455             460

Ala Gly Cys Val Glu Pro Tyr Thr Asp Cys Asn Leu Pro Ala Pro Ala
465             470             475             480

Thr Ala Thr Ser Ile Pro Asp
                485
```

ALKALINE PHOSPHATASE FORMULATIONS AND USES THEREOF

CROSS-REFERENCE TO RELATED APPLICATIONS

This application is a 371 national stage filing of International Application No. PCT/US2020/035814, filed Jun. 3, 2020, which claims the benefit of U.S. Provisional Application No. 62/856,309, filed Jun. 3, 2019, the entire contents of which are hereby incorporated by reference in their entirety.

FIELD OF THE INVENTION

The present invention provides, in part, formulations comprising alkaline phosphatases and uses thereof.

DESCRIPTION OF THE TEXT FILE SUBMITTED ELECTRONICALLY

The content of the text file submitted electronically herewith is incorporated herein by reference in their entirety: A computer readable format copy of the Sequence Listing (Filename: "SYN-044_ST25.txt"; Date created: Dec. 2, 2021; File size: 78.4 KB).

BACKGROUND

Alkaline phosphatases are dimeric metalloenzymes that catalyze the hydrolysis of phosphate esters and dephosphorylate a variety of target substrates at physiological and higher pHs. Alkaline phosphatases (APs) are found in prokaryotic as well as in eukaryotic organisms (e.g., in *E. coli* and mammals). Mammalian APs have been shown to play important roles in gut homeostasis, mucosal barrier function, promotion of commensal bacteria, and defense from pathogens. Mammalian APs exert their properties by primarily targeting lipopolysaccharide (LPS, a toll-like receptor-4 (TLR4) agonist), flagellin (a TLR5 agonist) and CpG DNA (a TLR9 agonist). APs also degrade intestine luminal nucleotide triphosphates (NTPs, e.g., ATP, GTP, etc.), which promote the growth of good bacteria and reverses dysbiosis.

Treatment for gastrointestinal (GI) disorders is increasingly looking to the role of the microbiome as a mediator in preserving healthy functioning of the GI tract. As such, the role of alkaline phosphatases (APs) in promoting growth of good bacteria and reversing dysbiosis is a significant and growing field of study in the advancement of treatment options for GI disorders. Accordingly, APs may find clinical use as, for example, microbiome preserving agents for treating various gastrointestinal (GI) disorders.

However, formulating protein biologics, including APs, is a particularly challenging task given the various considerations that must be taken into account regarding the drug's administration route. Further, providing drug-layered modified-release formulations that are both stable and exhibit sufficient dissolution/release profiles to allow for targeted release to the GI tract can be challenging due to the complicated nature of protein biologics.

Accordingly, there remains a need for novel alkaline phosphatase formulations for use in therapeutic intervention.

SUMMARY OF THE INVENTION

Accordingly, the present invention provides modified-release formulations comprising an alkaline phosphatase (AP)-based agent and/or additional therapeutic agents. In various embodiments, the formulations release a substantial amount of the AP-based agent in the GI tract. In one embodiment, the formulation comprises at least one core particle and a base coat over the core particle, wherein the base coat comprises an AP-based agent. In another embodiment, the formulation comprises at least one core particle, wherein the AP-based agent is encapsulated within the core particle. In various embodiments, the formulation comprises a modified-release coating such as a delayed-release coating disposed over the core particle. In some embodiments, the delayed-release coating is substantially stable in gastric fluid. In some embodiments, the delayed-release coating is substantially stable in intestinal fluid. In an embodiment, the delayed-release coating comprises an EUDRAGIT compound. In various embodiments, the formulation may be in the form of a sucrose pellet. In some embodiments, the pellet includes a plurality of core particles.

These AP-based agents find uses in a number of therapies, including the prevention or treatment of CDI and/or a *C. difficile*-associated disease or other antibiotic-induced adverse effects in the GI tract. AP-based agents of the present invention also find uses in therapies directed to microbiome-associated disorders, included but not limited to, metabolic disorders, neurological disorders, celiac disease, cystic fibrosis, radiation enteropathy, sepsis, and HIV-mediated gut dysbiosis.

For example, the AP-based agents can find use in allowing a patient to undergo antibiotic therapy while being protected against diseases that could result from excess antibiotics negatively affecting the microbiome. Such use does not interfere with the systemic utility of the antibiotic. Rather, without wishing to be bound by theory, the AP-based agents maintain intestinal microbiota, which prevents the disruption of the microbiota that is linked to the various disease states described herein.

DESCRIPTION OF THE FIGURES

FIG. 1 depicts sequences pertaining to alkaline phosphatase-based agents present in formulations described herein.

FIG. 11A-H depicts results of analysis of the non-GMP SYN-020 5 mg and 15 mg capsule dosages.

DETAILED DESCRIPTION OF THE INVENTION

Figure 2:
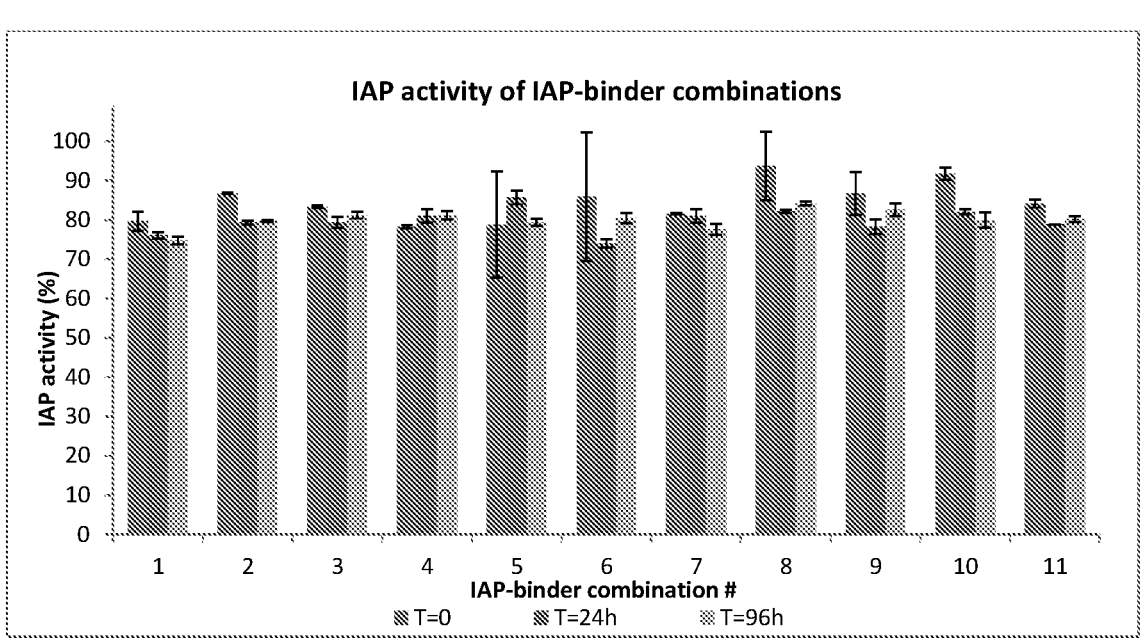
FIG. 2 shows the IAP activity over 96 hours in an IAP-binder evaluation. In each set of histograms, various time-points are presented, where the left-most bar represents 0 hours; the middle bar represents 24 hours; and the right-most bar represents 96 hours.

In various aspects, the present invention provides modi-fied-release formulations comprising an alkaline phos-phatase (AP)-based agent and/or additional therapeutic agents. In various embodiments, the formulations release a substantial amount of the AP-based agent in the GI tract. In one embodiment, the formulation comprises at least one core particle and a base coat over the core particle, wherein the base coat comprises an AP-based agent. In various embodiments, the formulation comprises a modified-release coating such as a delayed-release coating disposed over the core particle. In some embodiments, the delayed-release coating is substantially stable in gastric fluid. In an embodi-ment, the delayed-release coating comprises an EUDRAGIT compound.

Alkaline-Phosphatase-Based Agents

The present invention is directed, in part, to pharmaceu-tical compositions, formulations, and uses of one or more alkaline phosphatase-based agents (AP-based agents). Illus-trative AP-based agents that may be utilized in the present invention include, but are not limited to, intestinal alkaline phosphatase (IAP; e.g., human IAP, calf IAP or bovine IAP, chicken IAP, goat IAP), bovine intestinal alkaline phos-phatase (bIAP), recombinant bovine intestinal alkaline phos-phatase (rbIAP), placental alkaline phosphatase (PLAP), placental-like alkaline phosphatase, germ cell alkaline phos-phatase (GCAP), tissue non-specific alkaline phosphatase (TNAP; which is primarily found in the liver, kidney, and bone), bone alkaline phosphatase, liver alkaline phos-phatase, kidney alkaline phosphatase, bacterial alkaline phosphatase, fungal alkaline phosphatase, shrimp alkaline phosphatase, modified IAP, recombinant IAP, or any poly-peptide comprising alkaline phosphatase activity.

In various embodiments, the present invention contem-plates the use of mammalian alkaline phosphatases includ-ing, but not limited to, intestinal alkaline phosphatase (IAP), placental alkaline phosphatase (PLAP), germ cell alkaline phosphatase (GCAP), and the tissue non-specific alkaline phosphatase (TNAP).

IAPs

In some embodiments, the AP-based agent is IAP. IAP is produced in the proximal small intestine and is bound to the enterocytes via a glycosyl phosphatidylinositol (GPI) anchor. Some IAP is released into the intestinal lumen in conjunction with vesicles shed by the cells and as soluble protein stripped from the cells via phospholipases. The enzyme then traverses the small and large intestine such that some active enzyme can be detected in the feces. In an embodiment, the IAP is human IAP (hIAP). In an embodi-ment, the IAP is calf IAP (cIAP), also known as bovine IAP (bIAP). There are multiple isozymes of bIAP, for example, with bIAP II and IV having higher specific activity than bIAP I. In an embodiment, the IAP is any one of the cIAP or bIAP isozymes (e.g., bIAP I, II, and IV). In an embodi-ment, the IAP is bIAP II. In another embodiment, the IAP is bIAP IV.

IAP Variants

Also included within the definition of IAPs are IAP variants. An IAP variant has at least one or more amino acid modifications, generally amino acid substitutions, as com-pared to the parental wild-type sequence. In some embodi-ments, an IAP of the invention comprises an amino sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with any of the sequences disclosed herein. In addition, IAP variants retain most or all of their biochemical activity, measured as described herein.

Mammalian alkaline phosphatases are GPI anchored pro-teins. They have signal peptides and are translated into the secretory pathway. Once in the endoplasmic reticulum (ER), the proteins are glycosylated and folded. There are two disulfide bonds as well as a single free cysteine that is apparently not accessible on the surface. In the late ER, the carboxy terminus is removed and the GPI anchor is appended. GPI anchoring is therefore a process that occurs at the carboxy terminus of the alkaline phosphatase. The inclusion of stop codons at the anchor site enables secretion of biologically active protein (presumably the homodimer). While there is no consensus sequence, the carboxy terminus includes three amino acids, termed omega, omega +1, and omega +2 which are followed by a short stretch of hydro-philic amino acids and then a stretch of hydrophobic amino acids. Without wishing to be bound by theory, it is believed that the hydrophobicity is critical for embedding the carboxy terminus in the ER membrane. There, an enzymatic reaction replaces the carboxy terminus with the GPI anchor.

Within human placental alkaline phosphatase (hPLAP), the GPI anchor is attached at an aspartate in the sequence, DAAH. Similarly, hIAP, bIAP II, and bIAP IV also have this DAAH sequence conserved, potentially serving as the GPI anchor site. Mutational studies with hPLAP indicate that preventing GPI anchoring results in intracellular retention. In addition, mutations around the anchor site or in the hydrophobic domain either 1) prevent anchor attachment leading to intracellular retention or 2) do not block anchor attachment. Without wishing to be bound by theory, it is believed that the hydrophobic domain serves as a signal for GPI anchor attachment. Truncating or eliminating the hydro-phobic domain leads to secretion. Finally, there is a single mutation in the hydrophobic domain that, in hPLAP, enables secretion of the protein with its hydrophobic domain intact.

In other embodiments, the AP-based agent of the inven-tion is a secreted protein; that is, in some embodiments, the AP-based agent is not GPI anchored, leading to secretion rather than intracellular retention. This can be accomplished in several ways. In some embodiments, the AP-based agent may lack the GPI anchor site, e.g. have the DAAH site removed, leading to secretion. Alternatively, this can be accomplished in some embodiments, the AP-based agent comprises a stop codon that is inserted immediately before the GPI anchor site. In an embodiment, the AP-based agent comprises a stop codon after the aspartate in the DAAH consensus site (e.g., at amino acid 503 of hIAP and bIAP IV or amino acid 506 of bIAP II). FIG. 1 depicts HIAP with a stop codon (SEQ ID NO: 4), bIAP II with a stop codon (SEQ ID NO: 5), and bIAP IV with a stop codon (SEQ ID NO: 6). In an embodiment, the AP-based agent is bIAP IV and includes a stop codon after amino acid 508 to mimic a secreted PLAP construct as depicted in FIG. 1 (SEQ ID NO: 7).

Human IAP

In various embodiments, the AP-based agent is hIAP. In some embodiments, the AP-based agent is hIAP comprising the amino acid sequence of SEQ ID NO: 1 as depicted in FIG. 1 or a variant as described herein, as long as the hIAP variant retains at least 80, 85, 90, 95, 98 or 100% of the phosphatase activity as compared to the wild type enzyme using an assay as outlined herein.

Included within the definition of hIAP are amino acid modifications, with amino acid substitutions finding particular use in the present invention. For example, without wishing to be bound by theory, it is believed that a cysteine at the carboxy terminus of the AP-based agent (e.g., at position 500 of SEQ ID NO: 1) may interfere with protein folding. Accordingly, in some embodiments, the AP-based agent includes a mutation of the cysteine (e.g., at position 500 of SEQ ID NO: 1). In some embodiments, the cysteine is replaced with any amino acid, although glycine finds particular use in some embodiments. Furthermore, the C-terminal cysteine can also be deleted.

As will be appreciated by those in the art, additional amino acid modifications can be made in hIAP as discussed herein. For example, in some embodiments, a stop codon may be inserted after the aspartate in the DAAH consensus site (e.g., at amino acid 503 of hIAP). FIG. 1 depicts hIAP with an inserted stop codon (SEQ ID NO: 4).

Bovine IAPs

In some embodiments, the IAP is bovine IAP (bIAP).

In various embodiments, the AP-based agent is bovine IAP II (bIAP II) or a variant as described herein, as long as the bIAP variant retains at least 80, 85, 90, 95, 98 or 100% of the phosphatase activity using an assay as outlined herein. In an embodiment, the bIAP II comprises the signal peptide and carboxy terminus of bIAP I. In an embodiment, the bIAP II comprises an aspartate at position 248 (similar to bIAP IV). In an embodiment, the bIAP II comprises the amino acid sequence of SEQ ID NO: 2. FIG. 1 depicts BIAP II with 248D—SEQ ID NO: 2. The signal peptide and sequence past 480 are derived from bIAP I.

Also included within the definition of bIAP II are amino acid variants as described herein. For example, in some embodiments, a stop codon may be inserted after the aspartate in the DAAH consensus site (e.g., at amino acid 506 of bIAP II). FIG. 1 depicts bIAP II with an inserted stop codon (SEQ ID NO: 5).

In various embodiments, the bIAP II comprises the amino acid sequence of SEQ ID NO: 39.

```
BIAP II with stop codon and no leader sequence
(SYN-020) (SEQ ID NO: 39):
LIPAEEENPAFWNRQAAQALDVAKKLQPIQTAAKNVILFLGDGMGVPTV

TATRILKGQMNGKLGPETPLAMDQFPYVALSKTYNVDRQVPDSAGTATA

YLCGVKGNYRTIGVSAAARYNQCNTTRGNEVTSVINRAKKAGKAVGVVT

TTRVQHASPAGAYAHTVNRNWYSDADLPADAQKNGCQDIAAQLVYNMDI

DVILGGGRMYMFPEGTPDPEYPDDASVNGVRKDKQNLVQEWQAKHQGAQ

YVWNRTALLQAADDSSVTHLMGLFEPADMKYNVQQDHTKDPTLAEMTEA
```

-continued

```
ALQVLSRNPRGFYLFVEGGRIDHGHHDGKAYMALTEAIMFDNAIAKANE

LTSELDTLILVTADHSHVFSFGGYTLRGTSIFGLAPGKALDSKSYTSIL

YGNGPGYALGGGSRPDVNGSTSEEPSYRQQAAVPLASETHGGEDVAVFA

RGPQAHLVHGVQEETFVAHIMAFAGCVEPYTDCNLPAPATATSIPD
```

In various embodiments, the AP-based agent is bIAP IV or a variant thereof as described herein, as long as the bIAP IV variant retains at least 80, 85, 90, 95, 98 or 100% of the phosphatase activity using an assay as outlined herein. In an embodiment, the bIAP IV comprises the amino acid sequence of SEQ ID NO: 3, as depicted in FIG. 1.

Also included within the definition of bIAP IV are amino acid variants as described herein. For example, in some embodiments, a stop codon may be inserted after the aspartate in the DAAH consensus site (e.g., at amino acid 503 of bIAP IV). FIG. 1 depicts bIAP IV with an inserted stop codon (SEQ ID NO: 6). In an embodiment, the AP-based agent is bIAP IV and includes a stop codon after amino acid 508 to mimic a secreted PLAP construct, as depicted in FIG. 1 (SEQ ID NO: 7).

Bacterial APs

In various embodiments, the present invention contemplates the use of bacterial alkaline phosphatases. In some embodiments, the AP-based agent of the invention is derived from *Bacillus subtilis*. *Bacillus subtilis* is a Gram-positive bacterium found in soil and the GI tract of humans. *Bacillus subtilis* secretes high levels of proteins into the environment and in the human GI tract that are properly folded. Without wishing to be bound by theory, it is believed that *Bacillus subtilis* secreted proteins in the GI tract may be resistant to degradation by common GI proteases. *Bacillus subtilis* expresses at high levels an alkaline phosphatase multigene family. Among those isozymes, alkaline phosphatase IV is responsible for the majority of total alkaline phosphatase expression and activity in *B. subtilis*. In some embodiments, the AP-based agent of the invention is derived from *Bacillus licheniformis*. In some embodiments, the AP-based agent of the invention is derived from *Escherichia coli*.

Accordingly, in an illustrative embodiment, the AP-based agent of the invention is derived from alkaline phosphatase IV of *Bacillus subtilis*. In an embodiment, the bacterial alkaline phosphatase may have nucleotide and amino acid sequences as depicted in FIG. 1, including *Bacillus subtilis* JH642 alkaline phosphatase IV, mature protein nucleotide sequence—SEQ ID NO: 16; and *Bacillus subtilis* JH642 alkaline phosphatase IV, mature protein amino acid sequence—SEQ ID NO: 17, or variants as described herein, as long as the hIAP variant retains at least 80, 85, 90, 95, 98 or 100% of the phosphatase activity using an assay as outlined herein.

In some embodiments, the AP-based agents include bacterial alkaline phosphatases that have one or more mutations that alter catalytic activity. In some embodiments, the bacterial alkaline phosphatases include one or more mutations such that their catalytic activity is similar or higher than mammalian alkaline phosphatases. In some embodiments, the bacterial alkaline phosphatases include one or more mutations that alter their de-phosphorylation profile. In an embodiment, the bacterial alkaline phosphatases of the invention exhibit similar de-phosphorylation profile as mammalian alkaline phosphatases. In some embodiments, the bacterial alkaline phosphatases include one or more mutations that alter their activity at higher pH. In an embodiment, the bacterial alkaline phosphatases of the invention exhibit similar activity at higher pH as mammalian alkaline phosphatases. In some embodiments, the bacterial alkaline phosphatases include one or more mutations that alter their metal requirements. In an embodiment, the bacterial alkaline phosphatases of the invention exhibit metal requirements (e.g., Mg) similar to mammalian alkaline phosphatases.

For example, in certain embodiments, the AP-based agent of the invention is derived from *Bacillus subtilis* JH642 alkaline phosphatase IV, and has one or more mutations at positions 101, 328, A330, and 374. For example, the AP-based agent may include one or more of the following mutations: D101A, W328H, A330N and G374C.

Fusion Proteins

In some embodiments, the AP-based agent comprises an alkaline phosphatase fused to a "fusion partner", which is a protein domain that is added either to the N- or C-terminus of the IAP domain, optionally including a linker. In some embodiments, the alkaline phosphatase is fused to a protein domain that promotes protein folding and/or protein purification and/or protein dimerization and/or protein stability. In various embodiments, the AP-based agent fusion protein has an extended serum half-life. In various embodiments, the AP-based agent of the invention is an Fc fusion protein.

In an embodiment, the alkaline phosphatase is fused to an immunoglobulin Fc domain and/or hinge region. In an embodiment, the AP-based agent of the invention comprises an alkaline phosphatase fused to the hinge region and/or Fc domain of IgG.

In various embodiments, the AP-based agent is fused to a Fc domain of IgG comprising one or more mutations. In some embodiments, the one or more mutations in the Fc domain of IgG function to increase serum half-life and longevity. In some embodiments, the Fc domain of IgG comprises one or more mutations at amino acid residues 251-256, 285-290, 308-314, 385-389 and 428-436, numbered according to the EU index as in Kabat (see Kabat et al., (1991) Sequences of Proteins of Immunological Interest, U.S. Public Health Service, National Institutes of Health, Washington, DC). In some embodiments, at least one of the amino acid substitutions in the Fc domain of IgG is at amino acid residue 252, 254, 256, 309, 311, 433 or 434. In an embodiment, the amino acid substitution at amino acid residue 252 is a substitution with tyrosine, phenylalanine, tryptophan or threonine. In an embodiment, the amino acid substitution at amino acid residue 254 is a substitution with threonine. In an embodiment, the amino acid substitution at amino acid residue 256 is a substitution with serine, arginine, glutamine, glutamic acid, aspartic acid, or threonine. In an embodiment, the amino acid substitution at amino acid residue 309 is a substitution with proline. In an embodiment, the amino acid substitution at amino acid residue 311 is a substitution with serine. In an embodiment, the amino acid substitution at amino acid residue 385 is a substitution with arginine, aspartic acid, serine, threonine, histidine, lysine, alanine or glycine. In an embodiment, the amino acid substitution at amino acid residue 386 is a substitution with threonine, proline, aspartic acid, serine, lysine, arginine, isoleucine, or methionine. In an embodiment, the amino acid substitution at amino acid residue 387 is a substitution with arginine, proline, histidine, serine, threonine, or alanine. In an embodiment, the amino acid substitution at amino acid residue 389 is a substitution with proline, serine or asparagine. In an embodiment, the amino acid substitution at amino acid residue 433 is a substitution with arginine, serine, isoleucine, proline, or glutamine. In an embodiment, the amino acid substitution at amino acid residue 434 is a substitution with histidine, phenylalanine, or tyrosine.

In some embodiments, the Fc domain of IgG comprises one or more mutations at amino acid residue 252, 254, 256, 433, 434, or 436. In an embodiment, the Fc domain of IgG includes a triple M252Y/S254T/T256E mutation or YTE mutation. In another embodiment, the Fc domain of IgG includes a triple H433K/N434F/Y436H mutation or KFH mutation. In a further embodiment, the Fc domain of IgG includes a YTE and KFH mutation in combination. Additional illustrative mutations in the Fc domain of IgG are described, for example, in Robbie, et al., Antimicrobial Agents and Chemotherapy (2013), 57(12):6147-6153, Dall'Acqua et al., JBC (2006), 281(33):23514-24, Dall'Acqua et al., Journal of Immunology (2002), 169:5171-80, and U.S. Pat. No. 7,083,784, the entire contents of which are hereby incorporated by reference. In various embodiments, the one or more mutations in the Fc domain of IgG increases affinity for the neonatal Fc receptor (FcRn). In some embodiments, the one or more mutations in the Fc domain of IgG increases affinity for FcRn at a pH of about 6.0, about 6.1, about 6.2, about 6.3, about 6.4, or about 6.5.

In various embodiments, the alkaline phosphatase is fused to one or more of PEG, XTENylation (e.g. as rPEG), polysialic acid (POLYXEN), albumin, elastin-like protein, elastin like protein (ELP), PAS, HAP, GLK, CTP, and transferrin. In various embodiments, the alkaline phosphatase is fused to one or more of the agents described in BioDrugs (2015) 29:215-239, the entire contents of which are hereby incorporated by reference.

Linkers

In an embodiment, the alkaline phosphatase is fused to a protein domain (e.g., an immunoglobulin Fc domain) via a linker to the GPI anchor site. For example, the alkaline phosphatase may be fused to a protein domain via the aspartate at the GPI anchor sequence. The invention contemplates the use of a variety of linker sequences. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present AP-based agent. In another example, the linker may function to target the AP-based agent to a particular cell type or location.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). In an embodiment, the linker sequence is GGSGGSGGGGSGGGGS (SEQ ID NO: 18). Additional illustrative linkers include, but are not limited to, linkers having the sequence LE, GGGGS (SEQ ID NO: 19), (GGGGS)n (n=2-4) (SEQ ID NOs: 20-22), (Gly)8 (SEQ ID NO: 23), (Gly)6 (SEQ ID NO: 24), (EAAAK)n (n=1-3) (SEQ ID NOs: 25-27), A(EAAAK)nA (n=2-5) (SEQ ID NOs: 28-31), AEAAAKEAAAKA SEQ ID NO: 32), A(EAAAK)4ALEA(EAAAK)4A (SEQ ID NO: 33), PAPAP (SEQ ID NO: 34), KESGSVSSEQLAQFRSLD (SEQ ID NO: 35), EGKSSGSGSESKST (SEQ ID NO: 36), GSAGSAAGSGEF (SEQ ID NO: 37), and (XP)n, with X designating any amino acid, e.g., Ala, Lys, or Glu. In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). In some embodiments, the linker is a synthetic linker such as PEG.

Illustrative Fc fusion constructs of the invention include those depicted in FIG. 1, including BIAP II with Fc Fusion (SEQ ID NO: 8)—Fc domain underlined; and BIAP IV with Fc Fusion (SEQ ID NO: 9)—Fc domain underlined.

Pro-Enzyme Fusions

The invention additionally provides C-terminal fusions for pro-enzyme functions. Without wishing to be bound by theory, it is believed that mammalian alkaline phosphatases may also be generated as inactive pro-enzymes. This is because alkaline phosphatases can dephosphorylate ATP, so that activity in the ER could drain the ER of its major energy source. Without wishing to be bound by theory, it is believed that the inhibitory function is located to the carboxy terminus that would be relieved upon GPI anchor addition. Alternatively, other activities such as folding or metal (Zn or Mg) inclusion could control activity.

In various embodiments, the AP-based agent of the invention is a pro-enzyme. In an embodiment, the activity of the proenzyme is suppressed by a carboxy terminus. In an embodiment, protease removal of the carboxy terminus reactivates the enzymatic activity of the alkaline phosphatase. In an embodiment, the pro-enzyme is more efficiently secreted than the enzyme without the carboxy terminus.

A *Saccharomyces* alkaline phosphatase, Pho8, is produced as an inactive pro-enzyme. It is not GPI anchored, but is a transmembrane protein with its amino terminus extending out of a lysosome into the cytoplasm. Within the lysosome, an enzyme, PEP4, cleaves the carboxy terminus to activate the enzyme.

In some embodiments, for generation of the pro-enzyme, the native carboxy terminus of the alkaline phosphatase is replaced with the analogous sequence from hPLAP. In some embodiments, a mutation is made in the hydrophobic carboxy tail to promote protein secretion without cleavage of the carboxy terminus. In an illustrative embodiment, a single point mutation such as a substitution of leucine with e.g., arginine is generated in the hydrophobic carboxy terminus (e.g. ALLPLLAGTL is changed to e.g., ALLPLRAGTL) to result in secretion of the enzyme without removal of the carboxy terminus.

In an embodiment, the AP-based agent is altered to include a specific enzyme cleavage site which allows subsequent removal of the carboxy terminus. In an embodiment, the AP-based agent includes a protease cleavage site. Illustrative protease cleavage sites include, but are not limited to, cleavage sites recognized by furin, Rhinovirus 16 3C protease, factor Xa protease, trypsin, chymotrypsin, elastase, pepsin, papain subtilisin, thermolysin, V-8 protease, submaxillaris protease, clostripain, thrombin, collagenase, and any other endoproteases. In an alternative embodiment, the AP-based agent includes a cleavage site recognized by a digestive enzyme present in the GI tract. In such embodiments, the AP-based agent may be administered as a prodrug that is subsequently activated in the GI tract.

In an illustrative embodiment, the proenzyme is a proenzyme of bIAP IV having sequences depicted in FIG. 1, including BIAP IV with the hPLAP Carboxy Terminus and Mutation for Unprocessed Secretion and RV3C Cleavage (at . . . LEVLFQGP . . . ) (SEQ ID NO: 10); and BIAP IV with hPLAP Carboxy Terminus and Mutation for Unprocessed Secretion and FXa Cleavage (at . . . IEGR . . . ) (SEQ ID NO: 11).

Expression Variants

In various embodiments, the AP-based agent of the invention is efficiently expressed and secreted from a host cell. In an embodiment, the AP-based agent of the invention is efficiently transcribed in a host cell. In another embodiment, the AP-based agent exhibits enhanced RNA stability and/or transport in a host cell. In another embodiment, the AP-based agent is efficiently translated in a host cell. In another embodiment, the AP-based agent exhibits enhanced protein stability.

In various embodiments, the AP-based agents are efficiently expressed in a host cell. In an embodiment, the Kozak sequence of the DNA construct encoding the AP-based agent is optimized. The Kozak sequence is the nucleotide sequence flanking the ATG start codon that instructs the ribosome to start translation. There is flexibility in the design of a Kozak sequence, but one canonical sequence is GCCGCCACCATGG (SEQ ID NO: 38). The purine in the –3 position and the G in the +4 position are the most important bases for translation initiation. For hIAP, bIAP II, and bIAP IV, the second amino acid, that is, the one after the initiator methionine, is glutamine. Codons for glutamine all have a C in the first position. Thus, their Kozak sequences all have an ATGC sequence. Accordingly, in various embodiments, the ATGC sequence is changed to ATGG. This can be achieved by changing the second amino acid to a glycine, alanine, valine, aspartate, or glutamic acid, all of whose codons have a G in the first position. These amino acids may be compatible with signal peptide function. In alternative embodiments, the entire signal peptide is substituted for peptide having a canonical Kozak sequence and is derived from a highly expressed protein such as an immunoglobulin.

In various embodiments, the signal peptide of the AP-based agent may be deleted and/or substituted. For example, the signal peptide may be deleted, mutated, and/or substituted (e.g., with another signal peptide) to ensure protein expression.

In some embodiments, the DNA construct encoding the AP-based agent of the invention comprises untranslated DNA sequences. Such sequences include an intron, which may be heterologous to the IAP protein or native to the IAP protein including the native first and/or second intron and/or a native 3' UTR. Without wishing to be bound by theory, it is believed that include of these sequences enhance protein expression by stabilizing the mRNA. Accordingly, in various embodiments, the DNA construct encoding the AP-based agent of the invention comprises the 5'UTR and/or the 3'UTR. Provided in FIG. 1 are illustrative IAP DNA sequences with a first intron and a 3'UTR, including hIAP with native first intron (shown as bolded and underlined)—SEQ ID NO: 12; hIAP with native 3' UTR (shown as bolded and underlined)—SEQ ID NO: 13; bIAP IV with the first intron from bIAP I (shown as bolded and underlined)—SEQ ID NO: 14; and bIAP IV with the 3' UTR from bIAP I (shown as bolded and underlined)—SEQ ID NO: 15.

In various embodiments, the AP-based agent of the invention comprises a nucleotide sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with any of the sequences disclosed herein.

In various embodiments, the AP-based agent of the invention may comprise an amino acid sequence having one or more amino acid mutations relative to any of the protein sequences described herein. In some embodiments, the one or more amino acid mutations may be independently selected from substitutions, insertions, deletions, and truncations.

In various embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosome, citrulline, homocitrulline, cysteic acid, t-butylglycine, t-butylalanine, phenylglycine, cyclohexylalanine, β-alanine, fluoro-amino acids, designer amino acids such as β-methyl amino acids, C α-methyl amino acids, N α-methyl amino acids, and amino acid analogs in general).

Mutations may be made to the AP-based agent of the invention to select for agents with desired characteristics. For examples, mutations may be made to generate AP-based agents with enhanced catalytic activity or protein stability. In various embodiments, directed evolution may be utilized to generate AP-based agents of the invention. For example, error-prone PCR and DNA shuffling may be used to identify mutations in the bacterial alkaline phosphatases that confer enhanced activity.

Modified Release Formulation and Dosage Forms

The modified-release formulation of AP-based agent (e.g. IAP, or the other AP-based agent agents described herein, and variants thereof) may further comprise a pharmaceutically acceptable carrier or excipient. As one skilled in the art will recognize, the formulations can be in any suitable form appropriate for the desired use and route of administration.

In various embodiments, the modified-release formulation of the present invention comprises a core particle, a base coat over the core particle, and wherein the base coat comprises the AP-based agent. In further embodiments, the core particle comprises sucrose. In some embodiments, the AP-based agent of the base coat is encapsulated within the core particle, and can include a plurality of core particles.

In various embodiments, the formulation of the present invention is in the form of a capsule (e.g., a hard gelatin or HPMC capsule) comprising a plurality of enteric-coated AP-based agent-containing pellets. In such embodiments, the pellets (or each individual pellet) comprise an AP-based agent (e.g. IAP, or the other AP-based agent agents described herein, and variants thereof), a sucrose sphere, which the AP-based agent, for example, IAP or a variant, is sprayed onto, a binder excipient (e.g., hydroxypropylcellulose (HPC)), an enteric polymer (e.g., EUDRAGIT L30 D-55), HTP-20 (e.g., PLASACRYL HTP 20), which is an additive that improves coating efficiency and reduces processing times, and buffer salts (e.g., a Tris base, magnesium chloride, magnesium sulfate, zinc chloride or zinc sulfate).

In various embodiments, the formulation of the present invention comprises a modified-release coating that is stable in gastric fluid and/or intestinal fluid and is degraded by a microbial enzyme present in the gut flora. In further embodiments, the modified-release coating solubility is pH-dependent. In further embodiments, the modified-release coating has a time-dependent erosion profile.

In various embodiments, the formulation of the present invention comprises at least one modified-release pellet, wherein each modified-release pellet comprises about 1-10% by weight AP-based agent (e.g. IAP, or the other AP-based agent agents described herein, and variants thereof). For example, the AP-based agent (e.g. IAP, or the other AP-based agent agents described herein, and variants thereof) may be present at about 1%, about 2%, about 3%, about 4%, about 5%, about 6%, about 7%, about 8%, about 9%, or about 10% by weight. In some embodiments, the pellets (or each individual pellet) comprise about 75-95% by weight sucrose sphere. For example, the sucrose sphere may be present at about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95% by weight. In some embodiments, the pellets (or each individual pellet) comprise about 5-15% by weight hydroxypropylcellulose (HPC). For example, the hydroxypropylcellulose may be present at about 5%, about 6%, about 7%, about 8%, about 9%, about 10%, about 11%, about 12%, about 13%, about 14%, or about 15% by weight. In some embodiments, the pellets (or each individual pellet) comprise about 0.5-2% by weight of buffer salt. The buffer salts may be selected from a Tris base, magnesium chloride, and zinc sulfate. For example, the buffer salts may be present at about 0.5%, about 0.6%, about 0.7%, about 0.8%, about 0.9%, about 1.0%, about 1.1%, about 1.2%, about 1.3%, about 1.4%, about 1.5%, 1.6%, about 1.7%, about 1.8%, about 1.9%, or about 2.0% by weight. In some embodiments, the formulation comprises a single layer enteric coating comprising about 20-40%, about 25-40%, about 25-35%, about 30-40%, or about 35-40% enteric polymer weight gain. In some embodiments, the formulation comprises a double layer enteric coating comprising about 20-40%, about 25-40%, about 25-35%, about 30-40%, or about 35-40% enteric polymer (e.g., EUDRAGIT L30 D-55) weight gain and about 5-15%, about 5-10%, about 7-15%, about 7-10%, about 10-15%, about 6-9%, or about 7-8% hydroxypropylcellulose weight gain. The weight as described herein refers to the total weight of all components.

In various embodiments, the formulation of the present invention comprises at least one modified-release pellet, wherein each modified-release pellet comprises about 5% by weight AP-based agent (e.g. IAP, or the other AP-based agent agents described herein, and variants thereof); about 85% by weight sucrose sphere; about 9% by weight hydroxypropylcellulose; and about 1% by weight of buffer salt. In some embodiments, the formulation comprises a single layer enteric coating comprising about 20-40% enteric polymer (e.g., EUDRAGIT L30 D-55) weight gain or a double layer enteric coating comprising about 30% enteric polymer (e.g., EUDRAGIT L30 D-55) weight gain and about 7% hydroxypropylcellulose weight gain. The weight as described herein refers to the total weight of all components.

In various embodiments, the formulation of the present invention comprises at least one modified-release pellet, wherein each modified-release pellet comprises about 4.7% by weight AP-based agent (e.g. IAP, or the other AP-based agent agents described herein, and variants thereof); about 84.9% by weight sucrose sphere; about 9.3% by weight hydroxypropylcellulose; and about 1.2% by weight of buffer salt. In some embodiments, the formulation comprises a single layer enteric coating comprising about 20-40% enteric polymer (e.g., EUDRAGIT L 30 D-55) weight gain or a double layer enteric coating comprising about 30% enteric polymer (e.g., EUDRAGIT L 30 D-55) weight gain and about 7% hydroxypropylcellulose weight gain. The weight as described herein refers to the total weight of all components.

In various embodiments, the formulation of the present invention is in the form of a capsule (e.g., a hard gelatin or HPMC capsule) comprising about 25 mg of the AP-based agent (e.g. IAP, or the other AP-based agent agents described herein, and variants thereof). The capsule includes a plurality of enteric-coated AP-based agent-containing pellets. In various embodiments, the formulation of the present invention comprises at least one modified-release pellet, wherein each modified-release pellet comprises about 1-15% by weight AP-based agent (e.g. IAP, or the other AP-based agent agents described herein, and variants thereof). For example, the AP-based agent (e.g. IAP, or the other AP-based agent agents described herein, and variants thereof) may be present at about 1%, about 2%, about 3%, about 4%, about 5%, about 6%, about 7%, about 8%, about 9%, about 10%, about 12%, about 13%, about 14%, or about 15% by weight. In some embodiments, the pellets (or each individual pellet) comprise about 30-55% by weight sucrose sphere. For example, the sucrose sphere may be present at about 30%, about 31%, about 32%, about 33%, about 34%, about 35%, about 36%, about 37%, about 38%, about 39%, 40%, about 41%, about 42%, about 43%, about 44%, about 45%, about 46%, about 47%, about 48%, about 49%, about 50%, about 51%, about 52%, about 53%, about 54%, or about 55% by weight. In some embodiments, the pellets (or each individual pellet) comprise about 5-25% by weight hydroxypropylcellulose (HPC). For example, the hydroxypropylcellulose may be present at about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% by weight. In some embodiments, the pellets (or each individual pellet) comprise about 20-35% by weight EUDRAGIT L30 D-55. For example, the EUDRAGIT L30 D-55 may be present at about 20%, about 21%, about 22%, about 23%, about 24%, about 25%, about 26%, about 27%, about 28%, about 29%, about 30%, about 31%, about 32%, about 33%, about 34%, or about 35% by weight. In some embodiments, the pellets (or each individual pellet) comprise about 0.5-11% by weight HTP-20. For example, the HTP-20 may be present at about 0.5%, about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, about 10.0%, about 10.5%, or about 11.0% by weight. In some embodiments, the pellets (or each individual pellet) comprise about 0.5-2.5% by weight of buffer salt. The buffer salts may be selected from a Tris base, magnesium chloride, magnesium sulfate, zinc chloride and zinc sulfate. For example, the buffer salts may be present at about 0.5%, about 0.6%, about 0.7%, about 0.8%, about 0.9%, about 1.0%, about 1.1%, about 1.2%, about 1.3%, about 1.4%, about 1.5%, 1.6%, about 1.7%, about 1.8%, about 1.9%, about 2.0%, about 2.1%, about 2.2%, about 2.3%, about 2.4%, or about 2.5% by weight.

In various embodiments, the formulation of the present invention is in the form of a capsule (e.g., a hard gelatin or HPMC capsule) comprising about 25 mg of the AP-based agent (e.g. IAP, or the other AP-based agent agents described herein, and variants thereof). The capsule includes a plurality of enteric-coated AP-based agent-containing pellets. In such embodiments, the formulation comprises about 10% by weight AP-based agent (e.g. IAP, or the other AP-based agent agents described herein, and variants thereof); about 38% by weight sucrose sphere; about 19% by weight hydroxypropylcellulose (HPC); about 2% by weight of buffer salt; and about 26% by weight enteric polymer (e.g., EUDRAGIT L30 D-55).

In various embodiments, the formulation of the present invention is in the form of a capsule (e.g., a hard gelatin or HPMC capsule) comprising about 25 mg of the AP-based agent (e.g. IAP, or the other AP-based agent agents described herein, and variants thereof). The capsule includes a plurality of enteric-coated AP-based agent-containing pellets. In such embodiments, the formulation comprises about 9.7% by weight AP-based agent (e.g. IAP, or the other AP-based agent agents described herein, and variants thereof); about 37.7% by weight sucrose sphere; about 19.4% by weight hydroxypropylcellulose (HPC); about 2.4% by weight of buffer salt; and about 26.3% by weight enteric polymer (e.g., EUDRAGIT L 30 D-55).

In various embodiments, the formulation of the present invention is in the form of a capsule (e.g., a hard gelatin or HPMC capsule) comprising about 5 mg of the AP-based agent (e.g. IAP, or the other AP-based agent agents described herein, and variants thereof). The capsule includes a plurality of enteric-coated AP-based agent-containing pellets. In various embodiments, the formulation of the present invention comprises at least one modified-release pellet, wherein each modified-release pellet comprises about 1-15% by weight AP-based agent (e.g. IAP, or the other AP-based agent agents described herein, and variants thereof). For example, the AP-based agent (e.g. IAP, or the other AP-based agent agents described herein, and variants thereof) may be present at about 1%, about 2%, about 3%, about 4%, about 5%, about 6%, about 7%, about 8%, about 9%, about 10%, about 12%, about 13%, about 14%, or about 15% by weight. In some embodiments, the pellets (or each individual pellet) comprise about 30-55% by weight sucrose sphere. For example, the sucrose sphere may be present at about 30%, about 31%, about 32%, about 33%, about 34%, about 35%, about 36%, about 37%, about 38%, about 39%, 40%, about 41%, about 42%, about 43%, about 44%, about 45%, about 46%, about 47%, about 48%, about 49%, about 50%, about 51%, about 52%, about 53%, about 54%, or about 55% by weight. In some embodiments, the pellets (or each individual pellet) comprise about 5-25% by weight hydroxypropylcellulose (HPC). For example, the hydroxypropylcellulose may be present at about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% by weight. In some embodiments, the pellets (or each individual pellet) comprise about 20-35% by weight EUDRAGIT L30 D-55. For example, the EUDRAGIT L30 D-55 may be present at about 20%, about 21%, about 22%, about 23%, about 24%, about 25%, about 26%, about 27%, about 28%, about 29%, about 30%, about 31%, about 32%, about 33%, about 34%, or about 35% by weight. In some embodiments, the pellets (or each individual pellet) comprise about 0.5-11% by weight HTP-20. For example, the HTP-20 may be present at about 0.5%, about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, about 10.0%, about 10.5%, or about 11.0% by weight. In some embodiments, the pellets (or each individual pellet) comprise about 0.5-2.5% by weight of buffer salt. The buffer salts may be selected from a Tris base, magnesium chloride, magnesium sulfate, zinc chloride and zinc sulfate. For example, the buffer salts may be present at about 0.5%, about 0.6%, about 0.7%, about 0.8%, about 0.9%, about 1.0%, about 1.1%, about 1.2%, about 1.3%, about 1.4%, about 1.5%, 1.6%, about 1.7%, about 1.8%, about 1.9%, about 2.0%, about 2.1%, about 2.2%, about 2.3%, about 2.4%, or about 2.5% by weight.

In various embodiments, the formulation of the present invention is in the form of a capsule (e.g., a hard gelatin or HPMC capsule) comprising about 5 mg of the AP-based agent (e.g. IAP, or the other AP-based agent agents described herein, and variants thereof). The capsule includes a plurality of enteric-coated AP-based agent-containing pellets. In such embodiments, the formulation comprises about 9.7% by weight AP-based agent (e.g. IAP, or the other AP-based agent agents described herein, and variants thereof); about 37.7% by weight sucrose sphere; about 19.4% by weight hydroxypropylcellulose (HPC); about 2.4% by weight of buffer salt; and about 26.3% by weight enteric polymer (e.g., EUDRAGIT L 30 D-55).

In various embodiments, the formulation of the present invention is in the form of a capsule (e.g., a hard gelatin or HPMC capsule) comprising about 5 mg of the AP-based agent (e.g. IAP, or the other AP-based agent agents described herein, and variants thereof). The capsule includes a plurality of enteric-coated AP-based agent-containing pellets. In such embodiments, the formulation comprises about 9.7% by weight AP-based agent (e.g. IAP, or the other AP-based agent agents described herein, and variants thereof); about 37.7% by weight sucrose sphere; about 19.4% by weight hydroxypropylcellulose (HPC); about 2.4% by weight of buffer salt; and about 26.3% by weight enteric polymer (e.g., EUDRAGIT L 30 D-55).

In various embodiments, the formulation of the present invention is in the form of a capsule (e.g., a hard gelatin or HPMC capsule) comprising about 15 mg of the AP-based agent (e.g. IAP, or the other AP-based agent agents described herein, and variants thereof). The capsule includes a plurality of enteric-coated AP-based agent-containing pellets. In various embodiments, the formulation of the present invention comprises at least one modified-release pellet, wherein each modified-release pellet comprises about 1-15% by weight AP-based agent (e.g. IAP, or the other AP-based agent agents described herein, and variants thereof). For example, the AP-based agent (e.g. IAP, or the other AP-based agent agents described herein, and variants thereof) may be present at about 1%, about 2%, about 3%, about 4%, about 5%, about 6%, about 7%, about 8%, about 9%, about 10%, about 12%, about 13%, about 14%, or about 15% by weight. In some embodiments, the pellets (or each individual pellet) comprise about 30-55% by weight sucrose sphere. For example, the sucrose sphere may be present at about 30%, about 31%, about 32%, about 33%, about 34%, about 35%, about 36%, about 37%, about 38%, about 39%, 40%, about 41%, about 42%, about 43%, about 44%, about 45%, about 46%, about 47%, about 48%, about 49%, about 50%, about 51%, about 52%, about 53%, about 54%, or about 55% by weight. In some embodiments, the pellets (or each individual pellet) comprise about 5-25% by weight hydroxypropylcellulose (HPC). For example, the hydroxypropylcellulose may be present at about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% by weight. In some embodiments, the pellets (or each individual pellet) comprise about 20-35% by weight EUDRAGIT L30 D-55. For example, the EUDRAGIT L30 D-55 may be present at about 20%, about 21%, about 22%, about 23%, about 24%, about 25%, about 26%, about 27%, about 28%, about 29%, about 30%, about 31%, about 32%, about 33%, about 34%, or about 35% by weight. In some embodiments, the pellets (or each individual pellet) comprise about 0.5-11% by weight HTP-20. For example, the HTP-20 may be present at about 0.5%, about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, about 10.0%, about 10.5%, or about 11.0% by weight. In some embodiments, the pellets (or each individual pellet) comprise about 0.1-2.5% by weight of buffer salt. The buffer salts may be selected from a Tris base, magnesium chloride, magnesium sulfate, zinc chloride and zinc sulfate. For example, the buffer salts may be present at about 0.1%, 0.2%, 0.3%, 0.4%, 0.5%, about 0.6%, about 0.7%, about 0.8%, about 0.9%, about 1.0%, about 1.1%, about 1.2%, about 1.3%, about 1.4%, about 1.5%, 1.6%, about 1.7%, about 1.8%, about 1.9%, about 2.0%, about 2.1%, about 2.2%, about 2.3%, about 2.4%, or about 2.5% by weight.

In various embodiments, the formulation of the present invention is in the form of a capsule (e.g., a hard gelatin or HPMC capsule) comprising about 15 mg of the AP-based agent (e.g. IAP, or the other AP-based agent agents described herein, and variants thereof). The capsule includes a plurality of enteric-coated AP-based agent-containing pellets. In such embodiments, the formulation comprises about 10% by weight AP-based agent (e.g. IAP, or the other AP-based agent agents described herein, and variants thereof); about 39% by weight sucrose sphere; about 20% by weight hydroxypropylcellulose (HPC); about 0.5% by weight of buffer salt; and about 26% by weight enteric polymer (e.g., EUDRAGIT L30 D-55).

In various embodiments, the formulation of the present invention is in the form of a capsule (e.g., a hard gelatin or HPMC capsule) comprising about 15 mg of the AP-based agent (e.g. IAP, or the other AP-based agent agents described herein, and variants thereof). The capsule includes a plurality of enteric-coated AP-based agent-containing pellets. In such embodiments, the formulation comprises about 10.0% by weight AP-based agent (e.g. IAP, or the other AP-based agent agents described herein, and variants thereof); about 38.9% by weight sucrose sphere; about 20.0% by weight hydroxypropylcellulose (HPC); about 0.3% by weight of buffer salt; and about 26.3% by weight enteric polymer (e.g., EUDRAGIT L 30 D-55).

In various embodiments, the formulation of the present invention is in the form of a capsule (e.g., a hard gelatin or HPMC capsule) comprising about 5 mg of the AP-based agent (e.g. IAP, or the other AP-based agent agents described herein, and variants thereof). The capsule includes a plurality of enteric-coated AP-based agent-containing pellets. In various embodiments, the formulation of the present invention comprises at least one modified-release pellet, wherein each modified-release pellet comprises about 1-15% by weight AP-based agent (e.g. IAP, or the other AP-based agent agents described herein, and variants thereof). For example, the AP-based agent (e.g. IAP, or the other AP-based agent agents described herein, and variants thereof) may be present at about 1%, about 2%, about 3%, about 4%, about 5%, about 6%, about 7%, about 8%, about 9%, about 10%, about 12%, about 13%, about 14%, or about 15% by weight. In some embodiments, the pellets (or each individual pellet) comprise about 30-55% by weight sucrose sphere. For example, the sucrose sphere may be present at about 30%, about 31%, about 32%, about 33%, about 34%, about 35%, about 36%, about 37%, about 38%, about 39%, 40%, about 41%, about 42%, about 43%, about 44%, about 45%, about 46%, about 47%, about 48%, about 49%, about 50%, about 51%, about 52%, about 53%, about 54%, or about 55% by weight. In some embodiments, the pellets (or each individual pellet) comprise about 5-25% by weight hydroxypropylcellulose (HPC). For example, the hydroxypropylcellulose may be present at about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% by weight. In some embodiments, the pellets (or each individual pellet) comprise about 20-35% by weight EUDRAGIT L30 D-55. For example, the EUDRAGIT L30 D-55 may be present at about 20%, about 21%, about 22%, about 23%, about 24%, about 25%, about 26%, about 27%, about 28%, about 29%, about 30%, about 31%, about 32%, about 33%, about 34%, or about 35% by weight. In some embodiments, the pellets (or each individual pellet) comprise about 0.5-11% by weight HTP-20. For example, the HTP-20 may be present at about 0.5%, about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, about 10.0%, about 10.5%, or about 11.0% by weight. In some embodiments, the pellets (or each individual pellet) comprise about 0.1-2.5% by weight of buffer salt. The buffer salts may be selected from a Tris base, magnesium chloride, magnesium sulfate, zinc chloride and zinc sulfate. For example, the buffer salts may be present at about 0.1%, 0.2%, 0.3%, 0.4%, 0.5%, about 0.6%, about 0.7%, about 0.8%, about 0.9%, about 1.0%, about 1.1%, about 1.2%, about 1.3%, about 1.4%, about 1.5%, 1.6%, about 1.7%, about 1.8%, about 1.9%, about 2.0%, about 2.1%, about 2.2%, about 2.3%, about 2.4%, or about 2.5% by weight.

In various embodiments, the formulation of the present invention is in the form of a capsule (e.g., a hard gelatin or HPMC capsule) comprising about 5 mg of the AP-based agent (e.g. IAP, or the other AP-based agent agents described herein, and variants thereof). The capsule includes a plurality of enteric-coated AP-based agent-containing pellets. In such embodiments, the formulation comprises about 10% by weight AP-based agent (e.g. IAP, or the other AP-based agent agents described herein, and variants thereof); about 39% by weight sucrose sphere; about 20% by weight hydroxypropylcellulose (HPC); about 0.5% by weight of buffer salt; and about 26% by weight enteric polymer (e.g., EUDRAGIT L30 D-55).

In various embodiments, the formulation of the present invention is in the form of a capsule (e.g., a hard gelatin or HPMC capsule) comprising about 5 mg of the AP-based agent (e.g. IAP, or the other AP-based agent agents described herein, and variants thereof). The capsule includes a plurality of enteric-coated AP-based agent-containing pellets. In such embodiments, the formulation comprises about 10.0% by weight AP-based agent (e.g. IAP, or the other AP-based agent agents described herein, and variants thereof); about 38.9% by weight sucrose sphere; about 20.0% by weight hydroxypropylcellulose (HPC); about 0.3% by weight of buffer salt; and about 26.3% by weight enteric polymer (e.g., EUDRAGIT L 30 D-55).

In some embodiments, the administration of the modified-release formulation including AP-based agent (and/or additional therapeutic agents) is any one of oral, intravenous, and parenteral. In some embodiments, the administration of the modified-release formulation including AP-based agent (and/or additional agents) is not intravenous in order to, for example, prevent interference with an antibiotic administered systemically. In other embodiments, routes of administration include, for example: oral, intradermal, intramuscular, intraperitoneal, intravenous, subcutaneous, intranasal, epidural, sublingual, intracerebral, intravaginal, transdermal, rectally, by inhalation, or topically, particularly to the ears, nose, eyes, or skin.

In some embodiments, any formulation of the present invention comprises a core particle having a size between about 0.8 mm to about 2.0 mm, between about 0.9 mm to about 1.9 mm, between about 1 mm to about 1.8 mm, between about 1.1 mm to about 1.7 mm, between about 1.2 mm to about 1.6 mm, between about 1.3 mm to about 1.5 mm, between about 1 mm to about 1.3 mm, between about 1 mm to about 1.4 mm, between about 1 mm to about 1.5 mm, between about 1 mm to about 1.6 mm, between about 1 mm to about 1.7 mm, between about 1 mm to about 1.9 mm between about 1 mm to about 2.0 mm diameter. In some embodiments, the formulation comprises a core particle having a size of about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2.0 mm diameter.

Any modified-release formulation including AP-based agent (and/or additional therapeutic agents) as described herein may not contain a cofactor (e.g., $CaCl_2$ or $CoCl_2$).

Any modified-release formulation including AP-based agent (and/or additional therapeutic agents) as described herein can be administered orally. Such inventive formulations can also be administered by any other convenient route, for example, by intravenous infusion or bolus injection, by absorption through epithelial or mucocutaneous linings (e.g., oral mucosa, rectal and intestinal mucosa, etc.) and can be administered together with an additional therapeutic agent. Administration can be systemic or local.

Suitable dosage forms for oral use include, for example, solid dosage forms such as tablets, dispersible powders, granules, and capsules. In one embodiment, the modified-release formulation is in the form of a capsule. In another embodiment, the modified-release formulation is in the form of a tablet. In yet another embodiment, the modified-release formulation is in the form of a soft-gel capsule. In a further embodiment, the modified-release formulation is in the form of a gelatin or hydroxypropyl methylcellulose (HPMC) capsule.

In some dosage forms, the agents described herein are mixed with at least one inert, pharmaceutically acceptable excipient or carrier such as sodium citrate, dicalcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinylpyrrolidone, sucrose, acacia, polyvinyl alcohol, polyvinylpyrrolidone, methylcellulose, hydroxypropyl cellulose (HPC), and hydroxymethyl cellulose etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., i) lubricants such as talc, calcium stearate, magnesium stearate, solid polyethylene glycols, sodium lauryl sulfate, glyceryl behenate, etc., j) antioxidants and mixtures of such excipients. One of skill in the art will recognize that particular excipients may have two or more functions in the oral dosage form. In the case of an oral dosage form, for example, a capsule or a tablet, the dosage form may also comprise buffering agents.

The modified release formulation can additionally include a surface active agent. Surface active agents suitable for use in the present invention include, but are not limited to, any pharmaceutically acceptable, non-toxic surfactant. Classes of surfactants suitable for use in the compositions of the invention include, but are not limited to polyethoxylated fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-olyoxypropylene block copolymers, sorbitan fatty acid esters, lower alcohol fatty acid esters, ionic surfactants, and mixtures thereof. In some embodiments, compositions of the invention may comprise one or more surfactants including, but not limited to, sodium lauryl sulfate, polysorbate 20, polysorbate 40, polysorbate 60, polysorbate 80, and triethyl citrate.

The modified-release formulation can also contain pharmaceutically acceptable plasticizers to obtain the desired mechanical properties such as flexibility and hardness. Such plasticizers include, but are not limited to, triacetin, citric acid esters, triethyl citrate, phthalic acid esters, dibutyl sebacate, cetyl alcohol, polyethylene glycols, polysorbates or other plasticizers.

The modified-release formulation can also include one or more application solvents. Some of the more common solvents that can be used to apply, for example, a delayed-release coating composition include isopropyl alcohol, acetone, methylene chloride and the like.

The modified-release formulation can also include one or more alkaline materials. Alkaline material suitable for use in compositions of the invention include, but are not limited to, sodium, potassium, calcium, magnesium and aluminum salts of acids such as phosphoric acid, carbonic acid, citric acid and other aluminum/magnesium compounds. In addition, the alkaline material may be selected from antacid materials such as aluminum hydroxides, calcium hydroxides, magnesium hydroxides and magnesium oxide.

The solid oral dosage forms can be prepared by, for example granulation (e.g., wet or dry granulation) of the agents of the invention with one or more suitable excipients. Alternatively, the agents of the invention can be layered onto an inert core (e.g., a nonpareil/sugar sphere such as a sucrose sphere or silica sphere) using conventional methods such as fluidized bed or pan coating, or extruded and spheronized using methods known in the art, into active compound-containing pellets. In embodiment, the AP-based agent (e.g. IAP, or the other AP-based agent agents described herein, and variants thereof) is spray-coated onto a sucrose sphere. Such pellets can then be incorporated into tablets or capsules using conventional methods.

Suspensions, in addition to the active agents, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Besides inert diluents, the oral compositions can also include adjuvants such as sweetening, flavoring, and perfuming agents.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art.

The formulations comprising the AP-based agent (and/or additional therapeutic agents) may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, the modified-release formulation of the present invention may utilize one or more modified-release coatings such as delayed-release coatings to provide for effective, delayed yet substantial delivery of the AP-based agent (e.g. IAP, or the other AP-based agent agents described herein, and variants thereof) to the GI tract together with, optionally, other additional therapeutic agents.

In one embodiment, the delayed-release coating includes an enteric agent that is substantially stable in acidic environments and substantially unstable in near neutral to alkaline environments. In an embodiment, the delayed-release coating contains an enteric agent that is substantially stable in gastric fluid and/or intestinal fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT-type polymer (poly(methacrylic acid, methylmethacrylate), hydroxypropyl methylcellulose acetate succinate, cellulose acetate trimellitate, shellac or other suitable enteric coating polymers. The EUDRAGIT-type polymers include, for example, EUDRAGIT FS 30D, L 30 D-55, L 100-55, L 100, L 12,5, L 12,5 P, RL 30 D, RL PO, RL 100, RL 12,5, RS 30 D, RS PO, RS 100, RS 12,5, NE 30 D, NE 40 D, NM 30 D, S 100, S 12,5, and S 12,5 P. Similar polymers include KOLLICOAT MAE 30 DP and KOLLICOAT MAE 100 P. In some embodiments, one or more of EUDRAGIT FS 30D, L 30 D-55, L 100-55, L 100, L 12,5, L 12,5 P RL 30 D, RL PO, RL 100, RL 12,5, RS 30 D, RS PO, RS 100, RS 12,5, NE 30 D, NE 40 D, NM 30 D, S 100, S 12,5 S 12,5 P, KOLLICOAT MAE 30 DP and KOLLICOAT MAE 100 P is used. In various embodiments, the enteric agent may be a combination of the foregoing solutions or dispersions. In an embodiment, the delayed-release coating includes the enteric agent EUDRAGIT L 30 D-55 (poly(methacrylic acid-ethyl acrylate copolymer) 1:1).

In certain embodiments, one or more coating system additives are used with the enteric agent. For example, one or more PLASACRYL additives may be used as an anti-tacking agent coating additive. Exemplary PLASACRYL additives include, but are not limited to PLASACRYL HTP20 and PLASACRYL T20. In an embodiment, PLA-SACRYLHTP20 is formulated with EUDRAGIT L 30 D-55 coatings. In another embodiment, PlasACRYLT20 is formulated with EUDRAGIT FS 30 D coatings.

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS, EUDRAGIT RL, and EUDRAGIT NE. Insoluble polymers useful in the present invention include polyvinyl esters, polyvinyl acetals, polyacrylic acid esters, butadiene styrene copolymers, and the like. In one embodiment, colonic delivery is achieved by use of a slowly-eroding wax plug (e.g., various PEGS, including for example, PEG6000).

In a further embodiment, the delayed-release coating may be degraded by a microbial enzyme present in the gut flora. In one embodiment, the delayed-release coating may be degraded by a bacteria present in the small intestine. In another embodiment, the delayed-release coating may be degraded by a bacteria present in the large intestine.

In various embodiments, the invention provides a formulation comprising: a core particle having a base coat comprising one or more AP-based agents (e.g. IAP, or the other AP-based agent agents described herein, and variants thereof), and a delayed-release coating disposed over the coated core particle. The delayed-release coating may be substantially stable in acidic environments and/or gastric fluid, and/or substantially unstable in near neutral to alkaline environments and/or intestinal fluid thereby exposing the coated core particle to intestinal fluid. For example, in some embodiments, the coated pellets of the present invention do not substantially release AP-based agent in FaSSGF but do substantially release AP-based agent in FaSSIF. In some embodiments, the coated pellets of the present invention release at least about 40%, at least about 45%, at least about 50%, at least about 55%, at least about 60%, at least about 65%, at least about 70%, at least about 75%, at least about 80%, at least about 85%, at least about 90%, or at least about 95% AP-based agent in simulated gastric and/or intestinal fluid at about 20 minutes, about 40 minutes, about 1 hour, about 80 minutes, about 100 minutes, about 2 hours, about 140 minutes, about 160 minutes, about 3 hours, about 200 minutes, about 220 minutes, or about 4 hours.

In some embodiments, the coated pellets of the present invention comprising an AP-based agent are stable for at least about 3 days, at least about 9 days, at least about 12 days, at least about 15 days, at least about 20 days, at least about 23 days, at least about 27 days, at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 1 year, at least about 1.5 years, at least about 2 years in storage. In some embodiments, the pellets are stored at 2-8° C. under desiccation. In further embodiments, the coated pellets of the present invention comprising an AP-based agent retain at least about 50%, at least about 55%, at least about 60%, at least about 65%, at least about 70%, at least about 75%, at least about 80%, at least about 85%, at least about 90%, or at least about 95% activity over a storage duration.

The base coat comprising one or more AP-based agents may further comprise one or more additional therapeutic agents. Optionally a plurality of base coats may be applied to the core each of which may contain an AP-based agent and/or an additional therapeutic agent. In an embodiment, the core particle includes sucrose. The formulation can be prepared by methods known in the art. For example, AP-based agents (e.g., IAP, or the other AP-based agent agents described herein, and variants thereof) can be sprayed onto an inert core (e.g., a sucrose core or sucrose sphere) and spray-dried with an enteric layer (e.g., EUDRAGIT L30 D-55) to form AP-based agent (e.g., IAP, or the other AP-based agent agents described herein, and variants thereof)-containing pellets.

Optionally, the core particle may comprise one or more AP-based agents (e.g., IAP, or the other AP-based agent agents described herein, and variants thereof) and/or one or more additional therapeutic agents. In one embodiment, one or more doses of the AP-based agent may be encapsulated in a core particle, for example, in the form of a microsphere. For example, the AP-based agent may be combined with a polymer (e.g., latex), and then formed into a particulate, micro-encapsulated enzyme preparation, without using a sucrose core. The microspheres thus formed may be optionally covered with a delayed-release coating.

A variety of approaches for generating particulates (such as microspheres, aggregates, other) are known which are amenable to the inclusion of enzymes. They typically involve at least two phases, one containing the enzyme, and one containing a polymer that forms the backbone of the particulate. Most common are coacervation, where the polymer is made to separate from its solvent phase by addition of a third component, or multiple phase emulsions, such as water in oil in water (w/o/w) emulsion where the inner water phase contains the protein, the intermediate organic phase contains the polymer, and the external water phase stabilizers that support the w/o/w double emulsion until the solvents can be removed to form the microspheres. Alternatively, the AP-based agent (e.g., IAP, or the other AP-based agent agents described herein, and variants thereof) and stabilizing excipients (for example, trehalose, mannitol, Tween 80, polyvinyl alcohol) are combined and sprayed from aqueous solution and collected. The particles are then suspended in a dry, water immiscible organic solvent containing polymer and release modifying compounds, and the suspension sonicated to disperse the particles. An additional approach uses aqueous phases but no organic solvent. Specifically, the enzyme, buffer components, a polymer latex, and stabilizing and release-modifying excipients are dissolved/dispersed in water. The aqueous dispersion is spray-dried, leading to coalescence of the latex, and incorporation of the protein and excipients in particles of the coalesced latex. When the release modifiers are insoluble at acidic conditions but soluble at higher pHs (such as carboxylic acid) then release from the matrix is inhibited in the gastric environment.

In some embodiments, before applying the delayed-release coating to the coated core particle the particle can optionally be covered with one or more separating layers comprising pharmaceutical excipients including alkaline compounds such as for instance pH-buffering compounds. The separating layer essentially separates the coated core particle from the delayed-release coating.

The separating layer can be applied to the coated core particle by coating or layering procedures typically used with coating equipment such as a coating pan, coating granulator or in a fluidized bed apparatus using water and/or organic solvents for the coating process. As an alternative the separating layer can be applied to the core material by using a powder coating technique. The materials for separating layers are pharmaceutically acceptable compounds such as, for instance, sugar, polyethylene glycol, polyvinylpyrrolidone, polyvinyl alcohol, polyvinyl acetate, hydroxypropyl cellulose, methyl-cellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such as for instance magnesium stearate, titanium dioxide, talc and other additives can also be included in the separating layer.

In some embodiments, the coated particles with the delayed-release coating may be further covered with an overcoat layer. The overcoat layer can be applied as described for the other coating compositions. The overcoat materials are pharmaceutically acceptable compounds such as sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. The overcoat materials can prevent potential agglomeration of particles coated with the delayed-release coating, protect the delayed-release coating from cracking during the compaction process or enhance the tableting process.

In some embodiments, the modified-release formulation is a capsule filled with a plurality of AP-based agent-containing pellets (e.g., IAP (or the other AP-based agent agents described herein, and variants thereof)-containing pellets) from which the AP-based agent is released. In an embodiment, the capsule is a gelatin capsule, such as a hard gelatin capsule. In another embodiment, the capsule is a hydroxypropyl methylcellulose (HPMC) capsule. For example, the formulation may be in the form of capsules comprising multiple pellets. For example, the formulation may be in the form of capsules such as, for example, gelatin or hydroxypropyl methylcellulose (HPMC) capsules comprising multiple enteric-coated pellets containing AP-based agent (e.g. IAP, or the other AP-based agent agents described herein, and variants thereof). In such an embodiment, a combination of pellets may be utilized in which each pellet is designed to release at a specific time point or location. In various embodiments, the pellets (e.g., enteric-coated pellets) are designed to pass through the stomach unchanged and then release the AP-based agent (e.g. IAP, or the other AP-based agent agents described herein, and variants thereof) into one or more regions of the intestines. In some embodiments, the AP-based agent-containing pellets may be enteric-coated to release the AP-based agent (e.g. IAP, or the other AP-based agent agents described herein, and variants thereof) at different intestinal pH values.

The present invention also provides for modified-release formulations that release multiple doses of the AP-based agents (e.g., IAP, or the other AP-based agent agents described herein, and variants thereof) and/or additional therapeutic agent along the gastrointestinal tract. In such embodiments, the overall release profile of such a formulation may be adjusted by utilizing, for example, multiple particle types or multiple layers. In one embodiment, the first dose of the AP-based agent may be formulated for release in, for example, the small intestine (e.g., one or more of duodenum, jejunum, ileum) or the large intestine (e.g., one or more of cecum, ascending, transverse, descending or sigmoid portions of the colon, and rectum), whereas the second dose is formulated for delayed release in, for example, a different region of the small intestine (e.g., one or more of duodenum, jejunum, ileum) or the large intestine (e.g., one or more of cecum, ascending, transverse, descending or sigmoid portions of the colon, and rectum). Alternatively, multiple doses are released at different locations along the intestine. For example, in one embodiment, the first dose of the AP-based agent may be formulated for release in, for example, the small intestine (e.g., one or more of duodenum, jejunum, ileum), whereas the second dose is formulated for delayed release in, for example, another part of the small intestine (e.g., one or more of duodenum, jejunum, ileum). In another embodiment, the first dose of the AP-based agent may be formulated for release in, for example, the large intestine (e.g., one or more of cecum, ascending, transverse, descending or sigmoid portions of the colon, and rectum), whereas the second dose is formulated for delayed release in, for example, another part of the large intestine (e.g., one or more of cecum, ascending, transverse, descending or sigmoid portions of the colon, and rectum).

In various embodiments, the agents described herein may be in the form of a pharmaceutically acceptable salt, namely those salts which are suitable for use in contact with the tissues of humans and other animals without undue toxicity, irritation, allergic response and the like, and are commensurate with a reasonable benefit/risk ratio. Pharmaceutically acceptable salts are well known in the art. The salts can be prepared in situ during the final isolation and purification of the therapeutic agents, or separately by reacting the free base function with a suitable acid or a free acid functionality with an appropriate alkaline moiety. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

In various embodiments, the present formulations provide a number of advantages. For instance, the inventors have successfully formulated a protein (i.e. AP-based agent), which itself is challenging. This is compounded further by the GI tract environment in which the present formulations release drug in various embodiments. Further, in various embodiments, the present formulations provide for GI tract release that is sufficiently slow to allow good protective coverage in the GI tract from adverse effects of various antibiotics, e.g. in the small intestine (a benefit that is accentuated by an increase in AP-based agent half-life that is commensurate with a slower release). Furthermore, by coating the drug substance layer of the present pellets with HPC, as opposed to EUDRAGIT, for example, the present formulations minimize the amount of EUGRAGIT in the formulations and therefore mitigate possible dose-limiting toxicity and manufacturing complications.

Modified Release Profile

In one aspect, the present invention provides modified release formulations comprising at least one alkaline phosphatase (AP)-based agent, wherein the formulation releases a substantial amount of the AP-based agent into one or more regions of the GI tract. In some embodiments, the AP-based agent is IAP, or the other AP-based agent agents described herein, and variants thereof (e.g. as described above). For example, the formulation may release at least about 60% of the AP-based agent, for example, IAP, after the stomach and into one or more regions of the GI tract.

In various embodiments, the modified-release formulations of the present invention are designed for immediate release (e.g. upon ingestion). In various embodiments, the modified-release formulations may have sustained-release profiles, i.e. slow release of the active ingredient(s) in the body (e.g., GI tract) over an extended period of time. In various embodiments, the modified-release formulations may have a delayed-release profile, i.e. not immediately release the active ingredient(s) upon ingestion; rather, postponement of the release of the active ingredient(s) until the composition is lower in the gastrointestinal tract; for example, for release in the small intestine (e.g., one or more of duodenum, jejunum, ileum) or the large intestine (e.g., one or more of cecum, ascending, transverse, descending or sigmoid portions of the colon, and rectum). For example, a composition can be enteric coated to delay release of the active ingredient(s) until it reaches the small intestine or large intestine. In some embodiments, there is not a substantial amount of the active ingredient(s) of the present formulations in the stool.

In various embodiments, the modified-release formulation of the present invention releases at least 60% of the AP-based agent (e.g. IAP, or the other AP-based agent agents described herein, and variants thereof) after the stomach into one or more regions of the intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (e.g. IAP, or the other AP-based agent agents described herein, and variants thereof) in the intestine.

In various embodiments, the modified-release formulation of the present invention releases at least 60% of the AP-based agent (e.g. IAP, or the other AP-based agent agents described herein, and variants thereof) in the small intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (e.g. IAP, or the other AP-based agent agents described herein, and variants thereof) in the small intestine.

In one embodiment, the modified-release formulation of the present invention releases at least 60% of the AP-based agent (e.g. IAP, or the other AP-based agent agents described herein, and variants thereof) in the duodenum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (e.g. IAP, or the other AP-based agent agents described herein, and variants thereof) in the duodenum.

In one embodiment, the modified-release formulation of the present invention releases at least 60% of the AP-based agent (e.g. IAP, or the other AP-based agent agents described herein, and variants thereof) in the jejunum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (e.g. IAP, or the other AP-based agent agents described herein, and variants thereof) in the jejunum.

In one embodiment, the modified-release formulation of the present invention releases at least 60% of the AP-based agent (e.g. IAP, or the other AP-based agent agents described herein, and variants thereof) in the ileum and/or the ileocecal junction. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (e.g. IAP, or the other AP-based agent agents described herein, and variants thereof) in the ileum and/or the ileocecal junction.

In various embodiments, the modified-release formulation of the present invention releases at least 60% of the AP-based agent (e.g. IAP, or the other AP-based agent agents described herein, and variants thereof) in the large intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (e.g. IAP, or the other AP-based agent agents described herein, and variants thereof) in the large intestine.

In one embodiment, the modified-release formulation of the present invention releases at least 60% of the AP-based agent (e.g. IAP, or the other AP-based agent agents described herein, and variants thereof) in the cecum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (e.g. IAP, or the other AP-based agent agents described herein, and variants thereof) in the cecum.

In one embodiment, the modified-release formulation of the present invention releases at least 60% of the AP-based agent (e.g. IAP, or the other AP-based agent agents described herein, and variants thereof) in the ascending colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (e.g. IAP, or the other AP-based agent agents described herein, and variants thereof) in the ascending colon.

In one embodiment, the modified-release formulation of the present invention releases at least 60% of the AP-based agent (e.g. IAP, or the other AP-based agent agents described herein, and variants thereof) in the transverse colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (e.g. IAP, or the other AP-based agent agents described herein, and variants thereof) in the transverse colon.

In one embodiment, the modified-release formulation of the present invention releases at least 60% of the AP-based agent (e.g. IAP, or the other AP-based agent agents described herein, and variants thereof) in the descending colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (e.g. IAP, or the other AP-based agent agents described herein, and variants thereof) in the descending colon.

In one embodiment, the modified-release formulation of the present invention releases at least 60% of the AP-based agent (e.g. IAP, or the other AP-based agent agents described herein, and variants thereof) in the sigmoid colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (e.g. IAP, or the other AP-based agent agents described herein, and variants thereof) in the sigmoid colon.

In various embodiments, the modified-release formulation does not substantially release the AP-based agent (e.g. IAP, or the other AP-based agent agents described herein, and variants thereof) in the stomach.

In certain embodiments, the modified-release formulation releases the AP-based agent (e.g. IAP, or the other AP-based agent agents described herein, and variants thereof) at a specific pH. For example, in some embodiments, the modified-release formulation is substantially stable in an acidic environment and substantially unstable (e.g., dissolves rapidly or is physically unstable) in a near neutral to alkaline environment. In some embodiments, stability is indicative of not substantially releasing while instability is indicative of substantially releasing. For example, in some embodiments, the modified-release formulation is substantially stable at a pH of about 7.0 or less, or about 6.5 or less, or about 6.0 or less, or about 5.5 or less, or about 5.0 or less, or about 4.5 or less, or about 4.0 or less, or about 3.5 or less, or about 3.0 or less, or about 2.5 or less, or about 2.0 or less, or about 1.5 or less, or about 1.0 or less. In some embodiments, the present formulations are stable in lower pH areas and therefore do not substantially release in, for example, the stomach. In some embodiments, modified-release formulation is substantially stable at a pH of about 1 to about 4 or lower and substantially unstable at pH values that are greater. In these embodiments, the modified-release formulation is not substantially released in the stomach. In these embodiments, the modified-release formulation is substantially released in the small intestine (e.g. one or more of the duodenum, jejunum, and ileum) and/or large intestine (e.g. one or more of the cecum, ascending colon, transverse colon, descending colon, and sigmoid colon). In some embodiments, modified-release formulation is substantially stable at a pH of about 4 to about 5 or lower and consequentially is substantially unstable at pH values that are greater and therefore is not substantially released in the stomach and/or small intestine (e.g. one or more of the duodenum, jejunum, and ileum). In these embodiments, the modified-release formulation is substantially released in the large intestine (e.g. one or more of the cecum, ascending colon, transverse colon, descending colon, and sigmoid colon). In various embodiments, the pH values recited herein may be adjusted as known in the art to account for the state of the subject, e.g. whether in a fasting or postprandial state.

In some embodiments, the modified-release formulation is substantially stable in gastric fluid and substantially unstable in intestinal fluid and, accordingly, is substantially released in the small intestine (e.g. one or more of the duodenum, jejunum, and ileum) and/or large intestine (e.g. one or more of the cecum, ascending colon, transverse colon, descending colon, and sigmoid colon).

In some embodiments, the modified-release formulation is stable in gastric fluid or stable in acidic environments. These modified-release formulations release about 30% or less by weight of the AP-based agent (e.g. IAP, or the other AP-based agent agents described herein, and variants thereof) and/or additional therapeutic agent in the modified-release formulation in gastric fluid with a pH of about 4 to about 5 or less, or simulated gastric fluid with a pH of about 4 to about 5 or less, in about 15, or about 30, or about 45, or about 60, or about 90 minutes. Modified-release formulations of the of the invention may release from about 0% to about 30%, from about 0% to about 25%, from about 0% to about 20%, from about 0% to about 15%, from about 0% to about 10%, about 5% to about 30%, from about 5% to about 25%, from about 5% to about 20%, from about 5% to about 15%, from about 5% to about 10% by weight of the AP-based agent (e.g. IAP, or the other AP-based agent agents described herein, and variants thereof) and/or additional therapeutic agent in the modified-release formulation in gastric fluid with a pH of 4-5, or less or simulated gastric fluid with a pH of 4-5 or less, in about 15, or about 30, or about 45, or about 60, or about 90 minutes. Modified-release formulations of the invention may release about 1%, about 2%, about 3%, about 4%, about 5%, about 6%, about 7%, about 8%, about 9%, or about 10% by weight of the total AP-based agent (e.g. IAP, or the other AP-based agent agents described herein, and variants thereof) and/or additional therapeutic agent in the modified-release formulation in gastric fluid with a pH of 5 or less, or simulated gastric fluid with a pH of 5 or less, in about 15, or about 30, or about 45, or about 60, or about 90 minutes.

In some embodiments, the modified-release formulation is unstable in intestinal fluid. These modified-release formulations release about 70% or more by weight of the AP-based agent (e.g. IAP, or the other AP-based agent agents described herein, and variants thereof) and/or additional therapeutic agent in the modified-release formulation in intestinal fluid or simulated intestinal fluid in about 15, or about 30, or about 45, or about 60, or about 90 minutes. In some embodiments, the modified-release formulation is unstable in near neutral to alkaline environments. These modified-release formulations release about 70% or more by weight of the AP-based agent (e.g. IAP, or the other AP-based agent agents described herein, and variants thereof) and/or additional therapeutic agent in the modified-release formulation in intestinal fluid with a pH of about 4-5 or greater, or simulated intestinal fluid with a pH of about 4-5 or greater, in about 15, or about 30, or about 45, or about 60, or about 90 minutes. A modified-release formulation that is unstable in near neutral or alkaline environments may release 70% or more by weight of AP-based agent (e.g. IAP, or the other AP-based agent agents described herein, and variants thereof) and/or additional therapeutic agent in the modified-release formulation in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

In one embodiment, the modified-release formulation may remain essentially intact, or may be essentially insoluble, in gastric fluid. The modified-release formulation may include one or more delayed-release coatings that are pH dependent. Delayed-release coatings that are pH dependent will be substantially stable in acidic environments (pH of about 5 or less), and substantially unstable in near neutral to alkaline environments (pH greater than about 5). For example, the delayed-release coating may essentially disintegrate or dissolve in near neutral to alkaline environments such as are found in the small intestine (e.g. one or more of the duodenum, jejunum, and ileum) and/or large intestine (e.g. one or more of the cecum, ascending colon, transverse colon, descending colon, and sigmoid colon).

Alternatively, the stability of the modified-release formulation can be enzyme-dependent. In such embodiments, the modified-release formulation may include one or more delayed-release coatings that are enzyme-dependent. Delayed-release coating that are enzyme-dependent will be substantially stable in fluid that does not contain a particular enzyme and substantially unstable in fluid containing the enzyme. The delayed-release coating will essentially disintegrate or dissolve in fluid containing the appropriate enzyme. Enzyme-dependent control can be brought about, for example, by using materials which release the active ingredient only on exposure to enzymes in the intestine, such as galactomannans. Also, the stability of the modified-release formulation can be dependent on enzyme stability in the presence of a microbial enzyme present in the gut flora.

In various embodiments, the modified-release formulations comprising an AP-based agent (e.g. IAP, or variants thereof) are substantially stable in chyme. For example, there is, in some embodiments, a loss of less about 50% or about 40%, or about 30%, or about 20%, or about 10% of AP-based agent activity in about 10, or 9, or 8, or 7, or 6, or 5, or 4, or 3, or 2, or 1 hour from administration.

In some embodiments, a dual pulse formulation is provided. In various embodiments, the present invention provides for modified-release formulations that release multiple doses of the AP-based agent (e.g. IAP, or the other AP-based agent agents described herein, and variants thereof), at different locations along the intestines, at different times, and/or at different pH. In an illustrative embodiment, the modified-release formulation comprises a first dose of the AP-based agent and a second dose of the AP-based agent, wherein the first dose and the second dose are released at different locations along the intestines, at different times, and/or at different pH. For example, the first dose is released at the duodenum, and the second dose is released at the ileum. In another example, the first dose is released at the jejunum, and the second dose is released at the ileum. In other embodiments, the first dose is released at a location along the small intestine (e.g., the duodenum), while the second dose is released along the large intestine (e.g., the ascending colon). In various embodiments, the modified-release formulation may release at least one dose, at least two doses, at least three doses, at least four doses, at least five doses, at least six doses, at least seven doses, or at least eight doses of the AP-based agent (e.g. IAP, or the other AP-based agent agents described herein, and variants thereof) at different locations along the intestines, at different times, and/or at different pH. Further the dual pulse description herein applies to modified-release formulations that release an AP-based agent (e.g. IAP, or the other AP-based agent agents described herein, and variants thereof) and an additional therapeutic agent.

Administration and Dosage

It will be appreciated that the actual dose of the AP-based agent (e.g., IAP, or the other AP-based agent agents described herein, and variants thereof) to be administered according to the present invention will vary according to, for example, the particular dosage form and the mode of administration. Many factors that may modify the action of the AP-based agent (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

Individual doses of the AP-based agent (e.g., IAP, or the other AP-based agent agents described herein, and variants thereof) can be administered in unit dosage forms (e.g., tablets or capsules) containing, for example, from about 0.01 mg to about 1,000 mg, from about 0.01 mg to about 950 mg, from about 0.01 mg to about 900 mg, from about 0.01 mg to about 850 mg, from about 0.01 mg to about 800 mg, from about 0.01 mg to about 750 mg, from about 0.01 mg to about 700 mg, from about 0.01 mg to about 650 mg, from about 0.01 mg to about 600 mg, from about 0.01 mg to about 550 mg, from about 0.01 mg to about 500 mg, from about 0.01 mg to about 450 mg, from about 0.01 mg to about 400 mg, from about 0.01 mg to about 350 mg, from about 0.01 mg to about 300 mg, from about 0.01 mg to about 250 mg, from about 0.01 mg to about 200 mg, from about 0.01 mg to about 150 mg, from about 0.01 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg active ingredient, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg per unit dosage form, or from about 5 mg to about 80 mg per unit dosage form. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, inclusive of all values and ranges therebetween. In an embodiment, individual dose of the AP-based agent (e.g., IAP, or the other AP-based agent agents described herein, and variants thereof) is administered in an unit dosage form containing 25 mg of the AP-based agent. In another embodiment, individual dose of the AP-based agent (e.g., IAP, or the other AP-based agent agents described herein, and variants thereof) is administered in an unit dosage form containing 50 mg of the AP-based agent. In a further embodiment, individual dose of the AP-based agent (e.g., IAP, or the other AP-based agent agents described herein, and variants thereof) is administered in an unit dosage form containing 75 mg of the AP-based agent.

In one embodiment, the AP-based agent is administered at an amount of from about 0.01 mg to about 100 mg daily, an amount of from about 0.01 mg to about 1,000 mg daily from about 0.01 mg to about 950 mg daily, from about 0.01 mg to about 900 mg daily, from about 0.01 mg to about 850 mg daily, from about 0.01 mg to about 800 mg daily, from about 0.01 mg to about 750 mg daily, from about 0.01 mg to about 700 mg daily, from about 0.01 mg to about 650 mg daily, from about 0.01 mg to about 600 mg daily, from about 0.01 mg to about 550 mg daily, from about 0.01 mg to about 500 mg daily, from about 0.01 mg to about 450 mg daily, from about 0.01 mg to about 400 mg daily, from about 0.01 mg to about 350 mg daily, from about 0.01 mg to about 300 mg daily, from about 0.01 mg to about 250 mg daily, from about 0.01 mg to about 200 mg daily, from about 0.01 mg to about 150 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily.

In various embodiments, the AP-based agent is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, inclusive of all values and ranges therebetween.

In some embodiments, a suitable dosage of the AP-based agent (e.g., IAP, or the other AP-based agent agents described herein, and variants thereof) is in a range of about 0.01 mg/kg to about 100 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg body weight, inclusive of all values and ranges therebetween. In other embodiments, a suitable dosage of the AP-based agents in a range of about 0.01 mg/kg to about 10 mg/kg of body weight, in a range of about 0.01 mg/kg to about 9 mg/kg of body weight, in a range of about 0.01 mg/kg to about 8 mg/kg of body weight, in a range of about 0.01 mg/kg to about 7 mg/kg of body weight, in a range of 0.01 mg/kg to about 6 mg/kg of body weight, in a range of about 0.05 mg/kg to about 5 mg/kg of body weight, in a range of about 0.05 mg/kg to about 4 mg/kg of body weight, in a range of about 0.05 mg/kg to about 3 mg/kg of body weight, in a range of about 0.05 mg/kg to about 2 mg/kg of body weight, in a range of about 0.05 mg/kg to about 1.5 mg/kg of body weight, or in a range of about 0.05 mg/kg to about 1 mg/kg of body weight.

In accordance with certain embodiments of the invention, the AP-based agent may be administered, for example, about once per day, about every other day, about every third day, about once a week, about once every two weeks, about once every month, about once every two months, about once every three months, about once every six months, or about once every year. In certain embodiments, the AP-based agent may be administered more than once daily, for example, about two times, about three times, about four times, about five times, about six times, about seven times, about eight times, about nine times, or about ten times daily.

Additional Therapeutic Agents and Combination Therapy or Co-Formulation

Administration of the present compositions and formulations comprising the AP-based agent may be combined with additional therapeutic agents. Co-administration of the additional therapeutic agent and the present compositions/formulations may be simultaneous or sequential. Further, the present compositions/formulations may comprise an additional therapeutic agent (e.g. via co-formulation). For example, the additional therapeutic agent and the AP-based agent may be combined into a single formulation. Alternatively, the additional therapeutic agent and the AP-based agent may be formulated separately.

In one embodiment, the additional therapeutic agent and the AP-based agent are administered to a subject simultaneously. The term "simultaneously" as used herein, means that the additional therapeutic agent and the AP-based agent are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the AP-based agent can be by simultaneous administration of a single formulation (e.g., a formulation comprising the additional therapeutic agent and the AP-based agent) or of separate formulations (e.g., a first formulation including the additional therapeutic agent and a second formulation including the AP-based agent).

In a further embodiment, the additional therapeutic agent and the AP-based agent are administered to a subject simultaneously but the release of the additional therapeutic agent and the AP-based agent from their respective dosage forms (or single unit dosage form if co-formulated) may occur sequentially.

Co-administration does not require the additional therapeutic agent and the AP-based agent to be administered simultaneously, if the timing of their administration is such that the pharmacological activities of the additional therapeutic agent and the AP-based agent overlap in time. For example, the additional therapeutic agent and the AP-based agent can be administered sequentially. The term "sequentially" as used herein means that the additional therapeutic agent and the AP-based agent are administered with a time separation of more than about 60 minutes. For example, the time between the sequential administration of the additional therapeutic agent and the AP-based agent can be more than about 60 minutes, more than about 2 hours, more than about 5 hours, more than about 10 hours, more than about 1 day, more than about 2 days, more than about 3 days, or more than about 1 week apart. The optimal administration times will depend on the rates of metabolism, excretion, and/or the pharmacodynamic activity of the additional therapeutic agent and the AP-based agent being administered. Either the additional therapeutic agent or the AP-based agent may be administered first.

Co-administration also does not require the additional therapeutic agent and the AP-based agent to be administered to the subject by the same route of administration. Rather, each therapeutic agent can be administered by any appropriate route, for example, parenterally or non-parenterally.

In some embodiments, the additional therapeutic agent is an anti-bacterial agent, which includes, but is not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-bacterial agent may be any of the penicillin, cephalosporin, monobactam, and carbapenem antibiotics.

In some embodiments, the additional therapeutic agent is an adjunctive therapy that is used in, for example, the treatment of CDI. In some embodiments, the additional therapeutic agent is metronidazole (e.g. FLAGYL), fidaxomicin (e.g. DIFICID), or vancomycin (e.g. VANCOCIN), rifaximin, charcoal-based binders/adsorbents (e.g. DAV132), fecal bacteriotherapy, probiotic therapy (see, e.g., *Intnat'l J Inf Dis*, 16 (11): e786, the contents of which are hereby incorporated by reference, illustrative probiotics include *Saccharomyces boulardii; Lactobacillus rhamnosus* GG; *Lactobacillus plantarum* 299v; *Clostridium butyricum* M588*; Clostridioides difficile* VP20621 (non-toxigenic *C. difficile* strain, formerly known as *Clostridium difficile*); combination of *Lactobacillus casei, Lactobacillus acidophilus* (Bio-K+CL1285); combination of *Lactobacillus casei, Lactobacillus bulgaricus, Streptococcus thermophilus* (Actimel); combination of *Lactobacillus acidophilus, Bifidobacterium bifidum* (Florajen3); combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve, Streptococcus salivarius* subsp. *thermophilus* (VSL #3)) and antibody or other biologic therapy (e.g. monoclonal antibodies against *C. difficile* toxins A and B as described in *N Engl J Med.* 2010; 362(3):197, the content of which are hereby incorporated by reference in their entirety; neutralizing binding proteins, for example, arranged as multimers, which are directed to one or more of SEQ ID NOs. recited in United States Patent Publication No. 2013/0058962 (e.g. one or more of SEQ ID Nos.: 59, 60, 95, 67, 68, and 87), the contents of which are hereby incorporated by reference); or any neutralizing binding protein directed against *C. difficile* binary toxin.

In some embodiments, the additional therapeutic agent is an antidiarrheal agent. Antidiarrheal agents suitable for use in the present invention include, but are not limited to, DPP-IV inhibitors, natural opioids, such as tincture of opium, paregoric, and codeine, synthetic opioids, such as diphenoxylate, difenoxin and loperamide, bismuth subsalicylate, lanreotide, vapreotide and octreotide, motiln antagonists, COX2 inhibitors like celecoxib, glutamine, thalidomide and traditional antidiarrheal remedies, such as kaolin, pectin, berberine and muscarinic agents.

In some embodiments, the additional therapeutic agent is an anti-inflammatory agent such as steroidal anti-inflammatory agents or non-steroidal anti-inflammatory agents (NSAIDS). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. Additional anti-inflammatory agents are described, for example, in U.S. Pat. No. 4,537,776, the entire contents of which are incorporated by reference herein.

In some embodiments, the additional therapeutic agent may be an analgesic. Analgesics useful in the compositions and methods of the present invention include, without limitation, morphine, codeine, heroine, methadone and related compounds, thebaine, orpiavine, and their derivatives, buprenorphine, the piperidines, morphinans, benzomorphans, tetrahydroisoquinolines, thiambutanes, benzylamines, tilidine, viminol, nefopam, capsaicin(8-methyl-N-vanillyl-6E-nonenamide), "synthetic" capsaicin(N-vanillylnonamide), and related compounds.

In some embodiments, the additional therapeutic agent may be an anti-viral agent that includes, but is not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet.

In some embodiments, the additional therapeutic agent may be an agent useful for treating inflammatory bowel disease. For example, the agent may be used for treating colitis (e.g., ulcerative colitis) and Crohn's disease, which include, but are not limited to, vedolizumab (ENTYVIO), tofacitinib (XELJANZ), DIMS 0150 (KAPPAPROCT), golimumab (SIMPONI), adalimumab (HUMIRA) and other anti-TNF therapy.

In some embodiments, the additional therapeutic agent may be an agent useful for treating Celiac disease. Illustrative agents include, but are not limited to, AVX-176 (Avaxia Biologics), Actobiotics (ActoGeniX), CALY-002 (Calypso biotech), HLA-DQ2 antagonists, HLA-DQ2/DQ8 antagonists, tTG inhibitos including ERW1041E (GlaxoSmithKline) and ZED-101/ZED-1227 (Zedira), Larazotide actate (Alba Therapeutics), Latiglutenase (Alvine Pharmaceuticals), BL-7010 (BioLineRx), and NexVax-2 (ImmmunsanT).

In some embodiments, the additional therapeutic agent may be an agent useful for treating cystic fibrosis. Illustrative agents include, but are not limited to, ivacaftor (KALYDECO; Vertex), lumacaftor/ivacaftor (ORKAMBI; Vertex), VX-152 (Vertex), VX-440 (Vertex), VX-371 (Vertex), nitric oxide, glycerol phenylbutyrate, riociguat (Bayer), recombinant A1PI (Grifols, SA), cysteamine IR, JBT-101 (Corbus Pharmaceuticals), N-91115 (Nivalis Therapeutics), and vancomycin.

In some embodiments, the additional therapeutic agent is an agent useful for treating obesity. Illustrative agents include, but are not limited to, orlistat, lorcaserin, phentermine-topiramate, naltrexone-bupropion, sibutramine, rimonabant, exenatide, pramlintide, phentermine, benzphetamine, diethylpropion, phendimetrazine, bupropion, and metformin. In various embodiments, the additional agent is an agent that that interfere with the body's ability to absorb specific nutrients in food, such as orlistat, glucomannan, and guar gum. Agents that suppress appetite are also among the additional agents, e.g. catecholamines and their derivatives (such as phentermine and other amphetamine-based drugs), various anti-depressants and mood stabilizers (e.g. bupropion and topiramate), anorectics (e.g. dexedrine, digoxin). Agents that increase the body's metabolism are also among the additional agents. In some embodiments, additional agents may be selected from among appetite suppressants, neurotransmitter reuptake inhibitors, dopaminergic agonists, serotonergic agonists, modulators of GABAergic signaling, anticonvulsants, antidepressants, monoamine oxidase inhibitors, substance P (NKI) receptor antagonists, melanocortin receptor agonists and antagonists, lipase inhibitors, inhibitors of fat absorption, regulators of energy intake or metabolism, cannabinoid receptor modulators, agents for treating addiction, agents for treating metabolic syndrome, peroxisome proliferator-activated receptor (PPAR) modulators; and dipeptidyl peptidase 4 (DPP-4) antagonists. In some embodiments, additional agents may be selected from among amphetamines, benzodiazepines, sulfonyl ureas, meglitinides, thiazolidinediones, biguanides, beta-blockers, ACE inhibitors, diuretics, nitrates, calcium channel blockers, phenlermine, sibutramine, lorcaserin, cetilistat, rimonabant, taranabant, topiramate, gabapentin, valproate, vigabatrin, bupropion, tiagabine, sertraline, fluoxetine, trazodone, zonisamide, methylphenidate, varenicline, naltrexone, diethylpropion, phendimetrazine, repaglinide, nateglinide, glimepiride, pioglitazone, rosiglitazone, liraglutide, and sitagliptin.

In an embodiment, the additional therapeutic agent is an agent for treating pre-diabetes, diabetes, type II diabetes, insulin resistance, glucose intolerance, or hyperglycemia. Examples of drugs include, but are not limited to, alpha-glucosidase inhibitors, amylin analogs, dipeptidyl peptidase-4 inhibitors, GLP1 agonists, meglitinides, sulfonylureas, biguanides, thiazolidinediones (TZD), and insulin. Additional examples of such agents include bromocriptine and Welchol. Examples of alpha-glucosidase inhibitors include but are not limited to acarbose and miglitol. An example of an amylin analog is pramlintide. Examples of dipeptidyl peptidase-4 inhibitors include but are not limited to saxagliptin, sitagliptin, vildagliptin, linagliptin, and alogliptin. Examples of GLP1 agonist include but are not limited to liraglutide, exenatide, exenatide extended release. Examples of meglitinides include but are not limited to nateglinide, and repaglinide. Examples of sulfonylureas include but are not limited to chlorpropamide, glimepiride, glipizide, glyburide, tolazamide, and tolbutamide. Examples of biguanides include but are not limited to metformin, Riomet, Glucophage, Glucophage XR, Glumetza. Examples of thiazolidinedione include but are not limited to rosiglitazone and pioglitazone. Examples of insulin include but are not limited to Aspart, Detemir, Glargine, Glulisine, and Lispro. Examples of combination drugs include but are not limited to glipizide/metformin, glyburide/metformin, pioglitazone/glimepiride, pioglitazone/metformin, repaglinide/metformin, rosiglitazone/glimepiride, rosiglitazone/metformin, saxagliptin/metformin, sitagliptin/simvastatin, sitagliptin/metformin, linagliptin/metformin, alogliptin/metformin, and alogliptin/pioglitazone.

Methods of Treatment

In various embodiments, the present invention provides methods of treating or preventing a radiation-induced disorder, including, but not limited to, enterocolitis due to radiation therapy for cancer, radiation-induced enteropathy, colitis, and/or proctitis. Radiation-induced enteropathy is characterized by mucosal atrophy, vascular sclerosis, and progressive intestinal wall fibrosis. Symptoms of the disorder can include malabsorption of nutrients, altered intestinal transit, dysmotility, and abnormal propulsion of intestinal contents. In some embodiments, acute radiation-induced enteropathy occurs within the first month, first 2 months, or first 3 months after radiation exposure. In some embodiments, delayed radiation enteropathy symptoms are chronic and may not present until at least 3, at least 4, at least 5, at least 6, at least 7, at least 8, at least 9, at least 10, at least 11, or at least 12 months after radiation exposure. In some embodiments, delayed radiation enteropathy symptoms may not present until about 3, about 4, about 5, about 6, about 7, about 8, about 9, about 10, about 11, or about 12 months after radiation exposure. In some embodiments, delayed radiation enteropathy symptoms may not present until about 1 year, about 2 years, about 3 years, about 4 years, or about 5 years after radiation exposure.

In some embodiments, the present invention provides for the treatment of and/or administration of an AP-based agent to a subject that has been exposed to radiation, including, but not limited to, radiotherapy. In various embodiments, administration of the AP-based agent occurs prior to exposure to radiation, such as, for example, prior to radiotherapy as part of a cancer treatment. In certain embodiments, administration of the AP-based agent occurs at the time of radiation exposure. In various embodiments, administration of the AP-based agent occurs at the time of exposure to radiation, as well as shortly after exposure to radiation. In some embodiments, administration of the AP-based agent occurs shortly after exposure to radiation. In various embodiments, administration of the AP-based agent occurs at the time of exposure to radiation, as well as continued long term after exposure to radiation. In some embodiments, administration of the AP-based agent continues for a long term after exposure to radiation. In various embodiments, administration of the AP-based agent occurs at the onset of delayed radiation enteropathy. In some embodiments, the present invention provides for the treatment and/or administration of an AP-based agent to a subject that has been exposed to or will be exposed to radiation, where the administration of the AP-based agent occurs for at least 1 year, at least 1.5 years, at least 2 years, at least 2.5 years, at least 3 years, at least 3.5 years, 4 years, at least 4.5 years, at least 5 years, at least 5.5 years, at least 6 years, at least 6.5 years, or at least 7 years after the exposure to radiation.

In various embodiments, the present invention provides for the treatment of and/or administration to a subject who suffers from radiation-related diseases or disorder, e.g. without limitation a side effect of radiotherapy or ARS.

In some embodiments, the present invention provides for the prevention of, treatment of, and/or administration to a subject who suffers from radiation enteritis. For example, the subject may be suffering from either acute or chronic radiation enteritis. Symptoms of radiation enteritis include, but are not limited to, nausea, vomiting, stomach cramping, frequent urges to use the bathroom, watery diarrhea, mucous discharge from the rectum, rectal pain, rectal bleeding, weight loss, and wave-like stomach pains.

In some embodiments, the present invention relates to a method of treating or preventing radiation-related diseases or disorders in a subject in need thereof comprising, administering to the subject a modified-released formulation described herein, comprising an AP-based agent. For example, without limitation, the AP-based agent of the formulation is IAP, which may be administered orally.

In various embodiments, the present invention provides for the treatment of and/or administration to a subject who suffers from delayed radiation enteropathy and/or bowel toxicity. In some embodiments, the delayed radiation enteropathy occurs at least 3 months after the end of radiotherapy. In various embodiments, the radiotherapy is radiation therapy that treats cancer. In various embodiments, the subject is a cancer patient. In an embodiment, the radiation therapy is directed at tumors in the pelvis, abdomen, or lower torso. In some embodiments, the present treatment of the present invention does not interfere with the cancer treatment, including, but not limited to, radiation therapy.

In various embodiments, the radiation comprises ionizing radiation. In various embodiments, the radiation comprises one or more of X-rays, gamma rays, and charged particles.

In various embodiments, the radiation exposure is at a dose of about 2 Gy, or about 2.5 Gy, or about 3 Gy, or about 3.5 Gy, or about 4 Gy, or about 4.5 Gy, or about 5 Gy, or about 10 Gy, about 20 Gy, or about 30 Gy, or about 40 Gy, or about 50 Gy, or about 60 Gy, or about 70 Gy, or about 80 Gy, or about 90 Gy, or about 100 Gy.

In various embodiments, the radiation exposure is local or whole body.

In some embodiments, the present invention relates to a method of treating or preventing radiation-related diseases or disorders in a subject in need thereof comprising, administering to the subject a modified-release formulation described herein comprising an AP-based agent, optionally IAP, which may be administered orally where the radiation-related disease or disorder is a result of or side effect of radiotherapy.

In some embodiments, the present methods pertain to prevention or reduction of reduced diversity in the gut microbiome, e.g. that is a side effect or result of radiation exposure (including radiotherapy) and/or chemotherapy. In some embodiments, the present methods relate to repairing and/or repopulating the gut microbiome of a subject after radiation exposure (including radiotherapy) and/or chemotherapy.

In some embodiments, the radiotherapy may be part of a cancer treatment, as a primary or adjuvant therapy (e.g. with chemotherapy). In some embodiments, the radiotherapy may be used to prevent tumor recurrence after surgery and/or to remove a primary malignant tumor. In various embodiments, the subject is a cancer patient.

In some embodiments, the radiotherapy may be part of a treatment for Dupuytren's disease, Ledderhose disease, or as part of a post-surgery treatment. In various embodiments, the subject is afflicted with Dupuytren's disease, Ledderhose disease, or has recently undergone surgery.

In various embodiments, the present methods reduce or eliminate a side effect of radiotherapy, including acute side effects, long-term side effects), or cumulative side effects. In various embodiments, the present methods reduce or eliminate a local or systemic side effect of radiotherapy. In various embodiments, the side effect of radiotherapy is one or more of fatigue, nausea and vomiting, damage to the epithelial surfaces (e.g., without limitation, moist desquamation), Mouth, throat and stomach sores, Intestinal discomfort (e.g., without limitation, soreness, diarrhea, and nausea), swelling, infertility, fibrosis, epilation, dryness (e.g. without limitation, dry mouth (xerostomia) and dry eyes (xerophthalmia), and dryness of the armpit and vaginal mucosa), lymphedema, heart disease, cognitive decline, radiation enteropathy (e.g. without limitation, atrophy, fibrosis and vascular changes, which may produce malabsorption, diarrhea, steatorrhea and bleeding with bile acid diarrhea and vitamin B12 malabsorption commonly found due to ileal involvement. Pelvic radiation disease includes radiation proctitis, producing bleeding, diarrhoea and urgency, and radiation cystitis.

In various embodiments, the radiotherapy is pelvic radiotherapy. In such embodiments, the modified-release formulation described herein comprising an AP-based agent, optionally IAP, which may be administered orally, reduces or eliminates GI-related side effects as described herein. In such embodiments, the AP-based agent, optionally IAP, which may be administered orally, reduces or eliminates lower body-related side effects as described herein.

In various embodiments, the radiotherapy is pelvic radiotherapy, and the modified-release formulation described herein, reduces or eliminates one or more of radiation enteropathy, atrophy, fibrosis and vascular changes, malabsorption, diarrhea, steatorrhea, bleeding with bile acid diarrhea, malabsorption (e.g. vitamin malabsorption, e.g. vitamin B12 malabsorption). In various embodiments, the radiotherapy is pelvic radiotherapy, and the modified-release formulation described herein reduces or eliminates radiation proctitis, producing bleeding, diarrhoea and urgency, and radiation cystitis.

In various embodiments, the radiotherapy is delivered as one or more of external-beam radiation therapy, brachytherapy, and systemic radiation therapy.

In various embodiments, the radiotherapy is an external-beam radiation therapy, selected from 3-dimensional conformal radiation therapy (3D-CRT), intensity-modulated radiation therapy (IMRT, e.g. RAPIDARC), image-guided radiation therapy (IGRT), electromagnetic-guided radiation therapy (e.g. CALYPSO) tomotherapy, stereotactic radiosurgery (SRS), stereotactic body radiation therapy (SBRT, e.g. CYBERKNIFE, GAMMAKNIFE, X-KNIFE, CLINAC), Intraoperative radiation therapy (IORT), and proton therapy.

In various embodiments, the radiotherapy is a brachytherapy, selected from interstitial brachytherapy, intracavitary brachytherapy, episcleral brachytherapy, In various embodiments, the radiotherapy is a systemic radiation therapy, selected from a radioactive iodine and a radioactive biologic. For example, the radiotherapy may be radioactive iodine (1311), ibritumomab tiuxetan (ZEVALIN), tositumomab and iodine I 131 tositumomab (BEXXAR), samarium-153-lexidronam (QUADRAMET), and strontium-89 chloride (METASTRON).

In various embodiments, the radiotherapy comprises a dose of about 20 Gy, or about 30 Gy, or about 40 Gy, or about 50 Gy, or about 60 Gy, or about 70 Gy, or about 80 Gy, or about 90 Gy, or about 100 Gy, optionally fractionated.

In some embodiments, the present invention relates to a method of treating or preventing radiation-related diseases or disorders in a subject in need thereof comprising, administering to the subject a modified-release formulation described herein, where the radiation-related disease or disorder is acute radiation syndrome.

In some embodiments, ARS comprises one of more of gastrointestinal syndrome; hematopoietic syndrome; neurovascular syndrome; apoptosis-mediated tissue damage, wherein the apoptosis is optionally attributable to cellular stress; and ionizing radiation induced apoptosis tissue damage. In some embodiments, the high dose of radiation (e.g. ionizing radiation) is about 5 to about 30 Gy, or about 10 to about 25 Gy, or about 15 to about 20 Gy and, optionally, sufficient for a classification of Unit Radiation Exposure Status of RES 3. In various embodiments, the high dose of radiation is the result of a radiation disaster and/or the human patient being treated has been exposed to or is at risk of being exposed to a high dose of radiation as a result of one or more of a military operation or a first responder operation in a contaminated area; a nuclear explosion; a criticality accident; a radiotherapy accident; a terrorist attack; exposure from space travel; escape of radioactive waste; exposure to open source radiation; and a nuclear reactor malfunction.

In various embodiments, the present methods and compositions provide treatment or prevention of radiation-related disorders, such as ARS. In various embodiments, the treatments described herein reduce morbidity or mortality of an exposed population of human patients and/or accelerates recovery from symptoms of ARS. ARS often presents as a sequence of phased symptoms, which may vary with individual radiation sensitivity, type of radiation, and the radiation dose absorbed. Generally, without wishing to be bound by theory, the extent of symptoms will heighten and the duration of each phase will shorten with increasing radiation dose. ARS can be divided into three phases: prodromal phase (a.k.a. N-V-D stage), latent period and manifest illness. In various embodiments, an AP-based agent modified-release formulation of the present invention may be administered to a human patient in any one of these three stages (i.e. the AP-based agent may be administered to a human patient in the prodromal phase, the AP-based agent may be administered to a human patient in latent period, or the AP-based agent may be administered to a human patient in manifest illness stage).

In the prodromal phase there is often a relatively rapid onset of nausea, vomiting, and malaise. Use of antiemetics, (e.g. oral prophylactic antiemetics) such as granisetron (KYTRIL), ondansetron (ZOFRAN), and 5-HT3 blockers with or without dexamethasone, may be indicated in situations where high-dose radiological exposure has occurred, is likely, or is unavoidable. Accordingly, in various embodiments, the AP-based agent may be administered to a human patient in receiving an anti-emetic agent or the AP-based agent may be administered to a human patient in combination with an anti-emetic agent. For example, the AP-based agent may also be added to the following antiemetic regimens: Ondansetron: initially 0.15 mg/kg IV; a continuous IV dose option consists of 8 mg followed by 1 mg/h for the next 24 hours. Oral dose is 8 mg every 8 hours as needed or Granisetron (oral dosage form): dose is usually 1 mg initially, and repeated 12 hours after the first dose. Alternatively, 2 mg may be taken as one dose. IV dose is based on body weight; typically 10 μg/kg (4.5 μg/lb) of body weight.

In the latent period, a human patient may be relatively symptom-free. The length of this phase varies with the dose. The latent phase is longest preceding the bone-marrow depression of the hematopoietic syndrome and may vary between about 2 and 6 weeks. The latent period is somewhat shorter prior to the gastrointestinal syndrome, lasting from a few days to a week. It is shortest of all preceding the neurovascular syndrome, lasting only a matter of hours. These times are variable and may be modified by the presence of other disease or injury. Manifest illness presents with the clinical symptoms associated with the major organ system injured (marrow, intestinal, neurovascular).

In some embodiments, the present invention relates to the mitigation of, or protection of cells from, the effects of exposure to radiation. In some embodiments, the present invention pertains to a method of mitigating and/or protecting a human patient from radiation comprising administering the AP-based agent described herein. In some embodiments, the radiation is ionizing radiation. In some embodiments, the ionizing radiation is sufficient to cause gastrointestinal syndrome or hematopoietic syndrome.

In some embodiments, the ARS comprises one of more of gastrointestinal syndrome; hematopoietic syndrome; neurovascular syndrome; apoptosis-mediated tissue damage, wherein the apoptosis is optionally attributable to cellular stress; and ionizing radiation induced apoptosis tissue damage.

Hematopoietic syndrome (a.k.a. bone marrow syndrome) is characterized by loss of hematopoietic cells and their progenitors making it impossible to regenerate blood and lymphoid system. This syndrome is often marked by a drop in the number of blood cells, i.e., aplastic anemia. This may result in infections (e.g. opportunistic infections) due to a low amount of white blood cells, bleeding due to a lack of platelets, and anemia due to few red blood cells in the circulation. These changes can be detected by blood tests after receiving a whole-body acute dose. Conventional trauma and burns resulting from a bomb blast are complicated by the poor wound healing caused by hematopoietic syndrome, increasing mortality. Death may occur as a consequence of infection (e.g. as a result of immunosuppression), hemorrhage and/or anemia. Hematopoietic syndrome usually prevails at the lower doses of radiation and leads to the more delayed death than GI syndrome.

Gastrointestinal syndrome is caused by massive cell death in the intestinal epithelium, predominantly in the small intestine, followed by disintegration of intestinal wall and death from bacteriemia and sepsis. Symptoms of this form of radiation injury include nausea, vomiting, loss of appetite, loss of absorptive capacity, hemorrhage in denuded areas, and abdominal pain. Illustrative systemic effects of gastrointestinal syndrome include malnutrition, dehydration, renal failure, anemia, sepsis, etc. Without treatment (including, for example, bone marrow transplant), death is common (e.g. via infection from intestinal bacteria). In some embodiments, the AP-based agent may be used in combination with bone marrow transplant. In some embodiments, the AP-based agent may be used in combination with one or more inhibitors of GI syndrome and/or any of the additional agents described herein.

Neurovascular syndrome presents with neurological symptoms such as dizziness, headache, or decreased level of consciousness, occurring within minutes to a few hours, and with an absence of vomiting. Additional symptoms include extreme nervousness and confusion; severe nausea, vomiting, and watery diarrhea; loss of consciousness; and burning sensations of the skin. Neurovascular syndrome is commonly fatal.

In various embodiments, methods and compositions of the present invention provide treatment and/or prevention of radiation-induced intestinal fibrosis. In some embodiments, radiation-induced intestinal fibrosis comprises one or more of bowel inflammation, bowel fibrosis, vascular sclerosis, chronic ulcers, enlargement of submucosa, enhanced fibroblast and smooth muscle cell proliferation, and excessive deposition of collagen and other extracellular matric components.

In some embodiments, the present invention provides a method for reducing the risk of death following exposure to irradiation comprising administering an effective amount of the AP-based agent. In some embodiments, the radiation is potentially lethal, and, optionally, occurs as the result of a radiation disaster. In various embodiments, the AP-based agent is administered within 24 hours following radiation exposure. In various embodiments, the AP-based agent is administered within 48 hours following radiation exposure.

In some embodiments, the AP-based agent modified-release formulation is administered in combination with any additional agent described herein, including but not limited to a radioprotectant (e.g. an antioxidant (e.g. amifostine and vitamin E), a cytokine (e.g. a stem cell factor)), etc. Injury and death of normal cells from ionizing radiation is a combination of a direct radiation-induced damage to the exposed cells and an active genetically programmed cell reaction to radiation-induced stress resulting in a suicidal death or apoptosis. Apoptosis plays a key role in massive cell loss occurring in several radiosensitive organs (e.g., hematopoietic and immune systems, epithelium of digestive tract, etc.), the failure of which determines general radiosensitivity of the organism. In some embodiments, administration of the AP-based agent of the invention to a human patient in need thereof suppresses apoptosis in cells. In some embodiments, the AP-based agent of the invention are administered to a human patient to protect healthy cells from the damaging effects of the radiation treatment.

In various embodiments, the present invention provides a method for reducing apoptosis following exposure to irradiation. In an embodiment, the present invention provides a method for reducing apoptosis of hematopoietic cells following irradiation. In another embodiment, the present invention provides a method for reducing apoptosis of gastrointestinal cells following irradiation.

In various embodiments, administration of the AP-based agent stimulates and protects stem cells. For example, the present invention and composition may stimulate and protect hematopoietic stem cells including various hematopoietic progenitor cells. In another example, the present invention and composition may stimulate and protect gastrointestinal stem cells such as intestinal crypt stem cells. In some embodiments, the stem cells may be stimulated to proliferate and regenerate. Accordingly, the present invention provides methods of expanding the number of stem cells such as hematopoietic stem cells or gastrointestinal stem cells in a patient. In some embodiments, hematopoietic progenitor cells or gastrointestinal progenitor cells are expanded. In various embodiments, the present invention provides methods and compositions that protect the stem cells or progenitors cells from cell death (e.g., apoptosis or necrosis).

In various embodiments, methods and compositions of the present invention significantly enhances recovery of the hematopoietic and GI systems following irradiation. For example, methods and compositions of the present invention enhance bone marrow recovery following irradiation. In another example, methods and compositions of the present invention enhances regeneration of the GI crypt.

Exposure to ionizing radiation (IR) may be short- or long-term, and/or it may be experienced as a single or multiple doses and/or it may be applied to the whole body or locally. The present invention, in some embodiments, pertains to nuclear accidents or military attacks, which may involve exposure to a single high dose of whole body irradiation (sometimes followed by a long-term poisoning with radioactive isotopes), as further described herein. The same is true (with strict control of the applied dose), for example, for pretreatment of patients for bone marrow transplantation when it is necessary to prepare hematopoietic organs for donor's bone marrow by "cleaning" them from the host blood precursors. Cancer treatment may involve multiple doses of local irradiation that greatly exceeds lethal dose if it were applied as a total body irradiation (e.g. a radiotherapy accident). Poisoning or treatment with radioactive isotopes results in a long-term local exposure to radiation of targeted organs (e.g., thyroid gland in the case of inhalation of 1251). Further, there are many physical forms of ionizing radiation differing significantly in the severity of biological effects.

At the molecular and cellular level, radiation particles are able to produce breakage and cross-linking in the DNA, proteins, cell membranes and other macromolecular structures. Ionizing radiation also induces the secondary damage to the cellular components by giving rise to the free radicals and reactive oxygen species (ROS). Multiple repair systems counteract this damage, such as, several DNA repair pathways that restore the integrity and fidelity of the DNA, and antioxidant chemicals and enzymes that scavenge the free radicals and ROS and reduce the oxidized proteins and lipids. Cellular checkpoint systems detect the DNA defects and delay cell cycle progression until damage is repaired or decision to commit cell to growth arrest or programmed cell death (apoptosis) is reached Radiation can cause damage to mammalian organism ranging from mild mutagenic and carcinogenic effects of low doses to almost instant killing by high doses. Overall radiosensitivity of the organism is determined by pathological alterations developed in several sensitive tissues that include hematopoietic system, reproductive system and different epithelia with high rate of cell turnover.

Acute pathological outcome of gamma irradiation leading to death is different for different doses and may be determined by the failure of certain organs that define the threshold of organism's sensitivity to each particular dose. Thus, lethality at lower doses occurs from bone marrow aplasia, while moderate doses kill faster by inducing a gastrointestinal (GI) syndrome. Very high doses of radiation can cause almost instant death eliciting neuronal degeneration. Organisms that survive a period of acute toxicity of radiation can suffer from long-term remote consequences that include radiation-induced carcinogenesis and fibrosis developing in exposed organs (e.g., kidney, liver or lungs) in the months and years after irradiation. Cellular DNA is a major target of IR that causes a variety of types of DNA damage (genotoxic stress) by direct and indirect (e.g. free radical-based) mechanisms. All organisms maintain DNA repair system capable of effective recovery of radiation-damaged DNA; errors in DNA repair process may lead to mutations.

The AP-based agent possesses strong pro-survival activity at the cellular level and on the organism as a whole. In response to super-lethal doses of radiation, the AP-based agent may inhibit both gastrointestinal and hematopoietic syndromes, which are major causes of death from acute radiation exposure. As a result of these properties, the AP-based agent may be used to treat the effects of natural radiation events and nuclear accidents. Moreover, the AP-based agent can be used in combination with other radio-protectants, thereby, dramatically increasing the scale of protection from ionizing radiation.

The AP-based agent may be used as a radioprotective agent to extend the range of tolerable radiation doses by, for example, increasing radioresistance of human organism beyond the levels achievable by currently available measures (shielding and application of existing bioprotective agents) and drastically increase the chances of crew survival in case of nuclear accidents or large-scale solar particle events, for example.

The AP-based agent may inhibit radiation-induced programmed cell death or apoptosis in response to damage in DNA and other cellular structures. In some embodiments, the AP-based agent may not deal with damage at the cellular level and may not prevent mutations. Free radicals and reactive oxygen species (ROS) are the major cause of mutations and other intracellular damage. Antioxidants and free radical scavengers are effective at preventing damage by free radicals.

Further, in some embodiments, the present invention relates to the prevention or treatment of cutaneous radiation syndrome (CRS), i.e. skin symptoms of radiation exposure (e.g. redness (optionally associated with itching), blistering, ulceration, hair loss, damaged sebaceous and sweat glands, atrophy, fibrosis, decreased or increased skin pigmentation, ulceration or necrosis of the exposed tissue moist desquamation and collapse of the dermal vascular system after two months, resulting in the loss of the full thickness of the exposed skin.

In various embodiments, administration of the AP-based agent reduces the incidence of wounds, septic complications, and microbial infections in patients following irradiation.

In some embodiments, the present human patients experience leukopenia and/or neutropenia (e.g. absolute neutrophil count (ANC)<100 cells/μL. In some embodiments, the present methods and compositions pertain to a human patient which presents a lymphocyte count reduction of about 50% within about 24 to about 48 hours. In some embodiments, the human patient's lymphocyte count is less than about 1000 cells/μL, or about 900 cells/μL, or about 800 cells/μL, or about 700 cells/μL, or about 600 cells/μL, or about 500 cells/μL, or about 400 cells/μL, or about 300 cells/μL, or about 200 cells/μL, or about 100/cells NL (e.g. within about 24 to about 48 hours). In some embodiments, the patient's lymphocyte profile is assessed by the Andrews Lymphocyte Nomogram (see Andrews G A, Auxier J A, Lushbaugh C C. The Importance of Dosimetry to the Medical Management of Persons Exposed to High Levels of Radiation. In Personal Dosimetry for Radiation Accidents. Vienna: International Atomic Energy Agency; 1965, the contents of which are hereby incorporated by reference). In some embodiments, the present methods and compositions pertain to a human patient which presents a thrombocyte count reduction of about 50% within about 24 to about 48 hours. In some embodiments, the present human patients experience thrombocytopenia, anemia, and/or neutropenia. Thrombocytopenia is defined as a platelet count of below 50,000/μL. For example, thrombocytopenia may be characterized as grade 1 thrombocytopenia (i.e., platelet count of 75,000 to 150,000/μL), grade 2 (i.e., platelet count of 50,000 to <75,000NL), grade 3 (platelet count of 25,000 to <50,000/μL), or grade 4 (i.e., platelet count of below 25,000/μL). Anemia may be diagnosed in men as having a hemoglobin content of less than 13 to 14 g/dL and in women as having a hemoglobin content of 12 to 13 g/dL. For example, anemia is divided into various grades based on hemoglobin levels: grade 0 (within normal limits, ≥12 g/dL); grade 1 (mild, 11.9 to 10 g/dL); grade 2 (moderate, 9.9 to 8 g/dL); grade 3 (serious/severe, 7.9 to 6.5 g/dL); and grade 4 (life-threatening, <6.5 g/dL). Neutropenia may be defined as having an absolute neutrophil count (ANC) of less than 1,500 cells/mm3. For example, neutropenia is graded as grade 1 (i.e., ANC of 1,500/mm3 or less to more than 2,000/mm3), grade 2 (ANC of 1,000/mm3 or less to more than 1,500/mm3), grade 3 (ANC of 500/mm3 or less to more than 1,000/mm3), or grade 4 (ANC of less than 500/mm3). In various embodiments, the present methods and compositions reduces the duration and severity of thrombocytopenia, anemia, and/or neutropenia in a patient following irradiation. For example, the present methods and compositions may reduce the duration and severity of Grade 4 thrombocytopenia, anemia, and/or neutropenia in a patient following irradiation.

In various embodiments, the high dose of radiation refers to a whole body dose. In various embodiments, the high dose of radiation may not be uniform. In various embodiments, the ARS is a result of a high dose of radiation. In various embodiments, the high dose of radiation is about 2 Gy, or about 2.5 Gy, or about 3 Gy, or about 3.5 Gy, or about 4 Gy, or about 4.5 Gy, or about 5 Gy, or about 10 Gy, or about 15 Gy, or about 20 Gy, or about 25 Gy, or about 30 Gy. In various embodiments, the high dose of radiation is about 5 to about 30 Gy, or about 10 to 25 Gy, or about 15 to 20 Gy. In some embodiments, the high dose of radiation is assessed by one or more of physical dosimetry and/or biological dosimetry (e.g. multiparameter dose assessments), cytogenics (e.g. chromosomal analysis for, for example, blood samples (including, by way of non-limiting example, dicentric analysis).

In various embodiments, whole-body radiation doses can be divided into sublethal (<2 Gy), potentially lethal (2-10 Gy), and supralethal (>10 Gy).

The radiation exposure status (RES) of a given unit is based on the operational exposure above normal background radiation. It is designed to be an average, based upon unit-level dosimeters. In various embodiments, the high dose of radiation is sufficient for a classification of Unit Radiation Exposure Status of RES 3.

In various embodiments, the radiation is ionizing radiation (e.g. one or more of alpha particles, beta particles, gamma rays, and neutrons) In various embodiments, when radiation interacts with atoms, energy is deposited, resulting in ionization (electron excitation). This ionization may damage certain critical molecules or structures in a cell by direct and indirect action. The radiation may directly hit a particularly sensitive atom or molecule in the cell. The damage from this is irreparable; the cell either dies or is caused to malfunction. The radiation also can damage a cell indirectly by interacting with water molecules in the body. The energy deposited in the water leads to the creation of unstable, toxic hyperoxide molecules; these then damage sensitive molecules and afflict subcellular structures.

In some embodiments, the radiation may be caused by one or more of the following radioactive materials: Americium (e.g. 241Am), Cesium (e.g. 137Cs), Cobalt (e.g. 60 Co), Uranium (e.g. depleted Uranium), Iodine (e.g. 131, 132, 134, 1351), Phosphorus (e.g. 32P), Plutonium (e.g. 238, 239Pu), Radium (e.g. 226Ra), Strontium (e.g. 90Sr), Tritium (e.g. 3H), and Uranium (e.g. 235U, 238U, 239U).

In various embodiments, the high dose of radiation is the result of a radiation disaster. In various embodiments, the human patient is been exposed or is at risk of being exposed to a high dose of radiation, which may be a result of one or more of a military operation or a first responder operation in a contaminated area; a nuclear explosion; a criticality accident; a radiotherapy accident; a terrorist attack; exposure from space travel; escape of radioactive waste; exposure to open source radiation; and a nuclear reactor malfunction.

A method of treating or preventing a side effect of a chemotherapeutic treatment in a subject in need thereof comprising, administering to the subject a modified-release formulation described herein.

In various embodiments, the present invention provides for the treatment of and/or administration to a subject who suffers from a side effect of a chemotherapeutic treatment.

In some embodiments, the side effect of a chemotherapeutic treatment is selected from alopecia, myelosuppression, renal toxicity, weight loss, pain, nausea, vomiting, diarrhea, constipation, anemia, malnutrition, hair loss, numbness, changes in tastes, loss of appetite, thinned or brittle hair, mouth sores, memory loss, hemorrhage, cardiotoxicity, hepatotoxicity, ototoxicity, and post-chemotherapy cognitive impairment.

A method of treating a cancer by improving the effectiveness of a chemotherapeutic treatment in a subject in need thereof comprising, administering to the subject a modified-release formulation described herein. In various embodiments, the AP-based agent modified-release formulation described herein acts as an adjuvant to a chemotherapeutic treatment described herein. In various embodiments, the AP-based agent modified-release formulation described herein described herein improves the anti-cancer effect and/or increases the therapeutic window of any of the chemotherapeutic treatments described herein. In various embodiments, administering to the subject an AP-based agent modified-release formulation does not interfere with treatment of cancer.

The present invention further provides, in certain aspects, methods of improving or reducing and/or treating or preventing frailty in a subject, where the method includes: identifying a subject desiring or in need of frailty treatment or prevention, and administering to the subject an AP-based agent modified-release formulation described herein.

Aging is a gradual systemic pathological transformation of mammalian organism advancing with time. It is associated with accumulation of multiple deficiencies in functions of multiple organs and tissues and reduced regeneration capabilities leading to development of age-related chronic diseases or disorders including atherosclerosis, diabetes, pulmonary fibrosis, blindness, dementia, kidney dysfunction, osteoarthritis, and low grade chronic sterile inflammation as well as other age-related diseases and disorders contemplated herein. These conditions frequently coincide with a gradual development of geriatric syndromes including frailty, cognitive impairment and immobility. Aging is a natural and unavoidable process. Underlying causes of aging are still disputable; however, two features of aging are generally accepted as universal: an increase in DNA damage and development of systemic sterile chronic inflammation, both considered as major contributors of age-related pathologies.

In some embodiments, the present invention provides methods of improving or reducing and/or treating or preventing frailty in a subject, as measured by a reduction in the PFI score of the subject. In some embodiments, methods and compositions of the present invention for improving or reducing and/or treating or preventing frailty in a subject include maintaining a PFI score over time so that the score increases at a rate slower than if the subject were not being administered the AP-based agent modified-release formulation of the invention. In some embodiments of the present invention, the PFI score of the patient remains nearly the same over time. In further embodiments, methods of the present invention provide for a reduction in cellular senescence and immunosenescence associated with natural aging and/or accelerated aging (e.g., accelerated aging induced by, e.g., cancer or a cancer treatment).

In another aspect, the present invention provides for methods of treating or preventing an age-related disease or disorder in a subject, where the method includes: identifying a subject desiring or in need of treatment or prevention of an age-related disease or disorder, and administering to said subject an AP-based agent modified-release formulation. In some embodiments, the age-related disease or disorder is characterized by increased cellular senescence or immunosenescence.

In some embodiments, an age-related disease or disorder is selected from accelerated aging, cardiovascular disease, cerebrovascular disease, peripheral vascular disease, cardiac diastolic dysfunction, benign prostatic hypertrophy, aortic aneurysm, emphysema, atherosclerosis, diabetes, pulmonary fibrosis, blindness, dementia, Alzheimer's disease, kidney dysfunction, osteoarthritis, low grade chronic sterile inflammation, herniated intervertebral disc, frailty, hair loss, hearing loss, vision loss, muscle fatigue, skin conditions, skin nevi, wrinkly skin, hyperpigmentation, scarring, keloid, rosacea, vitiligo, ichthyosis vulgaris, dermatomyositis, actinic keratosis, and sarcopenia.

In specific embodiments, methods of the present invention include treating or preventing accelerated aging. In some embodiments, accelerated aging is a Progeroid syndrome or symptom thereof, including, but not limited to, Hutchinson-Gilford progeria syndrome (HGPS), Werner syndrome (WS), Bloom syndrome (BS), Rothmund-Thomson syndrome (RTS), Cockayne syndrome (CS), xeroderma pigmentosum (XP), trichothiodystrophy (TTD), combined xeroderma pigmentosum-Cockayne syndrome (XP-CS), or restrictive dermopathy (RD). Subjects having one of these diseases or disorders typically have reduced longevity (i.e., lifespan).

In further embodiments, accelerated aging is induced by a cancer or a cancer treatment. For example, it is contemplated by the invention that a cancer treatment that induces an acceleration in the natural aging process is selected from one or more therapies consisting of radiotherapy, hormonal, tyrosine kinase inhibitor, anthracycline, alkylating agent, topoisomerase inhibitor, antimetabolites/cytotoxic drug, BRAF inhibitor, antitumor antibiotic, isoquinololine alkaloid, Bcl-2 inhibitor, hematopoietic cell transplantation (HCT), telomerase inhibitor, nucleoside analogue reverse-transcriptase inhibitor, DNA cross-linking agent, ribonucleotide reductase inhibitor, microtubule inhibitor, and miRNA.

In some embodiments, any cancer is contemplated for which the subject receives treatment that can induce accelerated aging. In an embodiment, the cancer for which a subject receives treatment is hematological cancer. Further, in some embodiments, the subject received the cancer treatment during childhood.

In some embodiments, frailty comprises an accumulation of deficiencies in major physiological functions, reduction of regeneration capabilities, impaired wound healing and increased risk of age-related diseases. For example, in some embodiments, frailty is associated with natural aging or accelerated aging. Frailty can be measured according to any number of indices or tests known to one of skill in the art. For example, one such index, the Physiological Frailty Index (PFI), includes measurement of one or more parameters selected from grip strength, systolic blood pressure, diastolic blood pressure, blood flow volume, number of blood neutrophils, percentage of blood neutrophils, number of blood monocytes, percentage of blood monocytes, number of lymphocytes, number of red blood cells, hemoglobin levels, hematocrit levels, mean corpuscular volume, mean corpuscular hemoglobin levels, mean corpuscular hemoglobin concentration and keratinocyte-derived cytokine levels. Deviation from a reference standard in any one individual is known as a deficit, and the overall average PFI score of the individual is a ratio of deficits to the total number of parameters measured.

Frailty can manifest as vulnerability to stressors and a reduced capacity to withstand stress. For example, the disclosure of Buchner and Wagner 1992 Clin Geriatr Med. 1992 February; 8(1):1-17 is hereby incorporated by reference in its entirety. Frailty can manifest as loss of complexity of homeostatic mechanisms (e.g., interconnectedness and/or feedback or feedforward). For example, the disclosure of Lipsitz 2002 J Gerontol A Biol Sci Med Sci. 2002 March; 57(3):B115-25. is hereby incorporated by reference in its entirety. Frailty can also manifest as disuse and/or a decrease in energy flow through an organism, as described in Bortz 2002, J Gerontol A Biol Sci Med Sci. 2002 May; 57(5):M283-8. which is hereby incorporated by reference in its entirety. Frailty can also manifest as homeostatic dysregulation, as described by Ferrucci 2005 J. Gerontol. A Biol. Sci. Med. Sci. 60, 56, which is hereby incorporated by reference in its entirety.

There are several comprehensive approaches for quantitative assessment of aging-related accumulation of deficits and frailty in humans and animals. Individual organisms are heterogeneous in their health status and the rate of aging. To account for such heterogeneity, a Frailty Index (FI) has been introduced as a numerical score which is a ratio of the deficits present in a person to the total number of deficits considered in the study. Changes in the FI characterize the rate of individual aging. A similar approach has been applied to laboratory animals. Frailty index is considered as a reliable and broadly accepted measure of "biological age" and the degree of general health decline indicative of a reduction in the quality of life.

In certain aspects and embodiments, provided herein includes methods for improving and/or treating or preventing frailty and/or reducing frailty index in a subject. Frailty can be assessed in any of many methods known in the art. For example, frailty and methods to evaluate/index frailty are described in Hubbard, et al., Ageing, published electronically November, 2008 page 115-118; Cesari, et al., Age and Ageing, 43:10-12, 2014; and Mohler et al., Experimental Gerontology, 54:6-13, 2014, all of which are hereby incorporated by reference.

In various embodiments, a Frailty Index is calculated as described in U.S. Patent Application Publication No. 2015/0285823, which is incorporated herein by reference. For example, a description of the determination of the Frailty Index is provided. The Frailty Index was developed to assess a fit to frail range for the organisms of the same chronological age to address the notion that chronological age does not always reflect biologic age. Based on sixteen-item parameters (that include measurements of weight, grip strength, blood pressure, complete blood count, cytokine level analysis), FI is calculated as a ratio of the total number of deficits measured and are assigned a score of FI between 0 (no deficits=fit) and 1 (all deficits present=frail). Therefore, higher FI indicates poorer health of an organism. In this regard, a FI is provided as a useful tool for assessing a "fit" to "frail" range organisms of the same chronological age.

In certain embodiments, methods of the present invention reduce or prevent frailty in a subject as measured according to the Physiological Frailty Index (PFI), as described in Antoch et al. Aging. 2017; 9: 1-12 (hereby incorporated by reference in its entirety). For example, PFI can be determined for an individual subject with reference to a young reference subject. For each subject, various parameters are measured. These parameters include non-invasive measurements, including age, body weight, grip strength, and diastolic blood pressure. Additional blood chemistry measurements may also be determined, including white blood cell count, neutrophil count, neutrophil percentage, lymphocyte percentage, monocyte percentage, eosinophil percentage, red blood cell count, hemoglobin levels, hematocrit levels, mean corpuscular volume, mean corpuscular hemoglobin levels, mean corpuscular hemoglobin concentration, platelet count, and mean platelet volume. For each parameter mean value and standard deviation are calculated. Subjects differing in more than one standard deviation (STDEV) from mean value in any single parameter are excluded from the reference group. The value for each parameter measured for subjects of older ages is compared with the corresponding value for the reference group and assigned a score. Values that differ less than 1 STDEV are assigned the score of 0 (no deficit, within the range of the reference group). Values that are different for one STDEV are scored as 0.25 (minimal deficit). Values that differ from the corresponding values in the reference group by 2 STDEV are scored as 0.5 and those that differ by 3 STDEV are scored as 0.75. If the value is above 3 STDEV, it is scored as 1 (extreme deficit). The number of deficits the individual subject expressed is calculated as a ratio of the total number of parameters measured and is referred to as Physiological Frailty Index (PFI).

In some embodiments, methods of the present invention reduce or improve and/or treat or prevent frailty in a subject, as measured by the PFI. For example, administering the AP-based agent modified-release formulation to a subject in order to reduce or improve and/or treat or prevent frailty can result in a reduced PFI score. In some embodiments, a subject's PFI score is reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In some embodiments, a subject's PFI score is reduced by about 25%-75%, about 25%-50%, or about 50% to 75%. In further embodiments, a subject's PFI score is reduced to no greater than 0.9, 0.85, 0.8, 0.75, 0.7, 0.65, 0.6, 0.55, 0.5, 0.45, 0.4, 0.35, 0.3, 0.25, 0.2, 0.15, 0.1 or 0.5.

Further, frailty as an accumulation of deficits can be measured by the Rockwood frailty index, as described in Rockwood et al., J Gerontol A Biol Sci Med Sci. 2007 July; 62(7):722-727, which is incorporated by reference in its entirety. In embodiments, the present methods reduce or prevent frailty as assessed by the Rockwood frailty index.

Frailty as a biologic syndrome of decreased reserve resulting from cumulative declines across multiple physiologic systems can be measured by the Fried frailty score, as described in Fried et al., J Gerontol A Biol Sci Med Sci. 2001 March; 56(3):M146-56, which is incorporated by reference in its entirety. The Fried frailty score comprises a Physical Frailty Phenotype (PFP), which measures various parameters, such as weight loss of more than 10 pounds; weakness as related to grip strength; self-reported exhaustion; 15 feet walking speed; and amount of physical activity in Kcals per week. The Fried frailty score incorporates scoring of 0 (not frail), 1-2 (intermediate frailty), and greater than or equal to 3 (frail). In various embodiments, methods of the present invention reduce or improve and/or treat or prevent frailty in a subject, as measured by a Fried frailty score. For example, administering the AP-based agent modified-release formulation to a subject in order to reduce or improve and/or treat or prevent frailty can result in a reduced Fried frailty score from 3 to 2, from 3 to 1, from 3 to 0, from 2 to 1, from 2 to 0 or from 1 to 0. Further, in some embodiments, administering the AP-based agent modified-release formulation to a subject in order to reduce or improve and/or treat or prevent frailty results in a lack of increase of a subject's Fried frailty score.

Frailty can also be measured by the FRAIL Scale, as described in Abellean Van Kan et al., J Am Med Dir Assoc. 2008 February; 9(2):71-2. doi: 10.1016/j.jamda.2007.11.005, which is incorporated by reference in its entirety. The parameters measured in the FRAIL Scale include feelings of persistent fatigue; resistance (ability to climb a single flight of stairs); ambulation (ability to walk one block); more than five illnesses; and more than 5% loss of weight. The FRAIL Scale incorporates scoring of 0 (not frail), 1-2 (intermediate frailty), and greater than or equal to 3 (frail). In various embodiments, methods of the present invention reduce or improve frailty in a subject, as measured by a FRAIL Scale score. For example, administering the AP-based agent modified-release formulation to a subject in order to reduce or improve frailty can result in a reduced FRAIL Scale score from 3 to 2, from 3 to 1, from 3 to 0, from 2 to 1, from 2 to 0 or from 1 to 0. Further, in some embodiments, administering the AP-based agent modified-release formulation to a subject in order to reduce or improve and/or treat or prevent frailty results in a lack of increase of a subject's FRAIL Scale score.

In some embodiments the methods as provided herein improve (or reduce) frailty index, or delay or slow a decline in frailty using at least one accepted measure of fragility. In some embodiments the methods as provided herein improve (or reduce) frailty index, or delay or slow a decline in frailty using at least one accepted measure of fragility selected from the Frailty Index (FI), the Physiological Frailty Index (PFI), Fried frailty score, Rockwood frailty index, FRAIL Scale and the modified frailty index.

In some embodiments, the frailty comprises low lean mass, weakness, exhaustion, low energy expenditure and/or slow walking speed. In embodiments, the present methods reduce or prevent the onset or development of one or more of low lean mass, weakness, exhaustion, low energy expenditure and/or slow walking speed.

Without wishing to be bound by theory, it is believed that AP-based agent including AP-based agents (e.g., IAPs) play a key role in many gastrointestinal and systemic processes including, for example, participating in intestinal defense, mediating anti-inflammatory functions, maintaining normal gut microflora profiles, maintaining mucosal barrier integrity, and regulating digestion and nutrient (fat) absorption. Accordingly, the present invention provides the use of AP-based agents in a broad-range of therapeutic applications for modulating immune functions, metabolic functions, and neurological functions. In various embodiments, the present invention provides for the treatment of microbiome-related disorders, GI dysbiosis, GI inflammation, colitis (e.g., ulcerative colitis), metabolic diseases (e.g., metabolic syndrome, obesity, and diabetes), neurological diseases (e.g., multiple sclerosis and spinal cord injury), cystic fibrosis, sepsis, and renal failure.

In various aspects, the present invention provides methods for modulating and protecting a subject's gastrointestinal microbiome, comprising administering an effective amount of a pharmaceutical composition comprising an AP-based agent (and/or additional therapeutic agents) to the subject. In some embodiments, methods of the invention may be used to treat subjects with reduced levels and/or function of gastrointestinal tract flora by administering an AP-based agent of the invention so as to increase or preserve the number of commensal bacteria and composition of the gastrointestinal microbiome. In other embodiments, methods of the invention relate to treating infections by pathogenic bacteria and/or inhibiting the growth or decrease the number of pathogenic bacteria in the gastrointestinal tract.

In various embodiments, the methods of the invention comprise treating or preventing a microbiome-mediated disorder. Illustrative microbiome-mediated disorder includes, but are not limited to, for example, those found in Table 3 of WO 2014/121298, the entire contents of which are incorporated herein by reference. For example, the methods described can be used to treat symptoms associated with reduced levels of commensal bacteria and/or function of gastrointestinal tract flora, e.g., antibiotic-associated diarrhea (AAD), *Clostridioides difficile*-associated disease (CDAD), inflammatory disorders, acquired immunodeficiency syndrome (AIDS) including HIV-mediated gut dysbiosis and GI barrier dysfunctions, hypothyroidism, and obesity.

In various aspects, the present invention provides pharmaceutical compositions comprising an AP-based agent of the invention (and/or additional therapeutic agents) for use in treating an antibiotic-induced adverse effect in the GI tract and/or prevention or treatment of *C. difficile* infection (CDI) and/or a *C. difficile*-associated disease in a subject in need thereof. Without wishing to be bound by theory, it is believed that AP-based agent of the invention mediate nucleoside triphosphate dephosphorylation which promote the growth of commensal bacteria in preference to pathologic bacteria and hasten the recovery from antibiotic-induced dysbiosis. Accordingly, treatment with the AP-based agents of the invention has the potential to protect from *Clostridioides difficile* infection and enteric gram negative pathogens. In various embodiments, the antibiotic-induced adverse effect and/or CDI or *C. difficile*-associated disease is one or more of: antibiotic-associated diarrhea, *C. difficile* diarrhea (CDD), *C. difficile* intestinal inflammatory disease, colitis, pseudomembranous colitis, fever, abdominal pain, dehydration and disturbances in electrolytes, megacolon, peritonitis, and perforation and/or rupture of the colon.

In various embodiments, the subjects include, but are not limited to, subjects that are at a particular risk for a microbiome-mediated disorder, such as, by way of non-limiting example, those undergoing treatment or having recently undergone treatment with an antibiotic. For example, the subject may have taken an antibiotic during the past about 30 or so days and/or have an immune system that is weak (e.g. from a chronic illness) and/or is a women and/or is elderly (e.g. over about 65 years old) and/or is undergoing (or has undergone) treatment with for heartburn or stomach acid disorders (e.g. with agents such as PREVACID, TAGAMET, PRILOSEC, or NEXIUM and related drugs) and/or has recently been in the hospital, including in an intensive care unit, or lives in a nursing home. Accordingly, in some embodiments, the methods and uses of the present invention treat or prevent a nosocomial infection and/or a secondary emergent infection and/or a hospital acquired infection (HAI).

In various embodiments, the present invention provides methods for treating antibiotic-induced adverse effects in the GI tract, comprising an effective amount of an AP-based agent of the invention (and/or additional therapeutic agents) to a subject in need thereof. In another embodiment, the present invention provides methods for preventing an anti-biotic-induced adverse effect in the GI tract, comprising an effective amount of an AP-based agent of the invention (and/or additional therapeutic agents) to a subject in need thereof.

In various embodiments, the AP-based agent of the invention protects the intestinal microbiome from antibiotics-induced damage. In an embodiment, the AP-based agent protects the intestinal microbiome from cephalosporin-induced damage. In some embodiment, the AP-based agent of the invention protects the intestinal microbiome from cef-triaxone (CRO)-induced damage. In some embodiments, the methods of the invention treat or prevent an antibiotics-associated adverse effect including but not limited to diar-rhea, nausea, vomiting, dysgeusia, colitis, and pseudomem-branous colitis disease and/or symptoms. In an embodiment, methods of the invention can be used to treat or prevent antibiotic-associated diarrhea (AAD).

In various embodiments, the present invention provides for compositions and methods for treating infections by pathogenic bacteria and/or inhibiting the growth or decrease the number of pathogenic bacteria in the gastrointestinal tract. In various embodiments, the present invention pro-vides for compositions and methods that mitigate or prevent the overgrowth of various coliforms in a patient's gut (including coliforms that are virulent and/or antibiotic resis-tant). Illustrative coliforms include *Citrobacter, Entero-bacter, Hafnia, Klebsiella*, and *Escherichia*. In various aspects, the methods and compositions described herein prevent or diminish secondary infections with resistant organisms. In an embodiment, the pathogenic bacteria is an enterobacteria such as *Salmonella.*

In some embodiments, the present invention prevents the expansion of the gut resistome. The gut resistome refers to the reservoir of antibiotic resistance genes that may be harbored by the human gut microbiota. Such antibiotic resistance genes confer antibiotic resistance among bacterial pathogens which constitute a major threat to public health. Bacteria can acquire antibiotic resistance genes by the mobilization and transfer of resistance genes from a donor strain. In various embodiments, the prevent methods reduces the number of antibiotic resistant bacteria in the gastroin-testinal tract thereby reducing the expansion of the gut resistome. In various embodiments, the present invention mitigates or prevents the growth of antibiotic resistant bacteria thus preventing or diminishing the expansion of the gut resistome.

In various embodiments, the present invention provides methods for treating or preventing *C. difficile* infection (CDI) and/or a *C. difficile*-associated disease, comprising administering an effective amount of an AP-based agent of the invention a subject in need thereof. In an embodiment, the present invention provides methods for preventing *C.*

*difficile* infection (CDI) and/or a *C. difficile*-associated dis-ease, comprising administering an effective amount of administering an effective amount of an AP-based agent of the invention to a subject in need thereof (by way of non-limiting example, a patient that is being administered or will be administered an antibiotic).

In some embodiments, the invention relates to a method of preventing *C. difficile* infection (CDI) and/or a *C. dif-ficile*-associated disease, comprising administering an effec-tive amount of administering an effective amount of AP-based agent of the invention to a subject in need thereof, wherein the subject is undergoing therapy with a primary antibiotic. A "primary antibiotic" refers to an antibiotic that is administered to a patient and which may result in CDI and/or *C. difficile*-associated disease. These include the antibiotics that most often lead to CDI and/or *C. difficile*-associated disease: e.g., fluoroquinolones, cephalosporins, clindamycin and penicillins.

In various embodiments, the CDI and/or *C. difficile*-associated disease is treated or prevented in the context of initial onset or relapse/recurrence (e.g. due to continued or restarted antibiotic therapy). For example, in a patient that has previously suffered from CDI, the present AP-based agent may be administered upon the first symptoms of recurrence. By way of non-limiting example, symptoms of recurrence include, in a mild case, about 5 to about 10 watery bowel movements per day, no significant fever, and only mild abdominal cramps while blood tests may show a mild rise in the white blood cell count up to about 15,000 (normal levels are up to about 10,000), and, in a severe case, more than about 10 watery stools per day, nausea, vomiting, high fever (e.g. about 102-104° F.), rectal bleeding, severe abdominal pain (e.g. with tenderness), abdominal distention, and a high white blood count (e.g. of about 15,000 to about 40,000).

Regardless of initial onset or relapse/recurrence, CDI and/or *C. difficile*-associated disease may be diagnosed via any of the symptoms described herein (e.g. watery diarrhea about 3 or more times a day for about 2 days or more, mild to bad cramping and pain in the belly, fever, blood or pus in the stool, nausea, dehydration, loss of appetite, loss of weight, etc.). Regardless of initial onset or relapse/recur-rence, CDI and/or *C. difficile*-associated disease may also be diagnosed via enzyme immunoassays, e.g., to detect the *C. difficile* toxin A or B antigen and/or glutamine dehydroge-nase (GDH), which is produced by *C. difficile* organisms), polymerase chain reactions (e.g., to detect the *C. difficile* toxin A or B gene or a portion thereof (e.g. tcdA or tcdB), including the ILLUMIGENE LAMP assay), a cell cytotox-icity assay. For example, any of the following tests may be used: Meridian ImmunoCard Toxins A/B; Wampole Toxin A/B Quik Chek; Wampole C. diff Quik Chek Complete; Remel Xpect *Clostridioides difficile* (formerly known as *Clostridium difficile*) Toxin A/B; Meridian Premier Toxins A/B; Wampole *C. difficile* Tox A/B II; Remel Prospect Toxin A/B EIA; Biomerieux Vidas *C. difficile* Toxin A&B; BD Geneohm *C. difficile*; Prodesse Progastro CD; and Cepheld Xpert *C. difficile*. In various embodiments, the clinical sample is a patient stool sample. Also a flexible sigmoidos-copy "scope" test and/or an abdominal X-ray and/or a computerized tomography (CT) scan, which provides images of your colon, may be used in assessing a patient (e.g. looking for characteristic creamy white or yellow plaques adherent to the wall of the colon). Further, biopsies (e.g. of any region of the GI tract) may be used to assess a potential CDI and/or *C. difficile*-associated disease patient.

In some embodiments, the methods and uses of the present invention include those in which an initial and/or adjunctive therapy is administered to a subject. Initial and/or adjunctive therapy indicates therapy that is used to treat, for example, a microbiome-mediated disorder or disease upon detection of such disorder or disease. In an embodiment, initial and/or adjunctive therapy indicates therapy that is used to treat CDI and/or *C. difficile*-associated disease upon detection of such disease. In some embodiments, the initial and/or adjunctive therapy is one or more of metronidazole, vancomycin, fidaxomicin, rifaximin, charcoal-based binder/adsorbent, fecal bacteriotherapy, probiotic therapy, and antibody therapy. In various embodiments, the methods and uses of the present invention include use of the alkaline phosphatase as an adjuvant to any of these initial and/or adjunctive therapies (including co-administration or sequential administration). In various embodiments, the methods and uses of the present invention include administration of the AP-based agent described herein to a subject undergoing initial and/or adjunctive therapies.

In various embodiments, the AP-based agent of the invention is administered to a subject who suffers from an increased mucosal permeability of the gastrointestinal tract. In some embodiments, increased mucosal permeability of the gastrointestinal tract is the result of a decreased perfusion or ischemia of the intestines. Ischemia, or a lack of oxygen supply by the bloodstream, may be caused by, for example, heart failure, congenital heart disease, congestive heart failure, coronary heart disease, ischemic heart disease, injuries, trauma or surgery.

In some embodiments, the increased mucosal permeability of the gastrointestinal tract is associated with or caused by autoimmune and inflammatory bowel diseases (IBD), for example, Celiac disease, Crohn's disease, and colitis (e.g., ulcerative colitis). Accordingly, in some embodiments, the present invention provides methods for treating or preventing autoimmune and inflammatory bowel diseases (IBD), for example, Celiac's disease, Crohn's disease, and colitis (e.g., ulcerative colitis), comprising administering an effective amount of an AP-based agent of the invention to a subject in need thereof. Inflammatory bowel disease (IBD) is a group of inflammatory conditions of the large intestine and, in some cases, the small intestine. The main forms of IBD are Crohn's disease and ulcerative colitis (UC). IBD also includes collagenous colitis, lymphocytic colitis, ischemic colitis, diversion colitis, Behçet's syndrome, infective colitis, and indeterminate colitis.

In some embodiments, the present invention provides methods of treating Celiac disease. In some embodiments, the present invention provides methods of treating gastrointestinal disorders associated with Celiac disease. Celiac disease is an autoimmune disorder that can occur in genetically predisposed people where the ingestion of gluten leads to damage in the small intestine. Individuals with celiac disease have increased intestinal permeability, which allows gluten break-down products (the triggering antigens of Celiac disease) to reach gut-associated lymphoid tissue, thus initiating an inflammatory response including inflammatory cytokine release and T-cell recruitment. Celiac disease is characterized by chronic inflammation of the small intestinal mucosa that may result in atrophy of the small intestinal villi and diverse symptoms, such as malabsorption, diarrhea, abdominal pain, bloating, fatigue, and nausea. In various embodiments, methods of the invention effectively treat one or more symptoms of Celiac disease including GI symptoms, abdominal symptoms, and non-GI symptoms.

Methods for measuring the improvement in one or more symptoms of Celiac disease can include assessment of the lactulose-to-mannitol (LAMA) ratio, which is an experimental biomarker of intestinal permeability (Kelly et al., (2012) Aliment Pharmacol Ther 2013; 37: 252-262, the entire disclosure is hereby incorporated by reference); measurement of anti-transglutaminase antibody levels; and assessment of clinical symptoms using the Celiac Disease Patient Reported Outcome (CeD PRO), Gastrointestinal Symptom Rating Scale (GSRS), Celiac Disease Gastrointestinal Symptom Rating Scale (CeD GSRS), Bristol Stool Form Scale (BSFS), General Well-Being Questionnaire, Short Form 12 Health Survey Version 2 (SF12V2), Celiac Disease Quality of Life Questionnaire (CeD-QoL), and Clinician Global Assessment of Disease Activity (CGA) as disclosed, for example, in WO/2015/154010, the entire disclosure of which is hereby incorporated by reference. In various embodiments, the present methods of treating Celiac disease provide for a therapeutic effect as assessed by one or more of these measurements.

In some embodiments, the present methods treat Celiac disease and allow a subject to introduce gluten into its diet without substantial symptoms.

In various embodiments, the increased mucosal permeability of the gastrointestinal tract is associated with or caused by cachexia such as cachexia associated with one or more of cancer, AIDS, heart failure, and/or chronic obstructive pulmonary disease (COPD). In some embodiments, the present invention treats or prevents the increased intestinal permeability and/or gut dysbiosis associated with cachexia.

In some embodiments, the present methods treat or prevent cachexia or wasting syndrome. In some embodiments, the present methods reduce, eliminate, or prevent one or more of loss of weight, muscle atrophy, fatigue, weakness, and loss of appetite. In some embodiments, the present methods reduce, eliminate, or prevent one or more of decrease of body mass and less fatty tissue accumulation that cannot be reversed nutritionally. In some embodiments, the present methods treat or prevent sarcopenia.

In some embodiments, the cachexia treated by the present invention is found in a patient afflicted with one or more of cancer, HIV or AIDS, celiac disease, chronic obstructive pulmonary disease, multiple sclerosis, Rheumatoid arthritis, congestive heart failure, tuberculosis, familial amyloid polyneuropathy, mercury poisoning (acrodynia) and hormonal deficiency.

In various embodiments, the present treatment or prevention of cachexia with the present AP-based agent find use in combination with, or in a patient undergoing treatment with one or more of β-hydroxy β-methylbutyrate (HMB), various progestins (e.g. megestrol acetate), anabolic-androgenic steroids (e.g. oxandrolone), thalidomide and cytokine antagonists, cannabinoids, omega-3 fatty acids (e.g. eicosapentaenoic acid (EPA)), non-steroidal anti-inflammatory drugs, prokinetics, ghrelin and ghrelin receptor agonist, anabolic catabolic transforming agents such as MT-102, selective androgen receptor modulators, cyproheptadine, and hydrazine.

In some embodiments, the increased mucosal permeability of the gastrointestinal tract is associated with or caused by Acquired Immunodeficiency Syndrome (AIDS). Accordingly, in some embodiments, the present invention provides methods of treating gastrointestinal disorders associated with Acquired Immunodeficiency Syndrome (AIDS). Gastrointestinal disorders are among the most frequent complaints in patients with human immunodeficiency virus 1 (HIV-1) or human immunodeficiency virus 2 (HIV-2)-associated AIDS. Gastrointestinal manifestations of HIV disease include diarrhea, dysphagia, odynophagia, nausea, vomiting, weight loss, abdominal pain, anorectal disease, jaundice, hepatomegaly, gastrointestinal tract bleeding, and gastrointestinal tumors (e.g., Kaposi's sarcoma and non-Hodgkin's lymphoma).

Progressive HIV infection often results in GI tract damage, microbial translocation, inflammation, and immune activation which drive progression of disease to AIDS. The term "HIV enteropathy" has been used to describe changes in mucosal structure and function associated with gut-mediated immune dysfunction, as well as to denote the clinical syndrome of chronic diarrhea without an identified infectious cause. In addition to chronic diarrhea, HIV enteropathy is often characterized by increased GI inflammation, increased intestinal permeability, and malabsorption of bile acids and vitamin B12—abnormalities that are thought to be due to direct or indirect effects of HIV on the enteric mucosa (Brenchley J M, Douek D C. Mucosal Immunol 2008; 1:23-30). Clinical consequences include decreased fat and carbohydrate absorption, a trend toward decreased small-bowel transit time, and jejunal atrophy. In various embodiments, methods of the invention effectively treat the symptomatic effects of HIV enteropathy. In various embodiments, methods of the invention prevent, slow, or reverse the progression of HIV infection to AIDS. In various embodiments, methods of the invention prevent or slow the progression of AIDS to death.

Further still, the HIV-1 subtype that a subject becomes infected with may be a factor in the rate of progression to AIDS. In various embodiments, the present methods effectively treat a patient infected with HIV-1 subtype C, D, and G. In another embodiment, the present methods effectively treat a patient infected with HIV-1 subtype A.

In some embodiments, the present invention provides methods of treating various GI disorders associated with HIV infection and/or AIDS. For example, the present invention provides methods of treating HIV-mediated gut dysbiosis and GI barrier dysfunctions, which in various embodiments, may be caused by the HIV, the antibiotics administered to the HIV infected subject, and/or the medications being administered to the HIV infected subject. For example, the HIV infected subject may be taking one or more nucleoside analogues such as deoxyadenosine analogues (e.g., didanosine, vidarabine), adenosine analogues (e.g., BCX4430), deoxycytidine analogues (e.g., cytarabine, emtricitabine, lamivudine, zalcitabine), guanosine and deoxyguanosine analogues (e.g., abacavir, aciclovir, entecavir), thymidine and deoxythymidine analogues (e.g., stavudine, telbivudine, zidovudine), and deoxyuridine analogues (e.g., idoxuridine, trifluridine). In some embodiments, the HIV infected subject may be taking one or more drugs of the highly active anti-retroviral therapy (HAART) regimen. Exemplary HAART medications include entry inhibitors or fusion inhibitors (e.g., maraviroc, enfuvirtide), nucleoside reverse transcriptase inhibitors (NRTI) and nucleotide reverse transcriptase inhibitors (NtRTI) such as the nucleoside and nucleotide analogues described herein, non-nucleoside reverse transcriptase inhibitors (e.g., nevirapine, efavirenz, etravirine, rilpivirine), integrase inhibitors (e.g., raltegravir), and protease inhibitors (e.g., lopinavir, indinavir, nelfinavir, amprenavir, ritonavir, darunavir, atazanavir).

In various embodiments, the present methods reduce local inflammation, alter composition of the GI microbiota, enhance clearance of products of microbial translocation from the circulation, and repair enterocyte barrier in an HIV infected subject and/or a subject having AIDS. In an embodiment, the present methods reduce GI tract damage and gut dysbiosis in an HIV infected subject and/or a subject having AIDS. For example, the present methods may reverse the changes in GI microbiota observed in HIV infected subjects or subjects having AIDS. By way of example, these changes in GI microbiota that may be reversed by the present methods include an altered microbiota featuring increased pathobionts such as *Staphylococcus* spp., *Pseudomonas* spp., Enterobacteriaceae family members with pro-inflammatory potential, as well as enteropathogenic bacteria that catabolize tryptophan into kynurenine derivatives (including *Pseudomonas, Xanthomonas, Bacillus*, and *Burkholderia* spp.) In an embodiment, the present methods reduce GI barrier dysfunctions in an HIV infected subject and/or a subject having AIDS. For example, the present methods may reverse the increased intestinal permeability (e.g., leaky gut syndrome) in an HIV infected subject and/or a subject having AIDS. In an embodiment, the present methods reduce microbial translocations or translocations of microbial products and inflammatory mediators (e.g., LPS) into the systemic circulation in an HIV infected subject and/or a subject having AIDS. In such methods, the levels of LPS, EndoCAb, sCD14, and I-FABP in the subject's plasma may be reduced. In an embodiment, the present methods reduce immune activation and inflammation (e.g., local and systemic immune activation and inflammation) in an HIV infected subject and/or a subject having AIDS. For example, the present methods may decrease inflammation in the gut-associated lymphoid tissue (GALT) and increase the number of CD4+ cells and Th17 cells. The present methods may further inhibit the release of cytotoxic T cells as well as the production of inflammatory mucosal cytokines and markers such as interferon-$\alpha$, tumor necrosis factor-$\alpha$, CRP, IL-1$\beta$, IL-2, IL4, IL-6 and IL-13.

In some embodiments, the present invention provides methods for treating or preventing dysbiosis and gastrointestinal dysfunction in patients with cystic fibrosis (CF). The genetic disease cystic fibrosis (CF) is associated with mutations in the CF transmembrane conductance regulator (CFTR), which regulates epithelial cell ion and water permeability. In some embodiments, the present methods are used to treating a subject who is homozygous for one or more mutations in the CFTR gene. In some embodiments, the subject is heterozygous for one or more mutations in the CFTR gene. In some embodiments, the one or more CFTR mutations are nonsense mutations. In some embodiments, the one or more CFTR mutations are gating mutations. In some embodiments, the one or more CFTR mutations are protein processing mutations. In some embodiments, the one or more CFTR mutations are conductance mutations. In some embodiments, the one or more CFTR mutations are translation mutations. Examples of CFTR mutations include, but are not limited to, F508del, G542X, G85E, R334W, Y122X, G551D, R117H, A455E, S549R, R553X, V520F, R1162X, R347H, N1203K, S549N, R347P, R560T, G1244E, G1349D, G178R, G551S, S1251N, S1255P, S549R, S1255X, Add9T, Y1092X, M1191K, W 1282X, 3659delC, 394delTT, 3905insT, 1078delT, delta 1507, 3876delA, 2184delA, 2307insA, 711+1G>T, 1717-1G>A, 2789+5G>A, 1898+5G>T, 3120+1G>A, 621+1G>T, 3849+I0kbC>T, 1898+1G>A, 2183 AA>G, and/or 5/7/9T. In various embodiments, methods of the invention are used to treat a CF patient having one or more of the CFTR mutations disclosure herein. In an embodiment, the patient has one or more of the following CFTR mutations: G551D, G1244E, G1349D, G178R, G551S, S1251N, S1255P, S549N, S549R and/or R117H. In an embodiment, the patient has a F508del mutation. Methods for screening a patient's genotype for CFTR mutations are known and may be carried out by, for example, DNA sequencing such as bidirectional sequencing.

CF patients often exhibit symptoms including chronic respiratory infections and dysfunction at gastrointestinal (GI) mucosal surfaces, resulting insubstantial morbidity and mortality. One of the earliest manifestations of CF is GI dysfunction including severe and recurrent intestinal obstruction as well as nutrient malabsorption, which result in growth failure. CF patients also exhibit GI dysbiosis such as an overabundance of *E. coli* in the fecal microbiota and a decrease in the relative abundance of *Bifidobacterium* species. In various embodiments, methods of the invention effectively treat one or more GI-related symptoms of in CF patients.

Methods for measuring change and/or improvement in GI tract function can include, but are not limited to: endoscopy for direct examination of epithelium and mucosa; histological evaluation and/or tissue procurement for direct evaluation of structural changes and/or immune biomarkers; urine tests for assessment of permeability with non-absorbable sugars and LPS levels; stool tests for assessment of inflammation and/or microbiota changes (for example by PCR); and/or blood tests for assessment of specific markers, including CD4+ cell counts, Th17 cell counts, and/or LPS levels.

In some embodiments, the present invention provides methods of treating gastrointestinal disorders associated with hypothyroidism. Hypothyroidism is a condition in which the thyroid gland does not produce enough thyroid hormone (thyroxine or T4). Often, hypothyroidism slows the actions of the digestive tract causing constipation, or the digestive tract may stop moving entirely. Methods of the invention may alleviate the one or more gastrointestinal symptoms associated with hypothyroidism.

In some embodiments, the present invention provides methods for preventing or treating necrotizing enterocolitis (NEC).

In various embodiments, methods of the invention relate to a pediatric subject for the prevention or treatment of NEC. In various embodiments, the pediatric subject may be from about 1 day to about 1 week old, from about 1 week to about 1 month old, from about 1 month to about 12 months old, from about 12 months to about 18 months old, from about 18 to about 36 months old, from about 1 to about 5 years old, from about 5 to about 10 years old, from about 10 to about 15 years old, or from about 15 to about 18 years old. In some embodiments, the pediatric subject is an infant of about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, or about 12 months of age. In various embodiments, the pediatric subject is feeding on formula and/or milk. In various embodiments, the pediatric subject is undergoing treatment or has recently undergone treatment with an antibiotic.

In various embodiments, the pediatric subject is a premature infant. In some embodiments, the premature infant is born at less than 37 weeks of gestational age. In some embodiments, the premature infant is born at about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, or about 37 weeks of gestational age. In other embodiments, the pediatric subject is a full term infant, for example, an infant who is born later than about 37 weeks of gestational age. In some embodiments, the pediatric subject may exhibit one or more of prenatal asphyxia, shock, sepsis, or congenital heart disease. In various embodiments, the pediatric subject is of low birth weight. In various embodiments, the pediatric subject weighs less than about 5 pounds, about 4 pounds, about 3 pounds, or about 2 pounds.

In various embodiments, methods of the invention relate to a pregnant woman for the prevention or treatment of NEC. In some embodiments, the pregnant woman is undergoing treatment or has recently undergone treatment with an antibiotic.

The presence and severity of NEC is graded using the staging system of Bell et al., J. Ped. Surg., 15:569 (1980) as follows: In various embodiments, the present methods treat disease at any of these stages.

Stage I Systemic manifestations—temperature instability, lethargy, apnea, bradycardia (Suspected NEC) Gastrointestinal manifestations—poor feeding, increased pregavage residuals, emesis (may be bilious or test positive for occult blood), mild abdominal distention, occult blood in stool (no fissure)

Non-specific or normal radiological signs

Stage II Above signs and symptoms plus persistent occult or gross gastrointestinal bleeding, marked abdominal distention (Definite NEC) Abdominal radiographs showing significant intestinal distention with ileus, small-bowel separation (edema in bowel wall or peritoneal fluid), unchanging or persistent "rigid" bowel loops, pneumatosis intestinalis, portal venous gas (NEC) Laboratory changes (thrombocytopenia, metabolic acidosis)

Stage III Above signs and symptoms plus deterioration of vital signs, evidence of septic shock, or marked gastrointestinal hemorrhage, hypotension, striking abdominal distension, peritonitis (Advanced NEC) Abdominal radiographs showing pneumoperitoneum in addition to findings listed for Stage II Additional laboratory changes (metabolic and respiratory acidosis, disseminated intravascular coagulation)

In various embodiments, methods of the invention effectively treat one or more symptoms of NEC including any of the symptoms described above as well as those symptoms known in the art, including GI symptoms, abdominal symptoms, and non-GI symptoms. In various embodiments, methods of the invention effectively prevent the development of NEC in a subject such as a pediatric subject. In various embodiments, methods of the invention effectively prevent progression of NEC in a subject such as a pediatric subject, for example, from stage I to stage II or from stage I to stage III. In various embodiments, methods of the invention effectively result in regression of NEC in a subject such as a pediatric subject, for example, from stage Ill to stage II or stage I to complete cure, or from stage to stage I or to complete cure.

Intestinal dysbiosis is associated with the development of NEC and can be detected in a subject prior to any clinical evidence of the disease. In various embodiments, methods of the invention effectively restore normal microbiota in the intestinal tract of the treated subject. In some embodiments, methods of the invention maintain a normal microbiota in the intestinal tract. For instance, in some embodiments, the methods of the invention maintain a healthy balance (e.g. a healthy ratio and/or healthy distribution) of intestinal microbiota of a subject. In another embodiment, the methods of the invention treat or prevent the overgrowth of one or more pathogenic microorganisms in the GI tract. In certain embodiments, methods of the invention effectively reduce the levels of *Clostridium butyricum* and/or *Clostridium perfringens* in the intestinal tract.

Methods for measuring the improvement in one or more symptoms of NEC include diagnostic imaging modalities such as X-ray and ultrasonography. Methods for measuring change and/or improvement in GI tract function can include, but are not limited to: endoscopy or colonoscopy for direct examination of epithelium and mucosa; histological evaluation and/or tissue procurement for direct evaluation of structural changes and/or immune biomarkers; stool tests for assessment of inflammation and/or microbiota changes (for example by PCR); and/or blood tests for assessment of specific markers and cells.

In some embodiments, the present invention provides methods of treating or preventing metabolic syndrome, diabetes, hypertension, cardiovascular disease, nonalcoholic fatty liver and other metabolic diseases. In various embodiments, the metabolic syndrome is associated with elevated triglycerides, elevated low density lipoproteins, reduced high density lipoproteins, reduced lipoprotein index, elevated fasting glucose levels, elevated fasting insulin, reduced glucose clearance following feeding, insulin resistance, impaired glucose tolerance, obesity and combinations thereof. For example, the present methods may be used to treating subjects having metabolic syndrome and having abdominal obesity (e.g., waist circumference of 40 inches or above in men or 35 inches or above in women), a blood triglyceride level of 150 mg/dL or greater, HDL of less than 40 mg/dL in men or less than 50 mg/dL in women, systolic blood pressure of 130 mm Hg or greater or diastolic blood pressure of 85 mm Hg or greater and/or fasting glucose of 100 mg/dL or greater. Additional metabolic diseases that may be treated using methods of the invention include those described in US2013/0251701, US2011/0206654, and US2004/0115185, the entire contents of which are hereby incorporated by reference.

In an embodiment, the metabolic disease is obesity. Early exposure to antibiotics (e.g. within about the first 2 years of life) can disrupt the microbiome and lead to eventual disease. Bailey, et al. JAMA Pediatr. 168(11), November 2014, the entire contents of which are hereby incorporated by reference, describes how early exposure to antibiotics is linked to obesity. Accordingly, in some embodiments, the present methods protect the microbiome of a child and prevent diseases such as obesity. In addition, a shift in the ratio between bacterial divisions Firmicutes and Bacteroidetes is often observed in obese individuals. Accordingly, in some embodiments, the present invention provides methods for treating or preventing obesity by administering an AP agent of the invention. Methods of the invention retain a normal diversity of bacteria in the intestinal tract, such as for example, Bacteroidetes, Proteobacteria, and Firmicutes, thereby treating or preventing obesity. Further still, AP-based agent may influence fat absorption at the gastrointestinal tract. Accordingly, in various embodiments, the present invention provides methods for treating or preventing obesity by limiting GI fat absorption. In various embodiments, methods of the invention are effective for inducing weight loss or preventing weight gain. In some embodiments, the subjects may have undertaken or will undertake a surgery of the digestive system; be greater than about 80-100 pounds overweight; have a BMI of greater than about 35 kg/m²; or have a health problem related to obesity. In some embodiments, the subjects may have dyslipidemia including hyperlipidemia and hyperlipoproteinemia.

In another embodiment, the metabolic disease is diabetes. In various embodiments, the present invention relates to the treatment for diabetes (type 1 or type 2) and/or glucose intolerance. In various embodiments, the present invention relates to the prevention of diabetes (type 1 or type 2) and/or glucose intolerance. In various embodiments, the present invention relates to the reduction of complications from diabetes (type 1 or type 2) and/or glucose intolerance. In some embodiments, the present invention relates to a method for treating subjects at risk of diabetes, one or more of insulin resistance, prediabetes, impaired fasting glucose (IFG), and impaired glucose tolerance (IGT).

In various embodiments, the present invention relates to the treatment of type 1 diabetes with an AP-based agent. Type 1 diabetes, once known as juvenile diabetes or insulin-dependent diabetes, is a chronic condition in which the pancreas produces little or no insulin. Treatment is often via intensive insulin regimens, which attempt to mimic the body's normal pattern of insulin secretion, and often involve basal and bolus insulin coverage. For example, one common regimen is the administration of a long-acting insulin (including, for example, glargine/detemir) once or twice a day with rapid acting insulin (including, for example, aspart, glulisine, lispro) preprandially or postprandially and as needed to correct high blood sugars (as monitored by a glucose meter, for example). Doses administered preprandially or postprandially or as needed to correct high blood sugars may be referred to as bolus administrations. Another common regimen involves dosing, including continuous dosing, via an insulin pump (or continuous subcutaneous insulin infusion device (CSII)) of, for example a rapid acting insulin (as described herein and including, for example, aspart, glulisine, lispro). In various embodiments, an AP-based agent, may replace any of the insulins used in various regimens, including instances in which the insulins are not providing effective therapy in the patient, an AP-based agent may cause an increase in patient compliance as it may allow for easier self-dosing relative to various forms of insulin, which must be administered as various doses throughout the day—even in the context of an insulin pump, which requires programming. Further, an AP-based agent can offset common frustration of diabetic patient dosing, such as, for example, the dawn phenomenon. Alternatively, an AP-based agent may be used adjuvant to any of the type 1 diabetes treatments described herein to, for example, normalize a patient's regimen and avoid blood sugar "dips" (e.g. hypoglycemia, e.g. blood sugar of below about 70 mg/dL) and "spikes" (e.g. hyperglycemia, e.g. blood sugar of greater than about 200 mg/dL) that afflict many patients. Accordingly, in some embodiments, an AP-based agent may treat or prevent symptoms associated with hypoglycemia, including for example, shakiness, anxiety, nervousness, palpitations, tachycardia, pallor, coldness, clamminess, dilated pupils (mydriasis), hunger, borborygmus, nausea, vomiting, abdominal discomfort, headache, abnormal mentation, impaired judgment, nonspecific dysphoria, paresthesia, negativism, irritability, belligerence, combativeness, rage, personality change, emotional lability, fatigue, weakness, apathy, lethargy, daydreaming, sleep, confusion, amnesia, lightheadedness or dizziness, delirium, staring, "glassy" look, blurred vision, double vision, flashes of light in the field of vision, automatism, difficulty speaking, slurred speech, ataxia, incoordination, focal or general motor deficit, paralysis, hemiparesis, paresthesia, headache, stupor, coma, abnormal breathing, generalized or focal seizures, memory loss, CNS damage (e.g. cognitive impairment), amnesia, and death. Accordingly, in some embodiments, an AP-based agent may treat or prevent symptoms associated with hyperglycemia, including for example, polyphagia, polydipsia, polyuria, blurred vision, fatigue, weight loss, poor wound healing, dry mouth, dry or itchy skin, tingling in feet or heels, erectile dysfunction, recurrent infections, external ear infections (e.g. swimmer's ear), cardiac arrhythmia, stupor, coma, and seizures. In various regimens, a type 1 diabetes patient may receive additional agents to supplement insulin therapy. In some embodiments, an AP-based agent, is used in this manner. AP-based agents, may provide additional therapeutic benefits in patients that are struggling to manage type 1 diabetes with insulin therapy alone. In some embodiments, patients that are struggling to manage type 1 diabetes with insulin therapy alone have poor glycemic control as described herein.

In some embodiments, an AP-based agent finds use in reducing a patient's blood glucose level to below about 10 mM, e.g. within the range of about 4 mM to about 7 mM.

In some aspects, the present invention provides a method for treating type 1 or type 2 diabetes, comprising administering an effective amount of an AP-based agent.

In a number of embodiments, including those in which an AP-based agent prevents diabetes and/or treats a pre-diabetic condition, a patient is at risk of diabetes if the patient is characterized by one or more of: being physically inactive; having a parent or sibling with diabetes; having a family background associated with high incidence of diabetes, selected from that is African American, Alaska Native, American Indian, Asian American, Hispanic/Latino, or Pacific Islander American; giving birth to a baby weighing more than 9 pounds; being diagnosed with gestational diabetes; having high blood pressure of about 140/90 mmHg or above; being treated for high blood pressure; having HDL cholesterol level below about 35 mg/dL and/or a triglyceride level above about 250 mg/dL; having polycystic ovary syndrome (PCOS); and having cardiovascular disease.

In various embodiments, an AP-based agent may be used to treat diabetes in the context of hospitalization. For example, in some embodiments, an AP-based agent may be administered to a patient that is in a diabetic coma. In some embodiments, the patient may be administered to a patient that has one or more of a severe diabetic hypoglycemia, advanced diabetic ketoacidosis (e.g. advanced enough to result in unconsciousness, contributing factors may include one or more of hyperglycemia, dehydration, shock, and exhaustion), hyperosmolar nonketotic coma (e.g. with one or more of hyperglycemia and dehydration are contributing factors). In these embodiments, an AP-based agent, may be used in conjunction with standard treatment regimens of diabetic comas, including administering one or more of glucose, glucagon, insulin, fluids (e.g. saline with potassium and/or other electrolytes), any of which, optionally, are administered intravenously. In some embodiments, an AP-based agent may replace insulin in these treatment regimens and, optionally, is administered orally.

In various embodiments, the AP-based agent may be used to treat pregnant women with increased risk of gestational diabetes. Some pregnant women develop gestational diabetes starting around 24-weeks of pregnancy, and if left untreated, gestational diabetes may cause premature birth and still birth. In some embodiments, the present invention provides methods of preventing and/or treating gestational diabetes in pregnant women. In various embodiments, methods of the invention may also be utilized to treat pregnant women who are at increased risk for inflammation such as GI inflammation. In some embodiments, the present methods reduce inflammation in pregnant women.

Further, in various embodiments pertaining to diabetes, the patient may be receiving or there may be co-administration with one or more additional agents. Illustrative additional agents include insulin or any anti-diabetic agents (e.g. biguanides, insulin secretogogues such as sulphonylureas or meglitinides, inhibitors of $\alpha$-glucosidase, thiazolidinediones, and others). The methods of treatment described herein, in various embodiments, may comprise administering an AP-based agent to a patient that is receiving one or more additional agents and/or non-insulin diabetes agents. Additional agents include one or more of a sulfonylurea (e.g. DYMELOR (acetohexamide), DIABINESE (chlorpropamide), ORINASE (tolbutamide), and TOLINASE (tolazamide), GLUCOTROL (glipizide), GLUCOTROL XL (extended release), DIABETA (glyburide), MICRONASE (glyburide), GLYNASE PRESTAB (glyburide), and AMARYL (glimepiride)); a Biguanide (e.g. metformin (GLUCOPHAGE, GLUCOPHAGE XR, RIOMET, FORTAMET, and GLUMETZA)); a thiazolidinedione (e.g. ACTOS (pioglitazone) and AVANDIA (rosiglitazone); an alpha-glucosidase inhibitor (e.g., PRECOSE (acarbose) and GLYSET (miglitol); a Meglitinide (e.g., PRANDIN (repaglinide) and STARLIX (nateglinide)); a Dipeptidyl peptidase IV (DPP-IV) inhibitor (e.g., JANUVIA (sitagliptin), NESINA (alogliptin), ONGLYZA (saxagliptin), and TRADJENTA (linagliptin)); Sodium-glucose cotransporter 2 (SGLT2) inhibitor (e.g. INVOKANA (canagliflozin)); and a combination pill (e.g. GLUCOVANCE, which combines glyburide (a sulfonylurea) and metformin, META-GLIP, which combines glipizide (a sulfonylurea) and metformin, and AVANDAMET, which uses both metformin and rosiglitazone (AVANDIA) in one pill, KAZANO (alogliptin and metformin), and OSENI (alogliptin plus pioglitazone).

Other additional agents include METFORMIN oral, ACTOS oral, BYETTA subcutaneous, JANUVIA oral, WELCHOL oral, JANUMET oral, glipizide oral, glimepiride oral, GLUCOPHAGE oral, LANTUS subcutaneous, glyburide oral, ONGLYZA oral, AMARYI oral, LANTUS SOLOSTAR subcutaneous, BYDUREON subcutaneous, LEVEMIR FLEXPEN subcutaneous, ACTOPLUS MET oral, GLUMETZA oral, TRADJENTA oral, bromocriptine oral, KOMBIGLYZE XR oral, INVOKANA oral, PRANDIN oral, LEVEMIR subcutaneous, PARLODEL oral, pioglitazone oral, NOVOLOG subcutaneous, NOVOLOG FLEXPEN subcutaneous, VICTOZA 2-PAK subcutaneous, HUMALOG subcutaneous, STARLIX oral, FORTAMET oral, GLUCOVANCE oral, GLUCOPHAGE XR oral, NOVOLOG Mix 70-30 FLEXPEN subcutaneous, GLYBURIDE-METFORMIN oral, acarbose oral, SYMLINPEN 60 subcutaneous, GLUCOTROI XL oral, NOVOLIN R inj, GLUCOTROL oral, DUETACT oral, sitagliptin oral, SYMLINPEN 120 subcutaneous, HUMALOG KWIKPEN subcutaneous, JANUMET XR oral, GLIPIZIDE-METFORMIN oral, CYCLOSET oral, HUMALOG MIX 75-25 subcutaneous, nateglinide oral, HUMALOG Mix 75-25 KWIKPEN subcutaneous, HUMULIN 70/30 subcutaneous, PRECOSE oral, APIDRA subcutaneous, Humulin R inj, Jentadueto oral, Victoza 3-Pak subcutaneous, Novolin 70/30 subcutaneous, NOVOLIN N subcutaneous, insulin detemir subcutaneous, glyburide micronized oral, GLYNASE oral, HUMULIN N subcutaneous, insulin glargine subcutaneous, RIOMET oral, pioglitazone-metformin oral, APIDRA SOLOSTAR subcutaneous, insulin lispro subcutaneous, GLYSET oral, HUMULIN 70/30 Pen subcutaneous, colesevelam oral, sitagliptin-metformin oral, DIABETA oral, insulin regular human inj, HUMULIN N Pen subcutaneous, exenatide subcutaneous, HUMALOG Mix 50-50 KWIKPEN subcutaneous, liraglutide subcutaneous, KAZANO oral, repaglinide oral, chlorpropamide oral, insulin aspart subcutaneous, NOVOLOG Mix 70-30 subcutaneous, HUMALOG Mix 50-50 subcutaneous, saxagliptin oral, ACTOPLUS Met XR oral, miglitol oral, NPH insulin human recomb subcutaneous, insulin NPH and regular human subcutaneous, tolazamide oral, mifepristone oral, insulin aspart protam-insulin aspart subcutaneous, repaglinide-metformin oral, saxagliptin-metformin oral, linagliptin-metformin oral, NESINA oral, OSENI oral, tolbutamide oral, insulin lispro protamine and lispro subcutaneous, pramlintide subcutaneous, insulin glulisine subcutaneous, pioglitazone-glimepiride oral, PRANDIMET oral, NOVOLOG PenFill subcutaneous, linagliptin oral, exenatide microspheres subcutaneous, KORLYM oral, alogliptin oral, alogliptin-pioglitazone oral, alogliptin-metformin oral, and canagliflozin oral.

Other additional agents include Lispro (HUMALOG); Aspart (NOVOLOG); Glulisine (APIDRA); Regular (NOVOLIN R or HUMULIN R); NPH (NOVOLIN N or HUMULIN N); Glargine (LANTUS); Detemir (LEVEMIR); HUMULIN or NOVOLIN 70/30; and NOVOLOG Mix 70/30 HUMALOG Mix 75/25 or 50/50.

In various embodiments, the present invention is used to treat or prevent various neurodegenerative diseases. In some embodiments, the neurodegenerative disease is selected from multiple sclerosis (MS; including, without limitation benign multiple sclerosis, relapsing-remitting multiple sclerosis (RRMS), secondary progressive multiple sclerosis (SPMS), progressive relapsing multiple sclerosis (PRMS), and primary progressive multiple sclerosis (PPMS)), Alzheimer's. disease (including, without limitation, Early-onset Alzheimer's, Late-onset Alzheimer's, and Familial Alzheimer's disease (FAD), Parkinson's disease and parkinsonism (including, without limitation, Idiopathic Parkinson's disease, Vascular parkinsonism, Drug-induced parkinsonism, Dementia with Lewy bodies, Inherited Parkinson's, Juvenile Parkinson's), Huntington's disease, and Amyotrophic lateral sclerosis (ALS, including, without limitation, Sporadic ALS, Familial ALS, Western Pacific ALS, Juvenile ALS, Hiramaya Disease).

In various embodiments, the present invention is used to treat spinal cord injury and/or the dysbiosis associated with spinal cord injury. Spinal cord injury has been shown to increase intestinal permeability and bacterial translocation from the gut. These changes are associated with immune cell activation in gut-associated lymphoid tissues (GALTs) and changes in the intestinal microbiome. The gut dysbiosis associated with spinal cord injury has been implicated with impairing locomotor recovery and exacerbating neural lesion pathology and intraspinal inflammation. In some embodiments, the present invention prevents and/or treats the bacterial translocation and gut dysbiosis associated with spinal cord injury. In some embodiments, the methods of the invention confer neuroprotection and/or improve locomotor recovery following spinal cord injury. In some embodiments, the methods of the invention induce anti-inflammatory immune phenotypes in the GALTs. In some embodiments, the methods of the invention reduce neurological lesions and intraspinal inflammations associated with spinal cord injuries.

In various embodiments, an AP-based agent may be used to treat traumatic brain injuries (TBI) and the symptoms thereof. In various embodiments, an AP-based agent may be used to treat various conditions associated with trauma to the brain or spinal cord e.g. caused by physical forces acting on the skull or spinal column, ischemia, stroke, arrested breathing, cardiac arrest, cerebral thrombosis or embolism, neurological problems caused by AIDS, cerebral hemorrhage, encephalomyelitis, hydrocephalus, post-operative events, cerebral infections, and concussions or elevated intracranial pressure.

In various embodiments, an AP-based agent may be used to treat 'an alteration in brain function, or other evidence of brain pathology, caused by an external force.

In various embodiments, an AP-based agent may be used to treat TBI as classified by various methods. For instance, clinical severity (e.g. Glasgow Coma Scale (GSC), see Teasdale & Jennett (1974) Lancet, 2, 81-84, a 15-point scale which looks at motor, vocal and eye-opening responses in a patient after resuscitation) may be used. In various embodiments, an AP-based agent may be used to treat mild, moderate or severe head injuries as defined by GSC. Further, TBI may be classified using a pathology-based classification of TBI, e.g. based on an assessment on an abnormality needing treatment from an anatomical and physiological perspective. The most common patho-physiological model used to describe TBI is an evaluation of whether injuries are either primary or secondary injuries. It is generally accepted that the primary injury is that which is due to the initial immediate injury and is unavoidable. Secondary injury refers to subsequent injuries which can be avoided, such as hypoxia, hypertension or hypercapnia. Further TBI may be assessed such as Computerized Tomography (CT) or Magnetic Resonance Imaging (MRI), as well as Electroencephalogram (EEG) and Intra-Cranial Pressure (ICP).

In various embodiments, an AP-based agent may be used to treat or prevent stroke. For instance, the stroke being treated may be ischemic or hemorrhagic. In various embodiments, the hemorrhagic stroke is a neurological deficit of cerebrovascular cause that persists beyond 24 hours or is interrupted by death within 24 hours. The hemorrhagic stroke may be a cerebral hemorrhage (intracerebral hemorrhage), due to either intraparenchymal hemorrhage or intraventricular hemorrhage. The hemorrhagic stroke may be a subarachnoid hemorrhage. In various embodiments, the stroke is ischemic, e.g. as classified by the Oxford Community Stroke Project classification (OCSP, i.e. classified as total anterior circulation infarct (TACI), partial anterior circulation infarct (PACI), lacunar infarct (LACI) or posterior circulation infarct (POCI)) or the TOAST (Trial of Org 10172 in Acute Stroke Treatment) classification (i.e. a stroke is classified as being due to (1) thrombosis or embolism due to atherosclerosis of a large artery, (2) an embolism originating in the heart, (3) complete blockage of a small blood vessel, (4) other determined cause, (5) undetermined cause (two possible causes, no cause identified, or incomplete investigation)).

In various embodiments, the present invention provides methods of treating or preventing sepsis. Sepsis is characterized by a whole-body inflammatory state caused by infection. Sepsis includes the presence of various pus-forming and other pathogenic organisms, or their toxins, in the blood or tissues. In some embodiments, the present invention provides methods of treating or preventing septicemia (blood poisoning), bacteremia, viremia, and/or fungemia. In various embodiments, the present invention treats the various end-organ pathologies associated with sepsis such as hypotension, acute tubular necrosis (ATN) and acute respiratory distress syndrome (ARDS).

In various embodiments, the present invention provides methods of treating or preventing renal failure such as acute renal failure (ARF). Acute renal failure involves an acute loss of kidney function that results in an increase of the serum creatinine level. In acute renal failure, the glomerular filtration rate decreases over days to weeks. As a result, excretion of nitrogenous waste is reduced, and fluid and electrolyte balances cannot be maintained. Patients with acute renal failure are often asymptomatic, and the condition is diagnosed by observed elevations of blood urea nitrogen (BUN) and serum creatinine levels. Complete renal shutdown is present when the serum creatinine level rises by at least 0.5 mg per dL per day and the urine output is less than 400 mL per day (oliguria). The AP-based agents described herein can be used not only in the treatment of renal failure but also to improve renal cases where the renal function is at least partly impaired or reduced.

In various embodiments, an AP-based agent may be used to treat or prevent congestive heart failure. In various embodiments, an AP-based agent may be used to treat or prevent one or more symptoms of congestive heart failure, such as shortness of breath, feeling tired, and leg swelling. In various embodiments, an AP-based agent may be used to treat or prevent congestive heart failure caused by coronary artery disease including a previous myocardial infarction (heart attack), high blood pressure, atrial fibrillation, valvular heart disease, excess alcohol use, infection, and cardiomyopathy of an unknown cause. In various embodiments, an AP-based agent may be used to treat or prevent class I congestive heart failure. In various embodiments, an AP-based agent may be used to treat or prevent class congestive heart failure. In various embodiments, an AP-based agent may be used to treat or prevent class Ill congestive heart failure. In various embodiments, an AP-based agent may be used to treat or prevent class IV congestive heart failure.

In various embodiments, an AP-based agent may be used to treat or prevent chronic fatigue syndrome, including myalgic encephalomyelitis (ME) and, more recently, systemic exertion intolerance disease (SEID). In various embodiments, an AP-based agent may be used to treat or prevent one or more symptoms of chronic fatigue syndrome, including fatigue, loss of memory or concentration, sore throat, enlarged lymph nodes of the neck or armpits, unexplained muscle pain, joint pain, headache, unrefreshing sleep, and extreme exhaustion lasting more than 24 hours after physical or mental exercise.

In various embodiments, an AP-based agent may be used to treat or prevent pancreatitis. In various embodiments, the pancreatitis is mild acute pancreatitis. In various embodiments, the pancreatitis is severe pancreatitis, for instance associated with organ failure, necrosis, infected necrosis, pseudocyst, and abscess. In various embodiments, an AP-based agent may be used to treat or prevent one or more symptoms of pancreatitis, such as epigastric or vague abdominal pain that may radiate to the back, serum amylase or lipase levels >about 3 times the upper limit of normal, and an imaging study with characteristic changes(e.g. CT, MRI, abdominal ultrasound or endoscopic ultrasound).

In various embodiments, an AP-based agent may be used to treat or prevent pancreatitis, in a subject having one or more risk factors, such as: gall stones, ethanol consumption, trauma, steroid consumption, mumps infection, autoimmune disease, scorpion stings, hyperlipidemia, hypothermia, hyperparathyroidism, endoscopic retrograde cholangiopancreatography, and use of certain drugs (e.g. azathioprine, valproic acid).

Several scoring systems are used to predict the severity of an attack of pancreatitis. Examples include APACHE II, Ranson, BISAP, and Glasgow. In various embodiments, the pancreatitis is defined by at least three of the following under the Modified Glasgow criteria: $pO2<60$ mmHg or 7.9 kPa; age >55; neutrophilia white blood cells >15; calcium <2 mmol/L; renal urea >16 mmol/L; enzymes lactate dehydrogenase (LDH) >600 iu/L aspartate transaminase (AST) >200 iu/L; albumin <32 g/L; and sugar glucose >10 mmol/L.

In some embodiments, the AP-based agent is used for reducing the incidence and/or severity of complications associated with administration of IV beta-lactam antibiotics to allo-HCT recipients, including, but not limited to, aGVHD and/or VRE colonization and/or infection.

In particular embodiments, the present invention provides for compositions and methods for preventing VRE colonization and/or infection. In some embodiments, methods of the invention prevent the gut dysbiosis associated with VRE colonization and/or infection.

In some aspects, a method of preventing VRE colonization and/or infection in a transplant recipient is provided that comprises administering the beta-lactamase agent of the invention.

In particular embodiments, the present invention provides for compositions and methods for reducing the incidence and/or severity of aGVHD. In various embodiments, the subject at risk for developing aGVHD is a transplant recipient. In further embodiments, the subject is a recipient of allo-HCT. In some embodiments, the subject is a recipient of one or more of bone marrow cells, peripheral blood cells, and umbilical cord cells. In various embodiments, the subject at risk for developing aGVHD is being administered or has been administered IV beta-lactam antibiotics.

In some embodiments, methods of the invention prevent the gut dysbiosis associated with aGVHD. In various embodiments, methods of the invention prevent the loss of gut microbiota diversity and/or intestinal dysbiosis associated with aGVHD. For example, methods of the present invention contemplate administration of compositions for modulating and/or reducing monodomination of any given bacterial strain (e.g., *Enterococcus*) associated with aGVHD. Further embodiments of the invention provide compositions and methods for preventing the decrease of microbiome diversity in subjects having undergone a transplant.

In some aspects, a method of reducing the incidence and/or severity of aGVHD in a transplant recipient is provided that comprises administering the beta-lactamase agent of the invention. For example, reducing the severity of aGVHD can include a patient receiving a grade less than IV, which is categorized as the most severe form of aGVHD.

In embodiments, the present methods relate to reducing the incidence and/or severity of aGVHD in a transplant recipient. In embodiments, the transplant recipient is a cancer patient, e.g. one who has received or is receiving radiation or chemotherapy and subsequently has received allo-HCT. In embodiments, the transplant recipient has blood or bone marrow cancer. In embodiments, the transplant recipient is the recipient of a hematopoietic stem cell transplant. In certain embodiments, the cancer is selected from leukemia, lymphoma, myeloma, and myelodysplasia. In certain embodiments, the cancer is selected from osteosarcoma, Ewing tumors, chordomas, and chondrosarcomas.

aGVHD is the deterioration of cells or tissues that are transplanted from a donor to a recipient due to the recognition by the immune system of the recipient that the cells or tissues are foreign. Thus, because Class I MHC are on more cells of the body, it is most desirable to transplant cells and tissues from people that have highest matching Class I MHC profiles followed by the highest matching Class II MHC profiles. Thus, in most transplant recipients, aGVHD is due to activation of the immune system to mismatched Class MHC molecules and other polymorphic proteins (minor histocompatibility antigens).

One option for treating cancers of the blood and bone marrow is to kill existing blood and marrow cells, e.g., through radiation or chemotherapy, and transplant similar cells from a healthy donor, referred to as an allogeneic hematopoietic stem cell transplant (allo-HCT).

In embodiments, the present methods relate to acute and chronic forms of GVHD. The classic acute or fulminant form of the disease (aGVHD) is typically observed within the first 100 days post-transplant, and is a major challenge to the effectiveness of transplants owing to the associated morbidity and mortality. The chronic form of graft-versus-host-disease (cGVHD) traditionally occurs after 100 days. The appearance of moderate to severe cases of cGVHD adversely influences long-term survival. After bone marrow transplantation, T cells present in the graft, either as contaminants or intentionally introduced into the host, attack the tissues of the transplant recipient after perceiving host tissues as antigenically foreign. The T cells produce an excess of cytokines, including TNF alpha and interferon-gamma (IFNγ). Tissue damage in cGVHD is primarily due to fibrosis. A wide range of host antigens can initiate graft-versus-host-disease, among them the human leukocyte antigens (HLAs). However, GVHD can occur even when HLA-identical siblings are the donors. aGVHD is characterized by selective damage to the liver, skin and mucosa, and the GI tract. Tissue damage in aGVHD is predominantly due to apoptosis. aGVHD severity is graded on a scale of I (mild) to IV (very severe) based on extent and type of lesion/rash (skin), diarrhea volume (GI), and serum bilirubin level (liver). cGVHD is characterized by a much broader tissue distribution than aGVHD. Skin and lungs are considered the primary target organs in cGVHD, along with the GI tract, liver, eyes, musculoskeletal system and hematopoietic system. A hyperacute and rapidly fatal form of aGVHD can occur within the first 2 weeks of allogeneic HCT, typically due to significant HLA mismatch or inadequate GVHD prophylaxis. Risk factors associated with cGVHD typically do not change after adjustment for prior aGVHD, suggesting that cGVHD is not simply an evolution of preceding aGVHD.

In embodiments, the present methods relate to reducing the incidence and/or severity of aGVHD. In embodiments, the present methods anticipate administration of the beta-lactamase to a patient who is treated with an IV beta-lactam antibiotic and has one or more risk factors of aGVHD, such as HLA "mismatch," or unrelated donor, older patient age, female donor to male recipient, intensity of the conditioning regimen or total body irradiation during conditioning regimen, and donor lymphocyte infusion. In embodiments, the present methods reduce the incidence and/or severity of aGVHD symptoms, such as skin rash, gastrointestinal (GI) tract disorders, and liver symptoms.

In embodiments, the present methods relate to GVHD as defined by one of more of the Billingham Criteria: 1) administration of an immunocompetent graft, with viable and functional immune cells; 2) the recipient is immunologically histocompatible; and 3) the recipient is immunocompromised and therefore cannot destroy or inactivate the transplanted cells.

In various embodiments, an AP-based agent may be used to treat or prevent allergies. In various embodiments, an AP-based agent may be used to treat or prevent atopic allergies, or IgE mediated allergies. In various embodiments, an AP-based agent may be used to treat or prevent one or more of hay fever, fur allergies, dust mite allergies, insect venom allergies, extrinsic asthma, and many types of food allergies. In various embodiments, an AP-based agent may be used to treat or prevent one or more of anaphylaxis, drug hypersensitivity, skin allergy, eczema, allergic rhinitis, urticaria, atopic dermatitis, dry eye disease, allergic contact allergy, food hypersensitivity, allergic conjunctivitis, insect venom allergy, bronchial asthma, allergic asthma, intrinsic asthma, occupational asthma, atopic asthma, acute respiratory distress syndrome (ARDS) and chronic obstructive pulmonary disease (COPD).

In various embodiments, an AP-based agent may be used to treat or prevent asthma, including without limitation allergic asthma. In various embodiments, AP-based agent may be used to reduce immunoglobulin E stimulation, airway hyper-reactivity, mast cell infiltration, pulmonary eosinophilia, and accumulation of alternatively activated macrophages in the lungs. In various embodiments, an AP-based agent may be used to treat or prevent one or more of recurrent wheeze and intermittent air flow limitation.

In some embodiments, the terms "patient" and "subject" are used interchangeably. In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish.

In various embodiments, methods of the invention are useful in treatment a human subject. In some embodiments, the human is a pediatric human. In other embodiments, the human is an adult human. In other embodiments, the human is a geriatric human. In other embodiments, the human may be referred to as a patient. In some embodiments, the human is a female. In some embodiments, the human is a male.

In certain embodiments, the human has an age in a range of from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

Kits

The invention provides kits that can simplify the administration of the modified-release formulation described herein. The kit is an assemblage of materials or components, including at least one of the modified-release formulations described herein. The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to affect a desired outcome, such as to treat a disorder associated described herein. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner store in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label which indicates the contents and/or purpose of the kit and/or its components.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50%" covers the range of 45% to 55%.

An "effective amount," when used in connection with medical uses is an amount that is effective for providing a measurable treatment, prevention, or reduction in the rate of pathogenesis of a disorder of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents (e.g., beta-lactamases and/or additional therapeutic agents described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures, tissue samples, tissue homogenates or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/ or uses in the manufacture of a medicaments for treating the diseases or disorders described herein.

EXAMPLES

Example 1: Development of IAP Delayed-Release Enteric-Coated Pellets

Two batches of IAP layered sucrose cores were prepared at enzyme loads of 3.45% w/w (first batch) and 4.65% w/w (second batch). The IAP activity post layering was maintained when compared to that of the IAP solution used for layering. The IAP solution presented an activity of ca. 70% against a Sigma standard while the drug layered cores presented 60% against the Sigma standard.

Drug layered cores batch 1 were studied to assess the stability of IAP by activity assay. Cores were stored under refrigerated conditions in the presence and absence of silica desiccant and it was found that the IAP activity remained stable over a period of 8 weeks under both conditions. Drug layered cores batch 2 were then coated to a 30% EUDRAGIT L30D-55 weight gain (single layer) or to a 7% HPC weight gain as an inner isolation layer followed by 30% EUDRAGIT L30D-55. Both coated formulations presented acid resistance in fasted state simulated gastric fluid (FaSSGF) for 2 hours and very similar dissolution profiles in fasted state simulated intestinal fluid (FaSSIF) without loss in enzyme activity at the end of dissolution testing.

The coated pellets were stored under refrigerated conditions in the presence of silica and, after 6 months, the enzyme activity was not reduced which suggested that the HPC (binder) and the coating layer (acidic polymer EUDRAGIT L30D-55) had no impact on the enzyme activity during these 6 months.

Overall, the drug layered pellet formulation is a promising option to formulate IAP, due to the dissolution profiles obtained and the good flowability of the pellets. Another advantage of it is the flexibility to obtain various enzyme strengths based on one formulation. It also provides a simplified method because the layering and enteric coating can be performed in the same fluid bed coater.

Example 2: Assessment of Excipient-CAP Compatibility

IAP was combined with a selection of potential binders to determine the effect of the binder on IAP activity. The binders tested for compatibility with IAP in the presence of sucrose or lactose did not significantly change the IAP activity after 96 hours of incubation and showed similar % activity as the initial IAP solution alone (IAP-binder combination #11) as shown in Table 1 and FIG. 2.

TABLE 1

IAP-binder combination numbers and composition.

| IAP-binder Combination # | IAP | Binder at 11.0 mg/mL | Sugar | Salts |
|---|---|---|---|---|
| 1 | 5.50 mg/mL | — | Sucrose 5.50 mg/mL | 1.25 mg/mL |
| 2 | | HPC | | |
| 3 | | PEG4000 | | |
| 4 | | PEG8000 | | |
| 5 | | Kollicoat IR | | |
| 6 | | — | Lactose | |

TABLE 1-continued

IAP-binder combination numbers and composition.

| IAP-binder Combination # | IAP | Binder at 11.0 mg/mL | Sugar | Salts |
|---|---|---|---|---|
| 7 | | HPC | 5.50 mg/mL | |
| 8 | | PEG4000 | | |
| 9 | | PEG8000 | | |
| 10 | | Kollicoat IR | | |
| 11 | | — | — | |

As shown in Table 1 and FIG. 2, the majority of combinations did not result in a significant change in enzyme activity when compared to the initial value at t=0 hours. The results showed that under the current testing conditions, a loss of IAP activity was not observed in the presence of any of the tested excipients so no incompatibility issues were identified. The results suggested that the drug layered cores using HPC as a binder would not compromise the IAP activity and this was the suggested combination selected for further studies.

Figure 3:
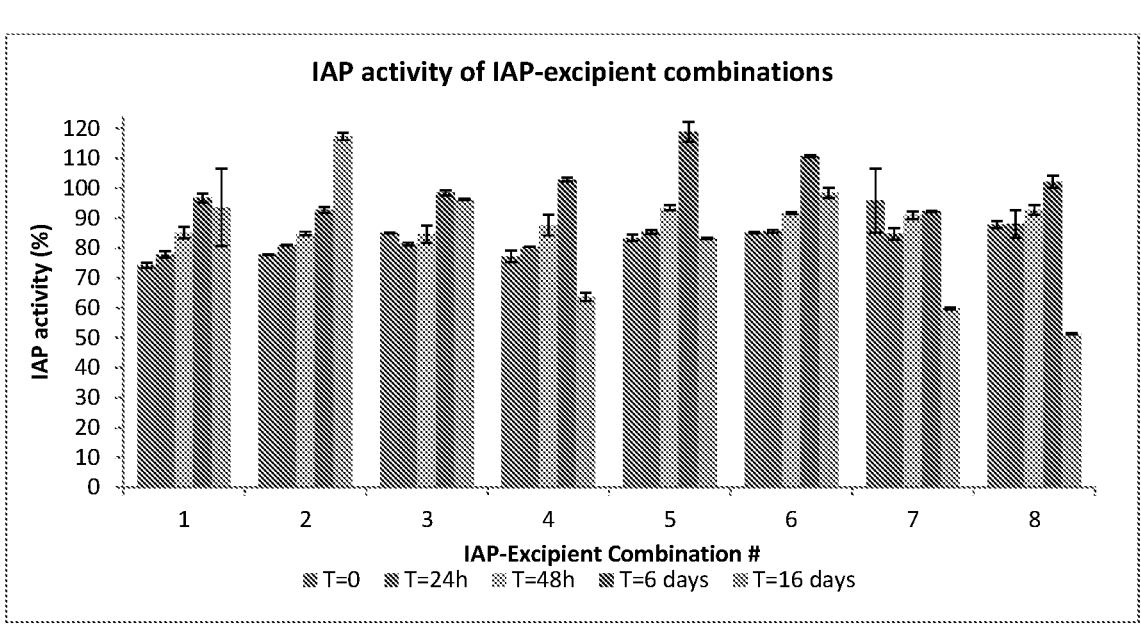
FIG. 3 depicts the IAP activity over 16 days in a IAP-excipient evaluation. In each set of histograms, various time-points are presented, from left-most to right-most bar each bar represents 0 hours, 24 hours, 48 hours, 6 days, and 16 days.

The co-factors tested for compatibility with IAP are shown in Table 2 and FIG. 3. It was found that the co-factors did not significantly increase IAP activity under the current testing condition.

TABLE 2

IAP-excipient combination numbers and compositions.

| IAP-excipient Combination # | IAP | HPC | Sucrose | Co-factor | Salts |
|---|---|---|---|---|---|
| 1 | 5.50 mg/mL | — | — | — | 1.25 mg/mL |
| 2 | 11.0 mg/mL | — | — | | |
| 3 | | 11.0 mg/mL | 5.50 mg/mL | — | |
| 4 | | — | | — | |
| 5 | | 11.0 mg/mL | | $CoCl_2$ (2.75 mM) | |
| 6 | | | | $CoCl_2$ (5.5 mM) | |
| 7 | | | | $CaCl_2$ (2.75 mM) | |
| 8 | | | | $CaCl_2$ (5.5 mM) | |

As shown in Table 2 and FIG. 3, the first four combinations (#1-#4) without any co-factors present did not show a decreased trend in IAP activity when compared to the four combinations containing a co-factor (#5-#8). Similar to the IAP-binder compatibility study (results provided in FIG. 2), the results of the IAP-co-factor compatibility study have confirmed that the IAP activity would not be compromised in the presence of HPC, sucrose or the combination of both. The addition of co-factors to the formulation did not significantly increase the IAP activity across the different time points. Therefore, co-factor containing formulations were not further investigated. The IAP buffer solution contains 1.0 mM $MgCl_2$ and 0.1 mM $ZnCl_2$. The additional metal ions tested in these experiments ($CoCl_2$ and $CaCl_2$) did not alter the enzyme activity of the IAP-binder mixtures.

The excipient/IAP mixture solutions were incubated at 37° C. and therefore, due to the temperature of incubation, aqueous media had evaporated over time and apparent loss of solution volume was observed. This led to an increase of enzyme activity in combination #2 at the final time point.

The decrease of enzyme activity in combination #4, #5, #7 and #8 at the final time point could be related to the assay variability.

Example 3: Stability Testing of First Batch of Cores

IAP solution was supplied frozen as a 10.1 mg/mL IAP (Intestinal Alkaline Phosphatase) in 20 mM Tris, 0.1 mM ZnSO4 and 1 mM MgCl2 buffer at a pH of 7.5 and was utilized for drug layering. To prepare the final drug layering solution, 1.12 g of HPC (Klucel EF) was added into 49.5 mL IAP solution under slow magnetic stirring (below 200 RPM). The subsequent solution was spray-layered onto 6.00 g of 600/710 μm Suglets in a Caleva mini-coater/drier.

The IAP-HPC solution was sprayed at an atomisation air pressure of 0.8 bar with an inlet air speed of 11.5 m/s and a chamber agitation rate of 10.5 Hz. The spraying process temperature was 45° C. for the initial 30-45 minutes, then lowered to 40° C. This was because, during the early stages of the coating process, the Suglets aggregate easily if the temperature was not sufficient to quickly dry the aqueous solution on the surface of cores. As the coating process progressed, the cores possessed a thin layer of coating, which protected the cores and led to a reduction in the chance of aggregation and, as a result, the process temperature was lowered.

The drug layered cores were dried at 35° C. for 30 minutes post every 1 hour of spraying and, once coating had been completed, the drug layered cores were additionally dried at 40° C. for 1 hour before the actual weight gain was confirmed.

Drug layered cores (AP0361/24/1) were composed of Suglets/IAP/HPC/salts (from IAP solution) at 87.92/3.45/7.77/0.87% w/w respectively. This batch of cores had a slightly different ratio of IAP/HPC at 1:2.25 w/w, rather than the intended 1:2 w/w ratio, due to a preparation error. The cores were stored at 2-8° C. in a closed glass vial containing silica desiccant bags after the drug layering process was completed.

The resulting cores were kept in a closed vial under desiccation at 2-8° C. for the first 12 days after drug layering. To study the effect of a non-desiccated condition, half of the contents were removed, after the initial desiccated 12 days, from the glass vial and stored at 2-8° C. without presence of silica sacks. Enzyme activity results measured over time in a short-term stability study of these drug layered cores, as shown in Table 3.

TABLE 3

| IAP activity of drug layered cores in the refrigerator under dessicated/non-dessicated conditions. | | |
|---|---|---|
| Days of storage in refrigerator | % Activity | |
| — | 72.1 (IAP solution) | |
| 3 | 71.3 (Desiccated) | |
| 12 | 45.2 (Desiccated) | |
| From 12 days | Desiccated | Non-desiccated |
| 27 | 74.7 | 68.3 |
| 35 | 73.1 | 73.4 |
| 42 | 63.6 | 65.4 |
| 54 | 61.5 | 55.4 |

Some fluctuations in the % IAP activity over time were observed; however, these could be related to the variability of the assay method. Based on the results in Table 3, it was concluded that the non-desiccated condition had not reduced the IAP activity significantly when compared to the desiccated condition.

For the enzyme activity test, the cores were dissolved into diethanolamine buffer. Specifically, an IAP activity assay method was performed. A 140 mg/mL solution in purified water using diethanolamine (Sigma D8885) was prepared and the pH of the diethanolamine adjusted to 9.8 at 37° C. with 5 M HCl. The pH adjusted solution was diluted to a final diethanolamine concentration of 105 mg/mL with purified water. Finally, 500 μL/L of 1 M magnesium chloride solution (Sigma M1028) was added to the solution. The diethanolamine was prepared fresh and protected from direct sunlight.

The IAP enzyme standard solution was prepared by diluting from the 19.4 mg/mL stock solution (concentration may vary between different lots from Sigma) to 1.00 mg/mL in diethanolamine buffer (5 μL in 92 μL diethanolamine buffer). The enzyme solution was kept on ice before further dilution. This purified intestinal alkaline phosphatase (Sigma #PO114) was used as a control to test the activity of assayed samples.

All samples were loaded onto a 96-well plate, including the Sigma standard and IAP solution, and were diluted to a theoretical 5 ng/mL solution with diethanolamine buffer.

pNPP was reconstituted (Abcam ab146203) at 1.86 mg/mL assay buffer for a 5 mM solution, and the pNPP solution was stable for 12 hours on ice.

The kinetic assay was then performed. On a plate reader (DYNEX #MRX TC II), 80 μL standards and samples were added to the wells of a 96-well plate. All enzyme reactions were run in duplicate wells. Sufficient 5 mM pNPP solution was added in each of the empty wells for later addition to samples and the plate was incubated at 37° C. for 5 minutes. Quickly, 50 μL of pre-warmed 5 mM pNPP solution was added to each well containing either standards or samples using a multichannel pipette. During this addition, the formation of air bubbles was avoided. The reaction sequence was initiated and carried out at 37° C. After an additional 10 minutes initial delay and a 2 second initial shaking step, the colorimetric output (pNPP NPP dephosphorylation via enzyme phosphatase activity) was measured every 20 seconds over 5 minutes as a function of the optical density (OD) increase at 405 nm. Blank wells containing no enzyme were run in parallel on the same plate.

The kinetic assay provided a readout of enzyme kinetics over this time period and the slope was used for comparison to the slope generated from the IAP Sigma standard (% activity of the sample=slope of sample/slope of Sigma standard*100%; the slope of blank was subtracted from the slope of sample and Sigma standard).

Example 4: Enteric Coating and Dissolution Testing of Second Batch of Cores

Drug layered cores of the second batch were prepared for coating trials and manufactured following the same equipment parameters as the first batch of cores (Example 3). The second batch of cores was composed of Suglets/IAP/HPC/salts (from IAP solution) at 84.9/4.7/9.3/1.2% w/w. The drug layering solution was prepared using 0.948 g of HPC (Klucel EF) which was added into 47.0 mL IAP solution under slow magnetic stirring (below 200 RPM) with a IAP:HPC ratio of 1:2 w/w.

Two types of coating were applied onto the second batch of drug layered cores, which were either 30% weight gain of EUDRAGIT L30D-55 (single enteric layer) or 7% weight gain layer of HPC followed by an outer layer of 30% polymer weight gain of EUDRAGIT L30D-55 (enteric layer with sub-coat). The formulations are listed in Table 4.

TABLE 4

Composition of formulations of second batch
of drug layered cores with enteric coatings.

| Component | Single layer % Total | Double layer % Total |
|---|---|---|
| Sucrose core ("Suglet") | 84.9 | 84.9 |
| Hydroxypropylcellulose | 9.3 | 9.3 |
| Salts | 1.2 | 1.2 |
| IAP (SYN-020) | 4.7 | 4.7 |
| EUDRAGIT L30D-55 weight gain | 30 | 30 |
| HPC subcoat weight gain | 0 | 7 |

Figure 4:
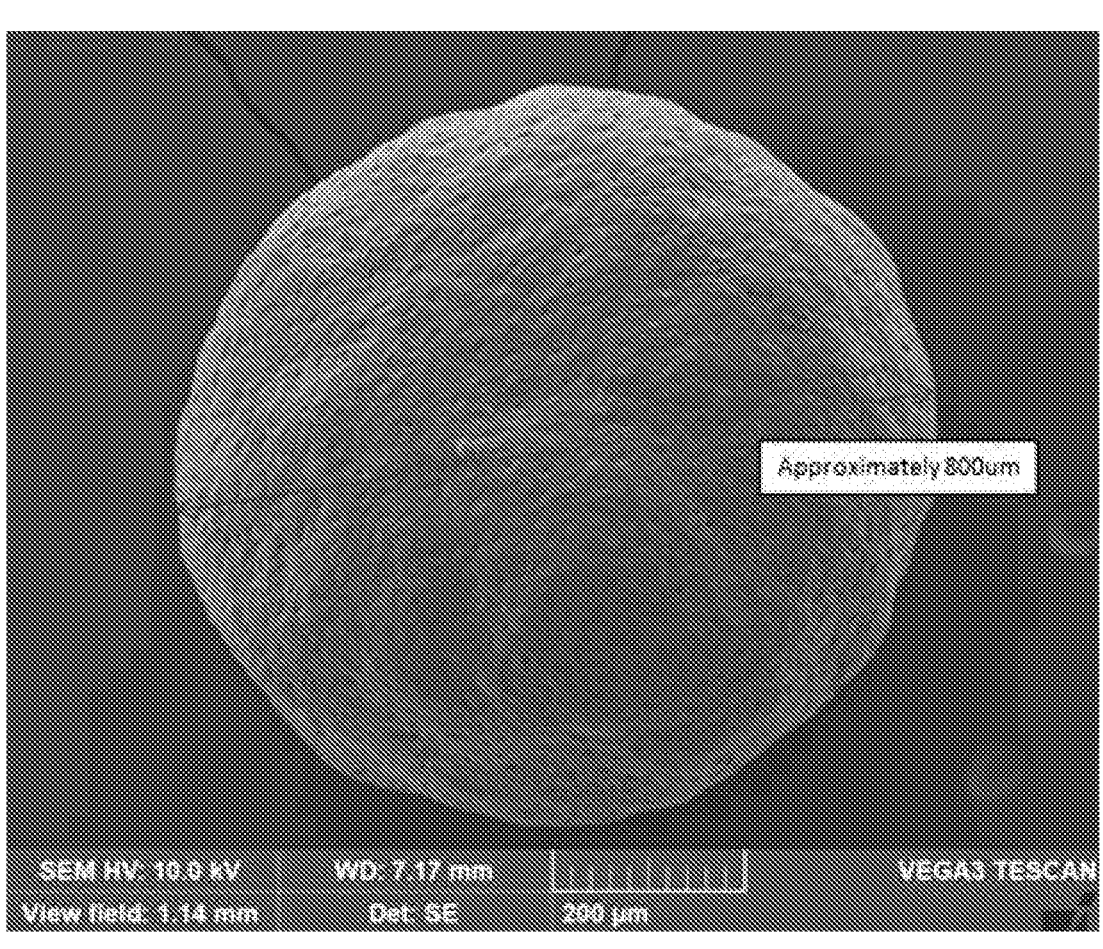
FIG. 4 depicts an SEM picture of one coated pellet (30% EUDRAGIT L30 D-55 coated on pellets).

The Drug layered cores (batch 2) were layered with IAP/HPC at a 1:2 w/w solid ratio and a final composition of 4.65% weight gain of IAP, followed by a single layer coating (30% weight gain of EUDRAGIT L30D-55) or a double layer coating (7% weight gain of HPC+30% weight gain of EUDRAGIT L30D-55). The diameter of the single layer coated pellets was approximately 800 μm as shown in the SEM image in FIG. 4. FIG. 4 depicts the SEM picture of one coated pellet (30% EUDRAGIT L30D-55 coated on second batch of pellets).

Figure 5:
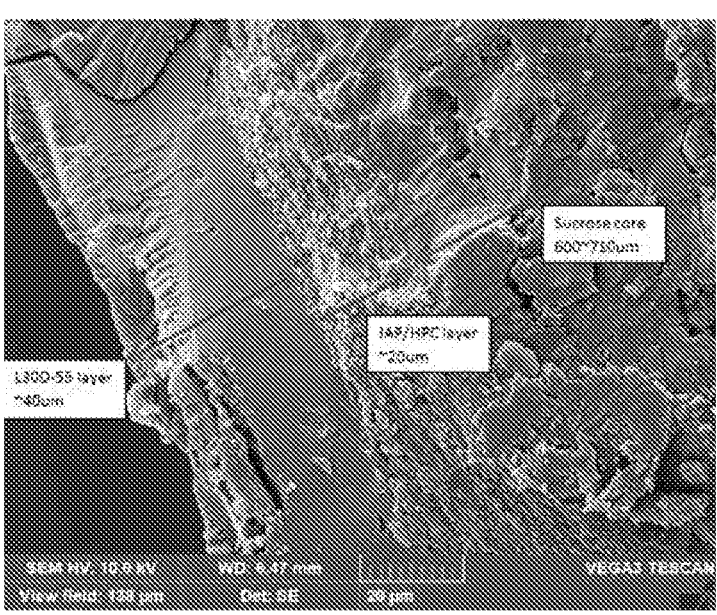
FIG. 5 shows an SEM picture of cross-section of one coated pellet (30% EUDRAGIT L30 D-55 coated on pellets).

The cross-section of a pellet from the second batch is also shown in FIG. 5, where the sucrose core, IAP/HPC layer and the L30D-55 coating layer can be clearly distinguished. The thickness of the IAP/HPC layer was ca. 20 μm and the thickness of EUDRAGIT L30D-55 coating layer was ca. 40 μm (recommended thickness by the polymer manufacturer, Evonik). FIG. 5 depicts an SEM picture of cross-section of one coated pellet (30% L30D-55 coated on second batch of pellets).

The dissolution behavior of these coated pellets was studied. The quantity of pellets in each dissolution vessel was 1.14 g of the single layer coated pellets and 1.22 g of the double layer coated pellets, which correspond to an IAP quantity of 40 mg for both formulations. In each dissolution test, one tablet was incubated in 20 mL FaSSIF pH 1.6 in a 60 mL vial at 37° C. and 200 RPM orbital shaking on a heater/shaker for 2 hours. After the initial 2 hours, 20 mL of double strength FaSSIF was added and the pH was adjusted to 5.5 or 5.8 using 1 M NaOH. After an additional 45 minutes, the pH was further adjusted to 6.5 or 6.8 and the dissolution test proceeded for an additional 2-3 hours.

The coated pellets were tested in FaSSGF at pH 1.6 for 2 hours followed by an addition of FaSSIF to reach pH 5.8 for 45 minutes and then increased to pH 6.8 for an additional 3 hours. The dissolution testing of the coated pellets in FaSSIF alone (pH 5.8 for 45 minutes followed by pH 6.8 for 3 hours) was also conducted for comparison.

Figure 6:
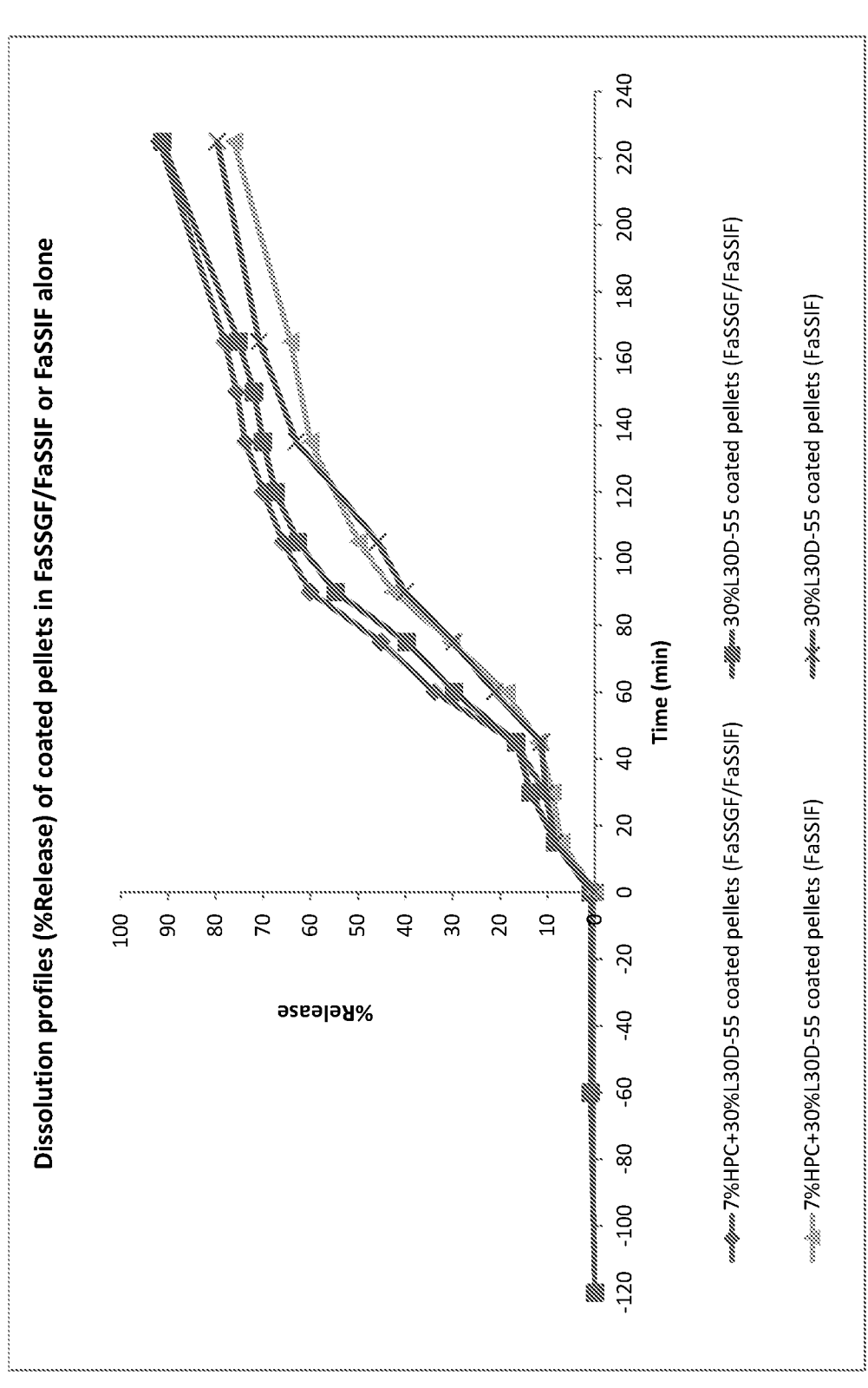
FIG. 6 depicts the percent release from two formulations of coated IAP pellets in a dissolution apparatus containing fasted state simulated gastric fluid (FaSSGF)/fasted state simulated intestinal fluid (FaSSIF) or FaSSIF alone by UV analysis.

The UV protein release profiles are shown in FIG. 6. The % release of IAP during dissolution in FaSSIF alone is presented as the "x" and "triangle" profiles for the single and double layer coatings, respectively. The % release of IAP during FaSSGF and FaSSIF dissolution is presented as the red and blue profiles for the single and double layer coating, respectively.

The profiles indicated that the coated pellets were enterically protected at low pH as no IAP release was detected in FaSSGF by UV analysis. Moreover, the dissolution profiles between the single-stage and the double-stage approaches were very similar—release started to occur immediately after the pellets were exposed to pH 5.8 FaSSIF and, after 45 minutes at pH 5.8, the dissolution rate increased when the pH was adjusted to pH 6.8. Full release was achieved after a further 3 hours at pH 6.8.

Figure 7:
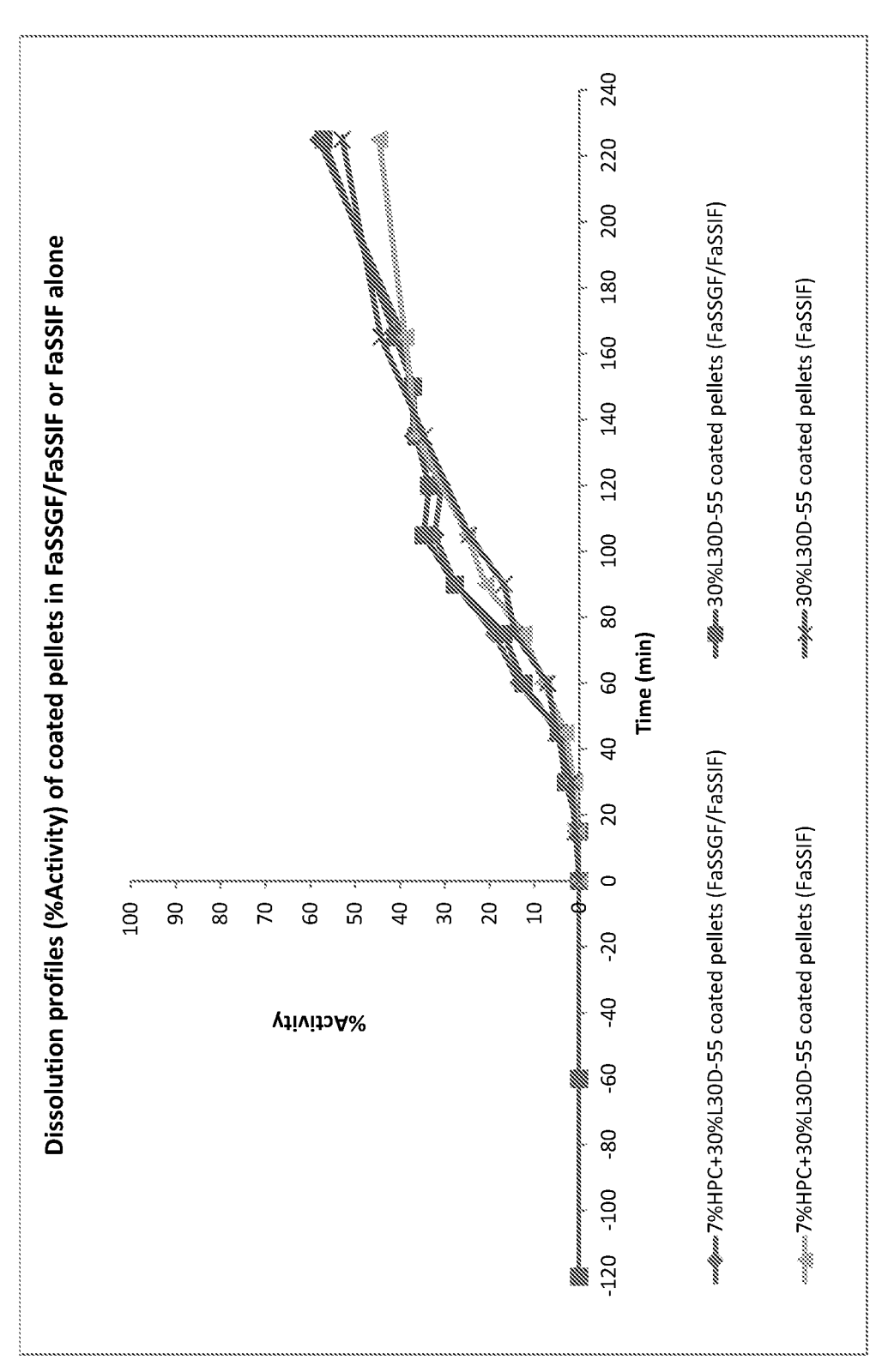
FIG. 7 shows percent activity of coated pellets in FaSSGF/FaSSIF or FaSSIF alone by enzymatic assay.

The enzyme activity profiles are shown in FIG. 7. The % activity of IAP during dissolution in FaSSIF alone is presented as the "x" and "triangle" profiles for the single and double layer coatings, respectively. The % activity of IAP during FaSSGF and FaSSIF dissolution is presented as the red and blue profiles for the single and double layer coating, respectively.

The enzyme activity profiles followed the same trend as the % IAP release by UV in FIG. 6. The maximum enzyme activity detected at the end point of both dissolution tests was ca. 45%-55% which was at the same level as the starting material (ca. 50% of the drug layered cores). The results indicated that the coatings applied were enterically protected at low pH, and that the enzyme activity was not reduced in the presence of coating polymer. Due to the similarity in the dissolution profiles produced by the single and double coating layered cores, it was concluded that the sub-coat HPC was not required to isolate and protect the enzyme from acidic coating polymer.

The % activity achieved by exposing pellets to FaSSIF alone was similar to that exposed to FaSSGF/FaSSIF, which indicated that the IAP in the coated pellets has not been affected or denatured by FaSSGF pH 1.6. This confirmed that sufficient enteric coating thickness was applied as the same level of enzyme activity was obtained.

The study showed that enteric coating of layered cores with 30% polymer weight gain EUDRAGIT L30D-55 aqueous dispersion provided acidic resistance in FaSSGF for periods of up to 2 hours and a sustained release of IAP over 4 hours in FaSSIF. The presence of a 7% HPC isolation layer did not change the dissolution profiles, nor did it impact the enzyme activity. Therefore, the isolation sublayer was judged to be not required.

Example 5: Stability Assessment of IAP Activity in Pellets

The uncoated/coated Drug layered cores were placed at 2-8° C. in closed glass vials containing silica desiccant bags for a period of up to 12 months for stability assessment. The enzyme activity was monitored on these cores at 0, 1, 3, and 6 months by dissolving the cores into diethanolamine buffer and analysing the IAP activity.

The uncoated and coated pellets were both stored at refrigerated temperatures under desiccation. The enzyme activity was measured over a period of up to 6 months and the results are shown in Table 5.

TABLE 5

| Stability of IAP activity in uncoated/coated drug layered pellets when stored at 2-8° C. under desiccation. | | | | |
|---|---|---|---|---|
| | Duration of Storage | | | |
| | 0 | 1 month | 3 months | 6 months |
| Samples | | % Activity Average | | |
| Uncoated pellets | 56.69 ± 4.23 | 52.37 ± 1.81 | 58.45 ± 0.97 | 63.2 ± 1.73 |
| 7% HPC + 30% L30D-55 coated pellets | 48.77 ± 2.90 | 46.93 ± 0.39 | 57.94 ± 5.35 | 56.1 ± 0.67 |
| 30% L30D-55 coated pellets | 48.80 ± 0.17 | 49.50 ± 0.97 | 58.47 ± 2.66 | 58.3 ± 4.65 |

The results show that enzyme activity of the uncoated cores and coated pellets remained at the same level over 6 months of storage at refrigerated temperatures under desiccation.

Example 6: Stability Assessment of 25 Ma and 5 Ma IAP Pellet Capsules

Size 2 HPMC transparent capsules were filled with coated IAP pellets, which presents 9.7% w/w drug load (analysed by UV spectrometer) and 78.1% enzyme activity relative to Sigma standard (analysed by DYNEX microplate reader). 90 capsules contained 25 mg IAP, 90 capsules contained 5 mg IAP. The pellets were manufactured by layering IAP/HPC (1/2 w/w) onto 600/710 μm Suglets (Colorcon), followed by EUDRAGIT L30D-55 (Evonik) coating.

TABLE 6

| Compositions of capsules containing 5 mg and 25 mg of IAP | | | | |
|---|---|---|---|---|
| | 5 mg capsule | | 25 mg capsule | |
| Component | mg | % Total | mg | % Total |
| Sucrose core | 19.5 | 37.7 | 97.3 | 37.7 |
| Hydroxypropylcellulose | 10.0 | 19.4 | 50.0 | 19.4 |
| Salts | 1.3 | 2.4 | 6.3 | 2.4 |
| IAP (SYN-020) | 5.0 | 9.7 | 25.0 | 9.7 |
| EUDRAGIT L30D-55 | 13.5 | 26.3 | 67.7 | 26.3 |
| HTP-20 | 2.3 | 4.5 | 11.5 | 4.5 |
| Subtotal | 51.6 | 100.0 | 257.7 | 100.0 |
| HPMC capsule #2 | 60.0 | — | 60.0 | — |
| Total | 111.6 | — | 317.7 | — |

The stability and percent activity of the pellet capsules over the course of one-year duration of storage in a refrigerator is displayed in Table 7 below.

TABLE 7

| Pellet capsule activity over the course of one year. | |
|---|---|
| Duration of storage at 2-8° C. | % Activity (vs. IAP standard) |
| 0 (manufactured date) | 93.0 |
| 1 month | 93.8 |
| 3 months | 87.3 |
| 6 months | 83.4 |
| 12 months | 79.7 |

The present inventors surprisingly discovered that the IAP pellet capsules maintained about at least 80% IAP activity when stored at 2-8° C. over the course of one year.

In vitro dissolution testing was then performed. Approximately 450 mg of coated pellets were incubated in 25 mL FaSSGF (pH 1.6, 37° C.) in a 60 mL glass vial, the vial was shaken gently at 200 RPM orbital shaking speed on a heater/shaker. At 60 and 120 minutes, 1 mL of the media was withdrawn through a 10 μm cannula filter and was filtered through 0.2 μm for UV analysis. 50 NL of the filtered solution was frozen for further activity analysis. The solution was placed back to the vial afterwards.

After the initial 2 h incubation in FaSSGF, 25 mL of FaSSIF was added to the vial to obtain pH 5.8. The samples were taken every 15 minutes. After 45 minutes, the pH was adjusted to 6.8 and samples were taken every 15 minutes. The sampling approach was the same as described in the above paragraph.

Figure 8:
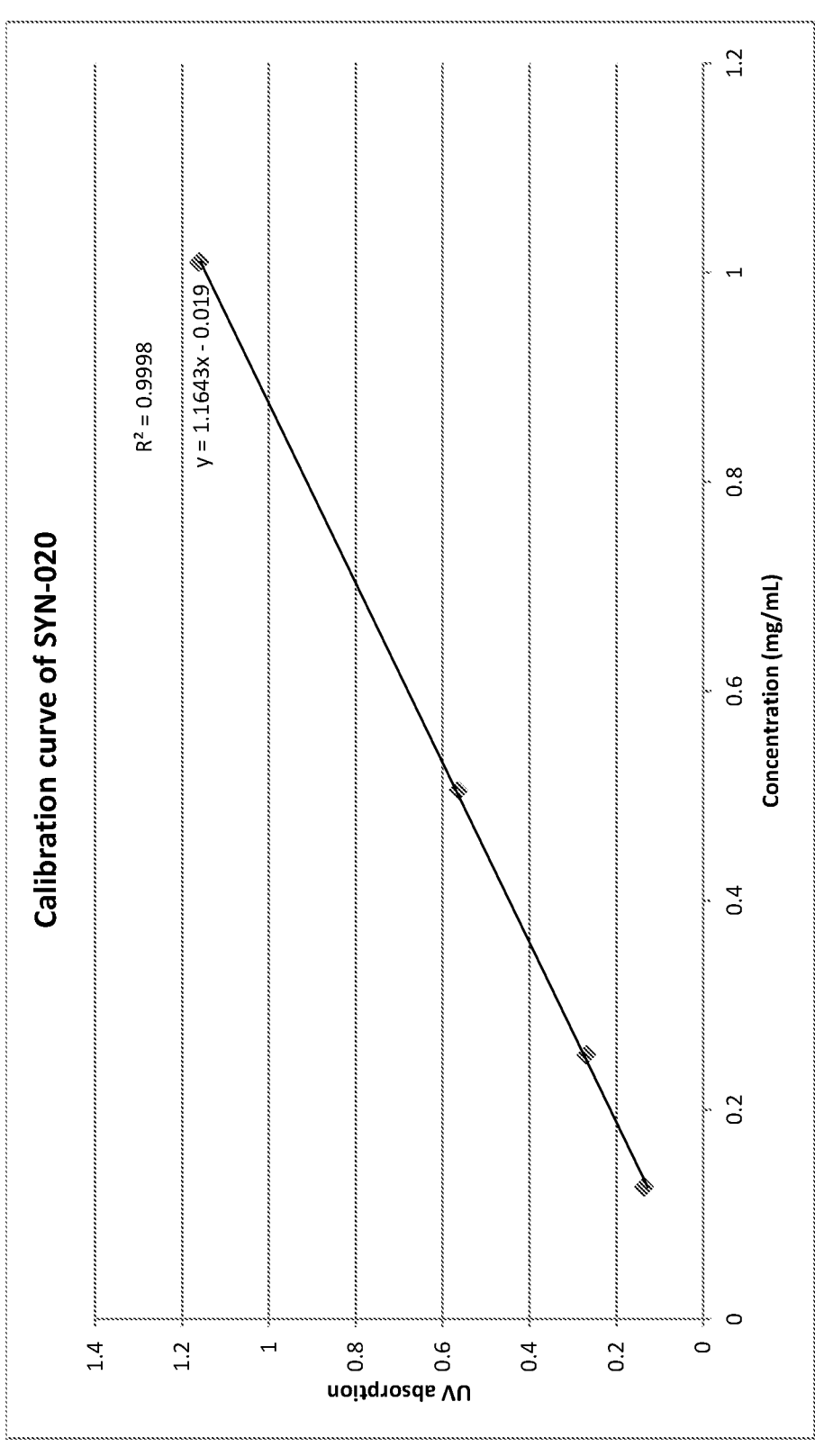
FIG. 8 shows a calibration curve that was generated for calculating sample concentrations at various time points based on the equation of the linear trend line. "SYN-020" is synonymous with IAP (i.e., SEQ ID NO: 39).

The filtered samples were analysed in UV spectrometer at 280 nm and 320 nm and the absorption value equals to A280-A320. The absorption from the blank media was further subtracted from the sample absorption value and, the subsequent value was used for % release calculation. A calibration curve was firstly generated as shown in FIG. 8. The sample concentration at each time point was calculated based on the equation of the linear trend line.

Figure 9:
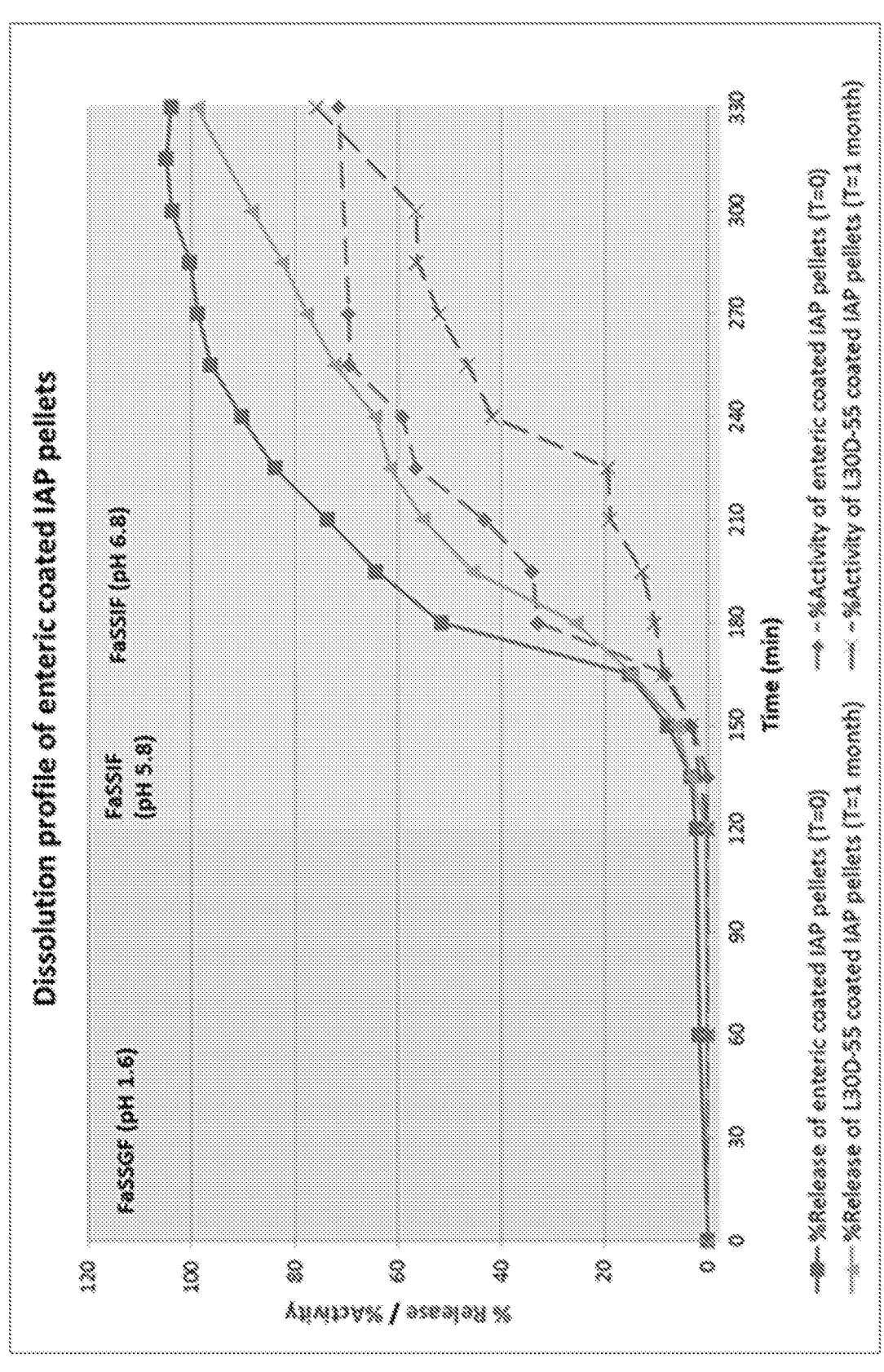
FIG. 9 depicts stability results using dissolution testing of the coated pellet capsules after one month.

The results of the dissolution testing are depicted in FIG. 9. The coated pellets were resistant to FaSSGF for 2 hours as no release was detected. The % release at 60 and 120 minutes (T=0, red line) was approximately 1%. In addition, the pellets had full activity recovered at the end of the dissolution testing, which indicates that acid did not penetrate through the coating film during the initial incubation. The IAP release was slow during the first 45 minutes in FaSSIF at pH 5.8, as the pH was close to 5.5, the dissolution threshold of EUDRAGIT L30D-55. Once the pH was adjusted to 6.8, the coating film started to dissolve rapidly and the IAP release increased dramatically.

Figure 10:
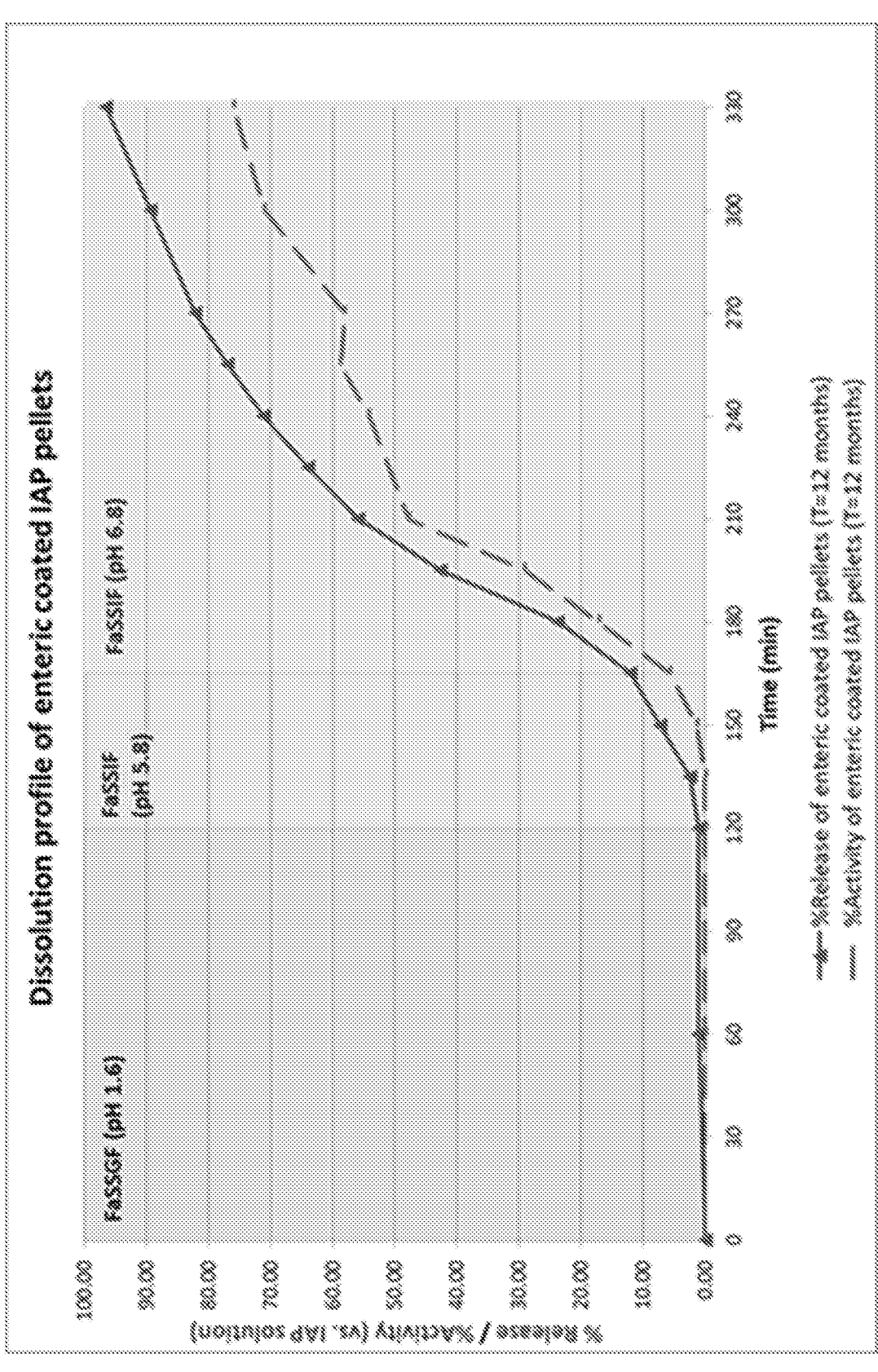
FIG. 10 shows the results of a dissolution test in which the coated pellets have been stored for about one year.

FIG. 10 describes the results of a dissolution test in which the coated pellets have been stored for about one year. The coated pellets were resistant to FaSSGF for 2 hours as no release was detected. The percent release at 60 and 120 minutes (T=0, red line) was approximately 1%. In addition, the pellets had full activity recovered at the end of the dissolution testing, which indicates that acid did not penetrate through the coating film during the initial incubation. The IAP release was slow during the first 45 minutes in FaSSIF at pH 5.8, as the pH was close to 5.5, the dissolution threshold of EUDRAGIT L30D-55. Once the pH was adjusted to 6.8, the coating film started to dissolve rapidly and the IAP release increased dramatically.

Various tests were performed on separate IAP pellet batches, including: non-GMP SYN-020 pellets; non-GMP SYN-020 pellets (HPD514-A-001); non-GMP SYN-020 capsule (5 mg); non-GMP SYN-020 capsule (15 mg); and GMP SYN-020 pellets. The composition of SYN-020 Delayed Release Capsule, 15 mg and 5 mg Capsule, and SYN-020 Placebo Pellets and the results of the various tests are depicted in Table 8 and Table 9 below.

TABLE 8

| Composition of SYN-020 Delayed Release Capsule, 15 mg and 5 mg Capsule. | | | | |
|---|---|---|---|---|
| | 15 mg Capsule | | 5 mg Capsule | |
| Component | mg | % Total | mg | % Total |
| Sucrose sphere | 58.35 | 38.9 | 19.45 | 38.9 |
| Hydroxypropyl cellulose | 30.00 | 20.0 | 10.00 | 20.0 |

TABLE 8-continued

Composition of SYN-020 Delayed Release
Capsule, 15 mg and 5 mg Capsule.

| | 15 mg Capsule | | 5 mg Capsule | |
|---|---|---|---|---|
| Component | mg | % Total | mg | % Total |
| SYN-020 | 15.00 | 10.0 | 5.00 | 10.0 |
| Buffer salts | 0.45 | 0.3 | 0.15 | 0.3 |
| EUDRAGIT L30 D-55 | 39.45 | 26.3 | 13.15 | 26.3 |
| HTP-20 | 6.75 | 4.5 | 2.25 | 4.5 |
| Subtotal | 150.0 | 100.0 | 50.0 | 100.0 |
| Hard HPMC capsule #3 | 8.0 | | 8.0 | |
| Total | 198.0 | | 98.0 | |

HTP-20 is a pre-mixed formulation of Glyceryl monostearate, Polysorbate-80, and Triethyl citrate that provides anti-tacking, plasticizer, and stabilizer functions.

FIG. 11A-H depicts additional analysis of the non-GMP SYN-020 5 mg and 15 mg capsule dosages. The results regarding dosage strength and stability, including parameters such as specific activity, purity, water content, and dissolution, were analyzed through 6 months.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to

TABLE 9

Batch analysis for SYN-020 IAP coated pellets and capsules

| | Batch Information | | | | |
|---|---|---|---|---|---|
| Test Method | Non-GMP SYN-020 pellets, AP0361 Result | Non-GMP SYN-020 pellets Result | Non-GMP SYN-020 capsule, 15 mg Result | GMP SYN-020 pellets Result | GMP SYN-020 capsule, 15 mg Result |
| Appearance | | | | | |
| Capsule Color | Clear | n.a. | Clear, size 3 | n.a. | White, opaque, size 3 |
| Capsule Content | | | | | |
| Color | Light yellow | Slightly yellow pellets | n.d. | n.a. | Slightly yellow pellets |
| Flowability | n.d. | Free flowing | | | Free flowing |
| Particle Size Distribution | n.d. | 98% | n.a. | 100% | n.a. |
| Enzyme Activity by pNPP/IAP Assay | 93.0% relative to SYN-020 solution | 616 Units/mg | n.d. | 612 Units/mg | n.d. |
| Protein Content by A280 nm | 9.7% | 10% | n.d. | 9.9% | n.d. |
| Content Uniformity by pNPP/IAP Assay | n.a. | n.d. | 681 Units/mg, Complies | n.d. | 614 Units/mg, Complies |
| In Vitro Dissolution Detection by RP-HPLC | 0% at 2 hours at 0.1N HCl; 94% at 1 hr at pH 6.8; 87% at 0.75 hour; 95% at 2 hours | n.d. | 0% at 2 hrs at 0.1N HCl; 82% at 1 hr at pH 6.8; 47, 84%, 93%, 86% at 0.25, 0.5, 0.75, and 1.25 hr | n.a. | <1% at 2 hrs at 0.1N HCl; 88% at 1 hr at pH 6.8; 53%, 87%, 88%, 91% at 0.25, 0.5, 0.75, and 1.25 hr |
| Water Content, by Karl Fischer Method | n.d. | 3% | 3% | n.a. | 2% |
| RP-HPLC | | | | | |
| Purity | n.d. | 85.1% main peak | n.d. | n.d. | 79% main peak |
| Identity | | Main peak RRT comparable to reference standard | n.d. | | Main peak co-elutes ± 10% RRT of reference standard |
| Microbial Count | n.d. | | n.d. | n.d. | |
| Total Aerobic Microbial Count | | <10 | | | 0 |
| Total Yeast & Mold Count | | <10 Absent | | | 0 Absent |
| Escherichia Coli | | | | | |

83 the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A modified-release formulation comprising at least one modified-release pellet comprising an alkaline phosphatase (AP)-based agent contained in a capsule, wherein the modified-release formulation comprises:

about 5-15% by weight AP-based agent;
about 35-45% by weight sucrose sphere;
about 15-25% by weight hydroxypropylcellulose;
about 0.1-1% by weight of buffer salt;
about 20-30% by weight enteric polymer; and
about 1-10% by weight coating system additive, wherein the coating system additive is a mixture of glyceryl monostearate, polysorbate-80, and triethyl citrate, wherein the formulation maintains at least 80% AP-based agent activity when stored at 2-8° C. for at least 6 months.

2. The modified-release formulation of claim 1, wherein the modified-release formulation comprises:

about 10% by weight AP-based agent;
about 39% by weight sucrose sphere;
about 20% by weight hydroxypropylcellulose;
about 0.5% by weight of buffer salt; and
about 26% by weight enteric polymer.

3. The modified-release formulation of claim 1, wherein the modified-release formulation comprises:

about 10.0% by weight AP-based agent;
about 38.9% by weight sucrose sphere;
about 20.0% by weight hydroxypropylcellulose;
about 0.3% by weight of buffer salt; and
about 26.3% by weight enteric polymer.

4. The modified-release formulation of claim 1, wherein the capsule comprises about 15 mg or 5 mg of AP-based agent.

5. The modified-release formulation of claim 1, wherein the capsule comprises gelatin or hydroxypropyl methylcellulose.

6. The modified-release formulation of claim 1, wherein the AP-based agent comprises an amino acid sequence having at least 90% identity with any one of SEQ ID NOs: 1-17 and 39.

7. The modified-release formulation of claim 1, wherein the AP-based agent is substantially released in the small intestine, or in the large intestine.

8. The modified-release formulation of claim 1, wherein the formulation comprises a core particle and a base coat over the core particle, wherein the base coat comprises the AP-based agent.

9. The modified-release formulation of claim 1, wherein the formulation further comprises a modified-release coating that is substantially stable in gastric fluid.

10. The modified-release formulation of claim 1, wherein the formulation comprises a modified-release coating that is degraded by a microbial enzyme present in the gut flora.

11. The modified-release formulation of claim 1, wherein the formulation comprises a modified-release coating having a solubility that is pH-dependent.

12. The modified-release formulation of claim 1, wherein the formulation comprises a modified-release coating having a time-dependent erosion profile.

13. The modified-release formulation of claim 1, wherein the formulation further comprises an additional therapeutic agent.

14. The modified-release formulation of claim 1, wherein the buffer salt is selected from a Tris base, magnesium chloride, magnesium sulfate, zinc chloride and zinc sulfate.

15. The modified-release formulation of claim 1, wherein the enteric polymer is selected from poly(methacrylic acid-ethyl acrylate copolymer) 1:1, FS 30D, L 100-55, L 100, L 12,5, L 12,5 P, RL 30 D, RL PO, RL 100, RL 12,5, RS 30 D, RS PO, RS 100, RS 12,5, NE 30 D, NE 40 D, NM 30 D, S 100, S 12,5, and S 12,5 P.

16. The modified-release formulation of claim 1, wherein the modified-release formulation comprises:

10.0% by weight AP-based agent;
38.9% by weight sucrose sphere;
20.0% by weight hydroxypropylcellulose;
0.3% by weight of buffer salt;
26.3% by weight enteric polymer; and
4.5% by weight coating system additive, wherein the coating system additive is a combination of glyceryl monostearate, polysorbate-80, and triethyl citrate;
wherein the capsule comprises about 15 mg or 5 mg of AP-based agent; and
wherein the AP-based agent comprises an amino acid sequence having at least 90% identity with any one of SEQ ID NOs: 1-17 and 39.

17. A method of treating or preventing a radiation-induced disorder in a subject in need thereof comprising, administering to the subject a formulation of claim 1.

18. The method of claim 17, wherein the radiation-induced disorder is selected from enterocolitis due to radiation therapy for cancer, radiation-induced enteropathy, colitis, proctitis, bowel toxicity, mucosal atrophy, vascular sclerosis, progressive intestinal wall fibrosis, and a side effect of radiotherapy.

19. The method of claim 17, wherein the radiation comprises ionizing radiation, optionally wherein the radiation comprises one or more of X-rays, gamma rays, and charged particles.

* * * * *